(12) United States Patent
Thon et al.

(10) Patent No.: US 12,157,872 B2
(45) Date of Patent: Dec. 3, 2024

(54) STACKED RECIRCULATING BIOREACTOR

(71) Applicant: Stellular Bio, Inc., Watertown, MA (US)

(72) Inventors: Jonathan N. Thon, Watertown, MA (US); Jorge Valdez, Watertown, MA (US); Marcus Lehmann, Watertown, MA (US); Douglas G. Sabin, Woburn, MA (US); Shawn Murphy, Woburn, MA (US); Shweta V. Krishnan, Woburn, MA (US)

(73) Assignee: Stellular Bio, Inc., Watertown, MA (US)

( * ) Notice: Subject to any disclaimer, the term of this patent is extended or adjusted under 35 U.S.C. 154(b) by 917 days.

(21) Appl. No.: 17/259,829

(22) PCT Filed: Jul. 19, 2019

(86) PCT No.: PCT/US2019/042671
§ 371 (c)(1),
(2) Date: Jan. 12, 2021

(87) PCT Pub. No.: WO2020/018950
PCT Pub. Date: Jan. 23, 2020

(65) Prior Publication Data
US 2021/0238523 A1 Aug. 5, 2021

Related U.S. Application Data

(60) Provisional application No. 62/700,495, filed on Jul. 19, 2018.

(51) Int. Cl.
*C12M 3/06* (2006.01)
*C12M 1/12* (2006.01)
(Continued)

(52) U.S. Cl.
CPC ............ *C12M 23/16* (2013.01); *C12M 21/08* (2013.01); *C12M 23/10* (2013.01); *C12M 25/02* (2013.01)

(58) Field of Classification Search
None
See application file for complete search history.

(56) References Cited

U.S. PATENT DOCUMENTS 4,110,220 A * 8/1978 Lavender ........... B01D 63/0822
210/321.75
4,865,984 A 9/1989 Nemerson
(Continued)

FOREIGN PATENT DOCUMENTS

CA 3006063 A1 6/2017
CN 2726112 Y 9/2005
(Continued)

OTHER PUBLICATIONS

Avanzi et al., "A novel bioreactor and culture method drives high yields of platelets from stem cells," Transfusion, 2015, vol. 56, Iss. 1, pp. 170-178.
(Continued)

*Primary Examiner* — William H. Beisner
(74) *Attorney, Agent, or Firm* — Greenberg Traurig, LLP; Roman Fayerberg; George Banis

(57) ABSTRACT

The instant disclosure provides a system comprising a plurality of stacked bioreactors, wherein the system is configured to provide a substantially equal flow rate of fluid and pressure drop through each of the plurality of bioreactors. In some embodiments, the flow of the fluid through each of the plurality of bioreactors is configured to generate physiological shear rates to induce a biological source material in the bioreactors to produce target biological products.

12 Claims, 40 Drawing Sheets

(51) Int. Cl.
*C12M 1/22* (2006.01)
*C12M 3/00* (2006.01)

(56) References Cited

U.S. PATENT DOCUMENTS

| | | | |
|---|---|---|---|
| 5,895,575 | A | 4/1999 | Kraus et al. |
| 6,225,119 | B1 | 5/2001 | Qasba |
| 6,759,245 | B1 | 7/2004 | Toner et al. |
| 6,819,736 | B1 | 11/2004 | Bruder et al. |
| 7,718,420 | B2 | 5/2010 | Kim et al. |
| 8,129,179 | B2 | 3/2012 | Wikswo et al. |
| 8,279,996 | B2 | 10/2012 | Allmendinger et al. |
| 8,306,304 | B2 | 11/2012 | Noo et al. |
| 9,012,221 | B2 | 4/2015 | Baruch et al. |
| 9,163,208 | B2 | 10/2015 | Runyon |
| 9,795,965 | B2 | 10/2017 | Italiano et al. |
| 10,343,163 | B2 | 7/2019 | Italiano et al. |
| 10,590,373 | B2 | 3/2020 | Thon et al. |
| 10,710,073 | B2 | 7/2020 | Italiano et al. |
| 2002/0176804 | A1 | 11/2002 | Strand |
| 2005/0009101 | A1 | 1/2005 | Blackburn |
| 2005/0069459 | A1 | 3/2005 | Ahn et al. |
| 2005/0112184 | A1 | 5/2005 | Jahn et al. |
| 2005/0224351 | A1 | 10/2005 | Unger et al. |
| 2005/0252892 | A1 | 11/2005 | Newman |
| 2006/0154361 | A1 | 7/2006 | Wikswo et al. |
| 2006/0199260 | A1 | 9/2006 | Zhang et al. |
| 2007/0243608 | A1 | 10/2007 | Kyba et al. |
| 2010/0009430 | A1 | 1/2010 | Wan et al. |
| 2010/0041128 | A1 | 2/2010 | Banes et al. |
| 2010/0248361 | A1 | 9/2010 | Lasky |
| 2011/0000823 | A1 | 1/2011 | Hamad et al. |
| 2011/0039285 | A1 | 2/2011 | Sadaba Champetier De Ribes et al. |
| 2011/0124078 | A1* | 5/2011 | Edwards ............... C12M 29/16 435/243 |
| 2011/0243813 | A1 | 10/2011 | Jackinsky |
| 2011/0250585 | A1 | 10/2011 | Ingber et al. |
| 2012/0014933 | A1 | 1/2012 | Baruch et al. |
| 2012/0039434 | A1 | 2/2012 | Wang et al. |
| 2012/0108721 | A1 | 5/2012 | Mazutis |
| 2012/0238020 | A1 | 9/2012 | Mitchell et al. |
| 2013/0061961 | A1 | 3/2013 | Rapp |
| 2013/0280802 | A1 | 10/2013 | Schulz et al. |
| 2013/0295601 | A1 | 11/2013 | Park et al. |
| 2014/0037600 | A1 | 2/2014 | Yu |
| 2014/0061115 | A1* | 3/2014 | DiBiasio ............... B01L 3/5027 210/321.72 |
| 2014/0147880 | A1 | 5/2014 | Ingber et al. |
| 2014/0186414 | A1 | 7/2014 | Ingber et al. |
| 2014/0227780 | A1 | 8/2014 | Nishino |
| 2015/0076067 | A1* | 3/2015 | Borenstein ............ B01D 61/28 210/259 |
| 2015/0175950 | A1 | 6/2015 | Hirschel |
| 2015/0336095 | A1 | 11/2015 | Italiano et al. |
| 2015/0377861 | A1 | 12/2015 | Pant |
| 2016/0002586 | A1 | 1/2016 | Mitchell |
| 2016/0209331 | A1 | 7/2016 | Babic |
| 2016/0272941 | A1 | 9/2016 | Baruch et al. |
| 2016/0281058 | A1 | 9/2016 | Schulz et al. |
| 2016/0333295 | A1 | 11/2016 | Baker |
| 2016/0333314 | A1 | 11/2016 | Nguyen |
| 2017/0183616 | A1 | 6/2017 | Thon et al. |
| 2018/0055891 | A1 | 3/2018 | Zhao |
| 2018/0080925 | A1 | 3/2018 | Benam et al. |
| 2018/0104692 | A1 | 4/2018 | Sicot et al. |
| 2018/0111093 | A1* | 4/2018 | Griffis ................... B01D 61/44 |
| 2018/0334652 | A1 | 11/2018 | Thon |
| 2019/0283027 | A1 | 9/2019 | Italiano et al. |
| 2020/0017812 | A1 | 1/2020 | Thon |
| 2020/0255781 | A1 | 8/2020 | Thon et al. |
| 2020/0316597 | A1 | 10/2020 | Italiano et al. |
| 2023/0054335 | A1 | 2/2023 | Macias et al. |
| 2023/0365906 | A1 | 11/2023 | Thon |

FOREIGN PATENT DOCUMENTS

| | | | |
|---|---|---|---|
| CN | 102058399 | A | 5/2011 |
| CN | 102698672 | A | 10/2012 |
| CN | 1021224096 | B | 10/2014 |
| CN | 104540933 | A | 4/2015 |
| CN | 106414703 | B | 10/2019 |
| JP | 2008301746 | A | 12/2008 |
| JP | 2011528232 | A | 11/2011 |
| JP | 2012235749 | A | 12/2012 |
| JP | 2013031428 | A | 2/2013 |
| RU | 2076742 | C1 | 4/1997 |
| RU | 2246258 | C1 | 2/2005 |
| RU | 2392314 | C2 | 6/2010 |
| WO | 1986002378 | A1 | 4/1986 |
| WO | 2006001954 | A2 | 1/2006 |
| WO | 2010009307 | A2 | 1/2010 |
| WO | 2010063823 | A1 | 6/2010 |
| WO | 2010123594 | A2 | 10/2010 |
| WO | 2011002745 | A1 | 1/2011 |
| WO | 2011040889 | A1 | 4/2011 |
| WO | 2012118799 | A2 | 9/2012 |
| WO | 2013013220 | A2 | 1/2013 |
| WO | 2014100779 | A1 | 6/2014 |
| WO | 2014107240 | A1 | 7/2014 |
| WO | 2014110133 | A1 | 7/2014 |
| WO | 2015138032 | A2 | 9/2015 |
| WO | 2015153451 | A1 | 10/2015 |
| WO | WO-2017044149 | A1 * | 3/2017 ............. A61K 35/19 |
| WO | 2018094003 | A1 | 5/2018 |

OTHER PUBLICATIONS

Bender et al., "Microtubule sliding drives proplatelet elongation and is dependent on cytoplasmic dynein," Blood, Jan. 29, 2015, vol. 125, No. 5, pp. 860-868.

Feng et al., "Scalable Generation of Universal Platelets from Human Induced Pluripotent Stem Cells," Stem Cell Reports, 2014, vol. 3, pp. 817-831.

Nakagawa et al., "Two Differential Flows in a Bioreactor Promoted Platelet Generation from Human Pluripotent Stem Cell-Derived Megakaryocytes," Experimental Hematology, 2013, vol. 41, Iss. 8, pp. 742-748.

Synnevag et al., "Adaptive beamforming applied to medical ultrasound imaging," IEEE Transactions on Ultrasonics, Ferroelectrics, and Frequency Control, 2007, vol. 54, No. 8, pp. 1606-1613.

Tehranirokh et al., "Microfluidic Devices for Cell Cultivation and Proliferation," Biomicrofluidics, 2013, vol. 7, Iss. 5, pp. 1-32.

Thon et al., "Platelet bioreactor-on-a-chip," Blood, Sep. 18, 2014, vol. 124, No. 12, pp. 1857-1867.

Thon et al., "Road blocks in making platelets for transfusion," Journal of Thrombosis and Haemostasis, 2015, vol. 13, Suppl. 1, pp. S55-S62.

Baigger et al., ""Towards the Manufacture of Megakaryocytes and Platelets for Clinical Application" Transfus. Med. Hemother. Vol. 44, pp. 165-173, 2017."

Borger et al., "Generation of HLA-Universal iPSC-Derived Megakaryocytes and Platelets for Survival underRefractoriness Conditions""Mol. Med. vol. 22, pp. 274-285, 2016."

Hirata et al., "Selective Inhibition of ADAM17 Efficiently Mediates Glycoprotein Ib[alpha] Retention During EX VivoGeneration of Human Induced Pluripotent Stem Cell-Derived Platelets""Stem Cells Translational Medicine, vol. 6, No. 3, pp. 720-730, Mar. 1, 2017."

Kronke et al., "Lenalidomide Induces Ubiquitination and Degradation of CK1a in del(5q) MDS""Nature, vol. 523, No. 7559, pp. 183-188, Jul. 1, 2015."

Lambert et al., "Challenges and Promises for the Development of Donor-Independent Platelet Transfusions""Blood, American Society of Hematology, US, vol. 121, No. 17, pp. 3319-3324, Jan. 15, 2013."

Liu et al., "Efficient Generation of Megakaryocytes from Human Induced Pluripotent Stem Cells Using Food and DrugAdministration-

(56) References Cited

OTHER PUBLICATIONS

Approved Pharmacological Reagents""Stem Cells Translational Medicine, vol. 4, No. 4, pp. 309-319,Apr. 1, 2015."
Sakar et al., "Drug Delivery Using Platelet Cancer Cell Interaction""Pharmaceutical Research, vol. 30, No. 11, pp. 2785-2794, Jun. 6, 2013."
Solomon et al., "Current Perspectives on the Use of Ancillary Materials for the Manufacture of Cellular Therapies""Cytotherapy, vol. 18, Iss. 1, pp. 1-12, Jan. 31, 2016."
Sullivan et al., "High-Level Transgene Expression in Induced Pluripotent Stem Cell-Derived Megakaryocytes: Correction of Glanzmann Thrombasthenia""Blood, vol. 123, No. 5, pp. 753-757, 2014."
European Search Report in European Application No. EP 19 83 7896 mailed Mar. 15, 2022.
Sarkar et al., "Drug Delivery Using Platelet Cancer Cell Interaction" Pharmaceutical Research, vol. 30, No. 11, pp. 2785-2794, Jun. 6, 2013.
U.S. Appl. No. 16/490,711, 2020/0017812, filed Sep. 3, 2019 Jan. 16, 2020, Recirculating Bioreactor.
International Search Report in International Application No. PCT/US2019/042671 mailed Oct. 23, 2019.

\* cited by examiner

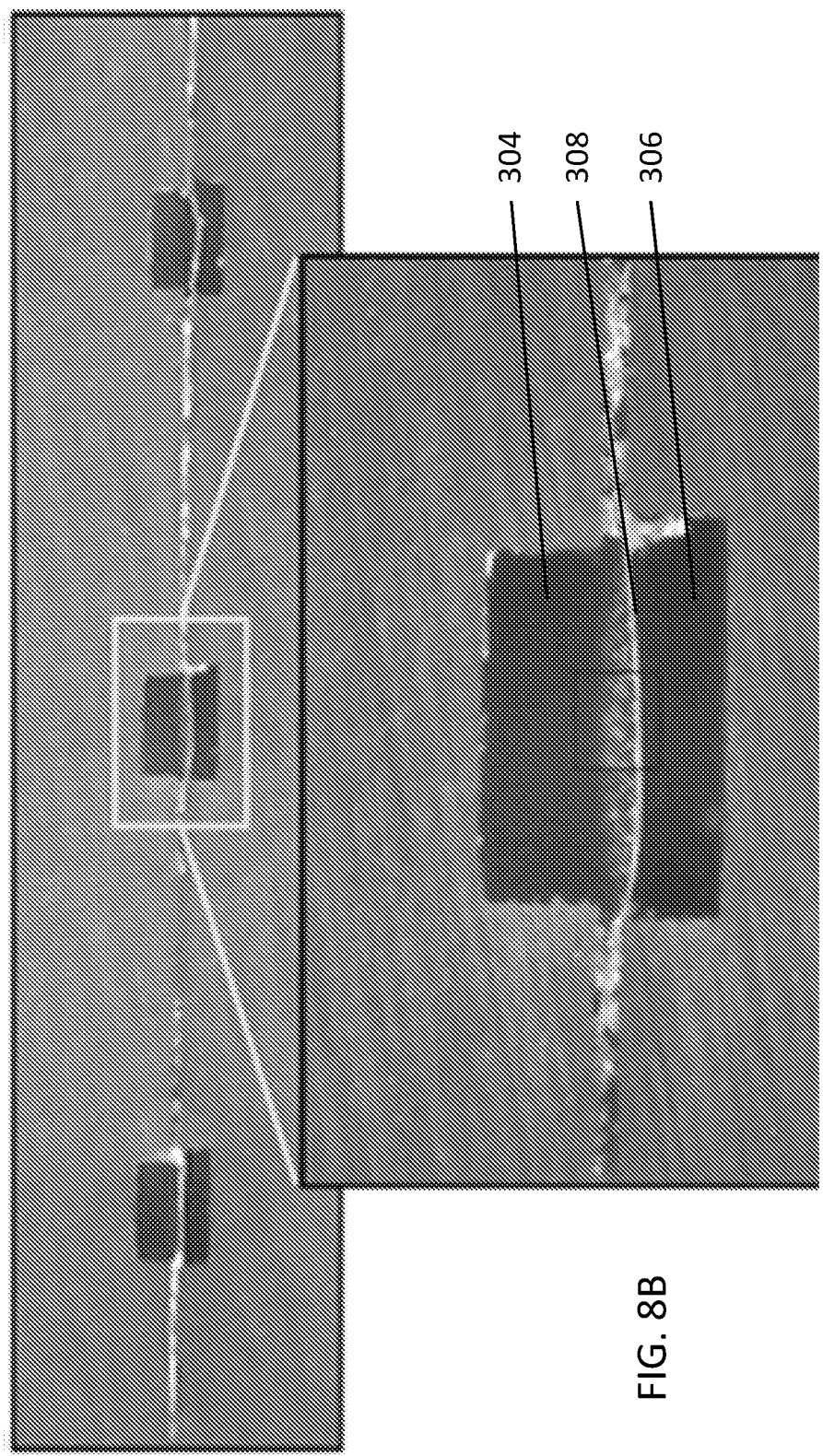

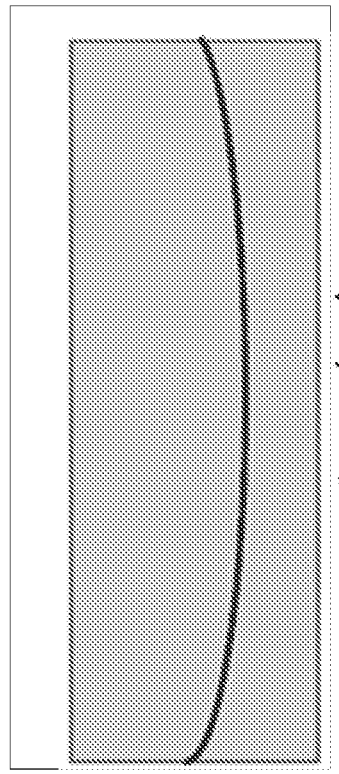
FIG. 9B Stretched
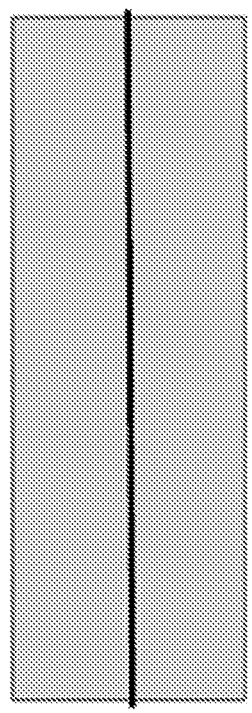
FIG. 9A Resting

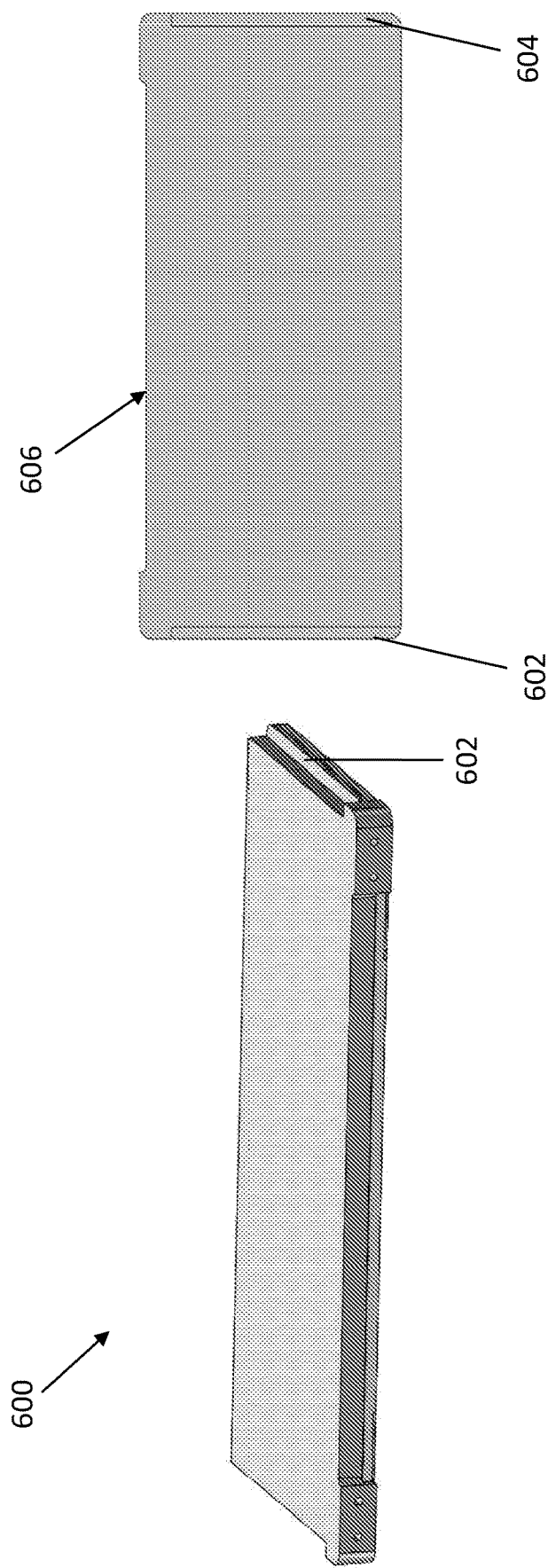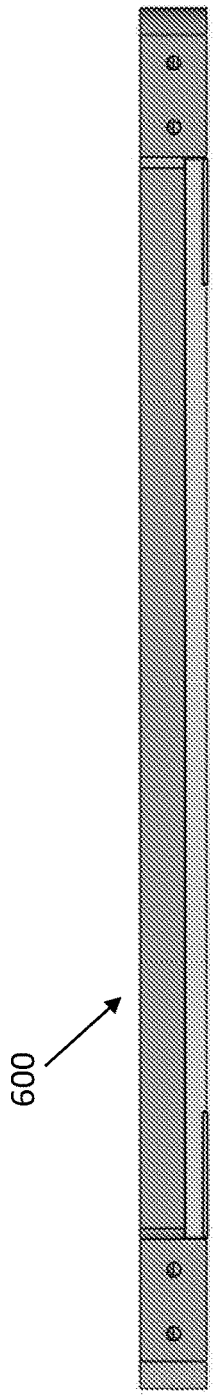
FIG. 12A
FIG. 12B
FIG. 12C

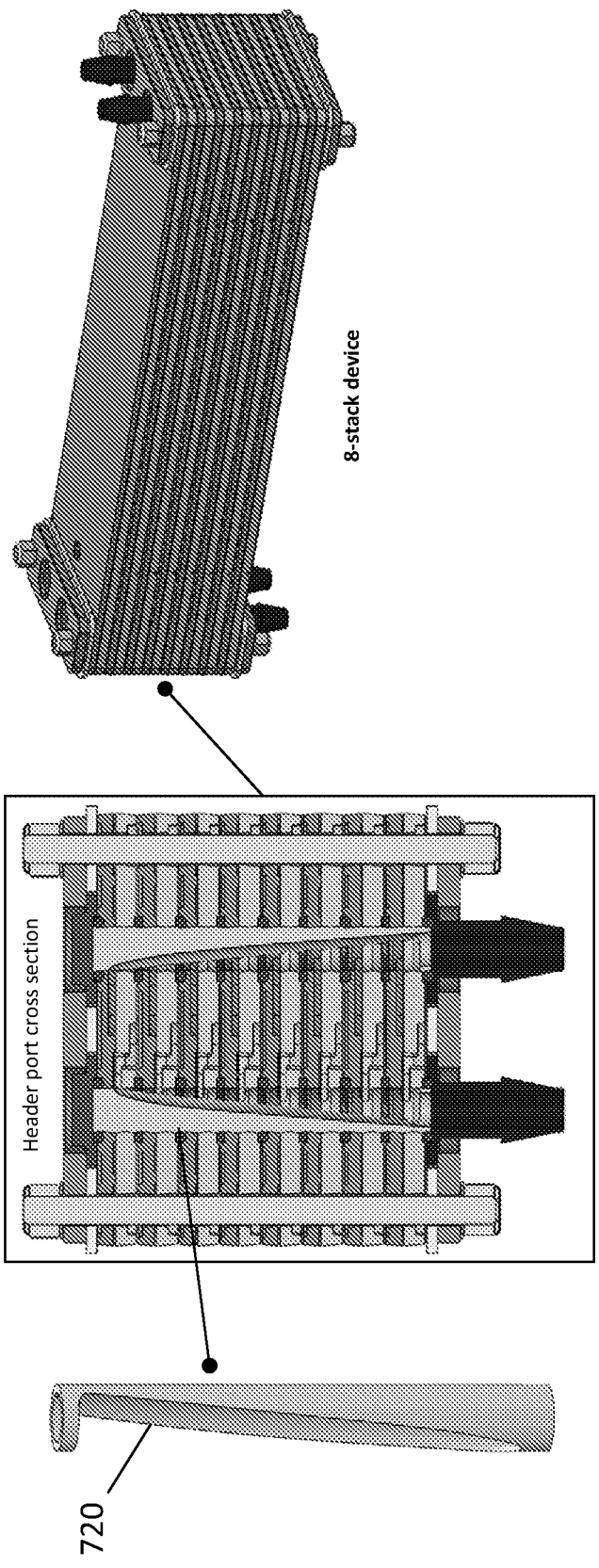

STACKED RECIRCULATING BIOREACTOR

RELATED APPLICATIONS

This application is a U.S. national phase application of PCT International Patent Application No. PCT/US2019/042671, filed on Jul. 19, 2019, which claims the benefit of and priority to U.S. Provisional Application Ser. No. 62/700,495, filed on Jul. 19, 2018, the entirety of each of which is hereby incorporated herein by reference.

STATEMENT OF GOVERNMENT SUPPORT

This invention was made with government support under 5R44HL131050 awarded by the National Institutes of Health (NIH) and under W81XWH1810187 awarded by the Department of Defense. The government has certain rights in the invention.

FIELD

The present disclosure generally relates to fluid systems and more particularly to bioreactors.

BACKGROUND

In medical practice, various biological products can be used to treat various disorders, infections, malignancies, and traumas. Additionally, such biological products (e.g., plasma, platelets, white blood cells, red blood cells) can be used to replace depleted biological products within a patient. Production of such biological products has been attempted using various techniques such as production from various stem cells. Stem cells utilized have typically included embryonic stem cells, umbilical cord blood stem cells and induced pluripotent stem cells. Other stem cell sources have included stem cells found in bone marrow, fetal liver and peripheral blood. However, despite successful production of some biological products in the laboratory, many limitations remain to use in a clinical setting.

Therefore, there remains a need for efficient ways to produce clinically relevant yields of biological products that can meet growing clinical demands, and avoid the risks and costs associated with donor harvesting and storage.

SUMMARY

The instant disclosure describes various bioreactor embodiments and methods of their use in one or more stacked configurations that include a number of features and capabilities aimed at generating clinically and commercially relevant biological products from biological source materials. In some embodiments, the system and method described herein may be used to generate high platelet yields usable for platelet infusion.

In some aspects, the instant disclosure provides a system that comprises a plurality of stacked bioreactors, each bioreactor comprising: a first channel configured to receive at least one first fluid at a first channel flow rate; a second channel configured to receive at least one second fluid at a second channel flow rate; and a separation barrier between the first channel and the second channel, the separation barrier having a plurality of microchannels forming a fluid communication path between the first and second channels; a first inlet manifold in fluid communication with the first channel of each of the plurality of bioreactors and configured to distribute flow through the first channel of each of the plurality of bioreactors; and a second inlet manifold in fluid communication with the second channel of each of the plurality of bioreactors and configured to distribute flow through the second channel of each of the plurality of bioreactors, one or more outlet manifolds in fluid communication with at least one of the first channels and the second channels of each of the plurality of bioreactors to collect the first fluid and the second fluid from the bioreactors, wherein the system is configured to provide a substantially equal flow rate of the first fluid and the second fluid through each of the plurality of bioreactors.

In some embodiments, the one or more outlet manifolds includes a first outlet manifold in fluid communication with the first channels of each of the plurality of bioreactors and a second outlet manifold in fluid communication with the second channels of each of the plurality of bioreactors. In some embodiments, the first inlet manifold and second inlet manifold are configured to ensure a substantially equal pressure drop across each of the plurality of bioreactors. In some embodiments, a flow path through the plurality of the bioreactors is defined by the first inlet manifold, the second inlet manifold, the one or more outlet manifolds, and the plurality of the bioreactors, the flow path being configured to ensure a substantially equal pressure drop across each of the plurality of bioreactors. In some embodiments, the substantially equal pressure drop across each of the plurality of bioreactors ensures a substantially equal flow through each of the plurality of bioreactors. In some embodiments, the first inlet manifold and second inlet manifold are shaped to ensure a substantially equal pressure drop across each of the plurality of bioreactors. In some embodiments, the first inlet manifold and second inlet manifold include an insert to create a substantially equal pressure drop across each of the plurality of bioreactors. In some embodiments, first channel, the second channel or both have a variable cross-section along the length to impart a consistent pressure drop across the membrane along the entire length of the membrane. In some embodiments, the substantially equal pressure drop across the membrane along the entire length of the membrane ensures a substantially equal flow through the membrane along its length to distribute the first fluid substantially equally along the length of the membrane. In some embodiments, the system further comprises one or more pumps in fluid communication with the first inlet manifold and the second inlet manifold. In some embodiments, a single pump head is configured to provide flow to the first and second inlet manifolds to ensure a substantially equal pulsatile flow in the first and second inlet manifolds channels. In some embodiments, each bioreactor further comprises a bioreactor body and wherein the first channel, the second channel, a portion of the first inlet manifold and a portion of the second inlet manifold are formed in the bioreactor body of each bioreactor. In some embodiments, the plurality of bioreactors are stacked in a vertical configuration.

In some aspects, the instant disclosure provide a system comprising: a plurality of stacked bioreactors, each bioreactor comprising: a first channel configured to receive at least one first fluid at a first channel flow rate, the at least one first fluid comprising a biological source material capable of producing target biological products; a second channel configured to receive at least one second fluid at a second channel flow rate; and a separation barrier between the first channel and the second channel, the separation barrier having a plurality of microchannels forming a fluid communication path between the first and second channels, wherein the plurality of microchannels are sized to selectively capture the biological source material, a first inlet manifold in fluid communication with the first channel of each of the plurality of bioreactors and configured to distribute flow through the first channel of each of the plurality of bioreactors; and a second inlet manifold in fluid communication with the second channel of each of the plurality of bioreactors and configured to distribute flow through the second channel of each of the plurality of bioreactors, one or more outlet manifolds in fluid communication with at least one of the first channels and the second channels of each of the plurality of bioreactors to collect the first fluid and the second fluid from the bioreactors, wherein the system is configured to provide a substantially equal flow rate of the first fluid and the second fluid through each of the plurality of bioreactors, and wherein the flow of the first fluid and the second fluid through each of the plurality of bioreactors is configured to generate physiological shear rates along a surface of the membrane in the second channel to induce the biological source material captured by the membrane to produce the target biological products. In some embodiments, the biological source material comprises megakaryocytes and the biological products are platelets.

In some aspects, the present disclosure provides a system comprising: a plurality of stacked bioreactors, each bioreactor comprising: a first channel configured to receive at least one first fluid at a first channel flow rate; a second channel configured to receive at least one second fluid at a second channel flow rate; and a separation barrier between the first channel and the second channel, the separation barrier having a plurality of microchannels forming a fluid communication path between the first and second channels, a manifold in fluid communication with each of the plurality of stacked bioreactors, the manifold comprising a first main inlet channel having a plurality of first secondary inlet channels fluidly connecting the first inlet manifold to the first channel of each of the plurality of bioreactors; and a second main inlet channel having a plurality of the second secondary inlet channels fluidly connecting the second inlet manifold with the second channel of each of the plurality of bioreactors; and one or more outlet channels in fluid communication with at least one of the first channel or the second channel, wherein a length of the first secondary inlet channels and the second secondary inlet channels decreases based on a distance from an inlet to the first main inlet channel or a second main inlet channel, respectively.

In some aspects, the present disclosure provides a method for operating a bioreactor, the method comprising: directing fluid flow to a first inlet manifold and a second inlet manifold of a system comprising a plurality of stacked bioreactors, each bioreactor comprising: a first channel in fluid communication with the first inlet manifold and being configured to receive at least one first fluid at a first channel flow rate; a second channel in fluid communication with the second inlet manifold configured to selectively receive at least one second fluid at a second channel flow rate; and a separation barrier between the first channel and the second channel, the separation barrier having a plurality of microchannels forming a fluid communication path between the first and second channels, one or more outlet manifolds in fluid communication with at least one of the first channels and the second channels of each of the plurality of bioreactors to collect the first fluid and the second fluid from the bioreactors; distributing the fluid from the first inlet manifold through the first channel of each of the plurality of bioreactors; distributing the fluid from the second inlet manifold through the second channel of each of the plurality of bioreactors; adjusting a flow rate of the fluid to the bioreactors to expose a biological source material seeded on the membranes to a desired shear rate in the second channel to cause the biological source material to produce a target biological product.

In some embodiments, the method further comprises circulating the fluid through each of the plurality of bioreactors at a substantially equal flow rate. In some embodiments, the method further comprises providing a substantially equal pressure drop across each of the plurality of bioreactors. In some embodiments, the method further comprises seeding the biological source material in each bioreactor of the plurality of bioreactors. In some embodiments, the method further comprises replenishing the biological source material in each bioreactor of the plurality of bioreactors as the existing biological source material becomes deactivated. In some embodiments, the flow through the first channel enters a first inlet in the first channel and flows through the membrane into the second channel. In some embodiments, the flow through the second channels enters a second inlet and flows through the second channel to exit a second outlet. In some embodiments, the biological source material comprises megakaryocytes and the target biological product comprises platelets.

In some aspects, the present disclosure provide a method for operating a bioreactor, the method comprising directing a fluid to a first inlet manifold and a second inlet manifold of a system comprising a plurality of stacked bioreactors, each bioreactor comprising: a first channel in fluid communication with the first inlet manifold and being configured to receive at least one first fluid at a first channel flow rate; a second channel in fluid communication with the second inlet manifold configured to selectively receive at least one second fluid at a second channel flow rate; and a separation barrier between the first channel and the second channel, the separation barrier having a plurality of microchannels forming a fluid communication path between the first and second channels, one or more outlet manifolds in fluid communication with at least one of the first channels and the second channels of each of the plurality of bioreactors to collect the first fluid and the second fluid from the bioreactors; distributing the fluid from the first inlet manifold through the first channel of each of the plurality of bioreactors; distributing the fluid from the second inlet manifold through the second channel of each of the plurality of bioreactors; introducing a concentration of a biological source material into the fluid; circulating the flow through each of the plurality of bioreactors at a substantially equal flow rate such that the biological source material is distributed uniformly through the plurality of the bioreactors.

In some aspects, the present disclosure provides a bioreactor comprising: a first channel configured to receive at least one first fluid at a first channel flow rate, the at least one first fluid; a second channel configured to receive at least one second fluid at a second channel flow rate; and a separation barrier between the first channel and the second channel, the separation barrier having a plurality of microchannels forming a fluid communication path between the first and second channels, wherein the plurality of microchannels are sized to selectively capture the biological source material, wherein the first channel, the second channel or both have a variable cross-section that varies non-linearly along the length of the channel to impart a consistent pressure drop across the membrane along the entire length of the membrane when the first fluid and the second fluid are circulated through the first channel and the second channel. In some embodiments, at least one of the first channel or the second channel are sized to impart a uniform shear rate along a surface of the membrane.

In some aspects, the present disclosure provides a method for operating a bioreactor comprising: distributing fluid through an inlet manifold to a plurality of bioreactors; introducing a first concentration of biological source material into the inlet manifold such that the biological source material is distributed among the plurality of the bioreactors; exposing the biological source material in the bioreactors to shear stress to induce the biological source material to produce a target biological product; and introducing a second concentration of biological source material to the inlet manifold to replenish the biological material from the first concentration of biological material. In some embodiments, the method further comprising maintaining a substantially equal flow rate of the fluid through each bioreactor of the plurality of bioreactors such that the biological source material is distributed uniformly among the bioreactors.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 8A and 8B are detail views of a cross-sectional side view of a bioreactor channel in accordance with various embodiments;

FIGS. 9A and 9B are cross-sectional side views illustrating a resting position and a stretched position of a flexible membrane of a bioreactor channel in accordance with various embodiments;

FIGS. 12A, 12B, and 12C illustrate a perspective, top, and side view of an embodiment of a bioreactor with features relating to stacking one or more bioreactors;

FIGS. 13A, 13B, 13C, 13D, 13E, 13F, 13G, and 13H illustrate additional embodiments for fluidly connecting the bioreactors of the present disclosure;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides systems and methods capable of efficient and scalable production of biological products, such as platelets. There remains a need for efficient ways to produce clinically relevant yields of biological products that can meet growing clinical demands, and avoid the risks and costs associated with donor harvesting and storage. The present disclosure addresses such needs.

The present disclosure relates to systems and methods that include a fluidic bioreactor, for example, a millifluidic bioreactor, a microfluidic bioreactor, or clusters of such reactors, that can be used to generate biological products/target biological substance from biological source material. In some embodiments, a plurality of bioreactors can be used together, for example in a stacked configuration, to produce an increased yield of a desired cell type.

In some embodiments, the term "biological source material" refers to a biological material that may produce or give rise to another biological material when subjected to shear stress. For example, biological materials can include, but are not limited to, a suspension of cells, for example, megakaryocytes, CHO cells, or yeast cells, or living organisms.

In some embodiments, the term "biological products" refers to a biological product that can result from the biological source material being exposed to shear stress, for example, imparted by the flow rate, as well as nutrient and gas transport being facilitated by the medium flow rate. Biological product can be produced by the biological source material by triggering cytoskeletal changes in response to shear, being extruded from the source material, or allowing secretion of product from the source material. Biological product examples can include, but are not limited to, platelets, microparticles, vesicles, proteins such an antibodies and growth factors, and plasmids.

Figure 1:
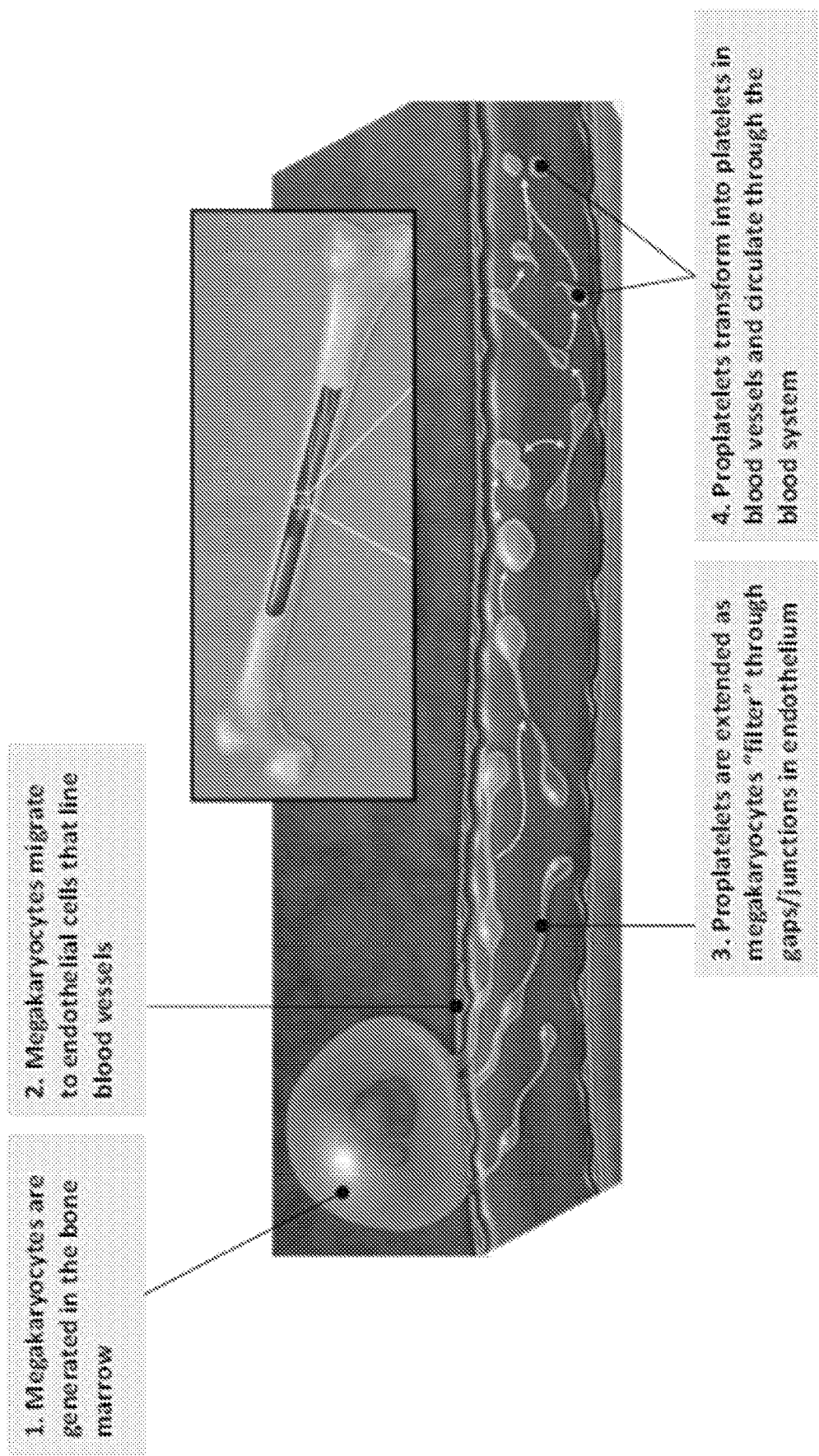
FIG. 1 is an illustration showing in vivo platelet production in bone marrow.

For example, the present bioreactor can be used to replicate a process that produces platelets, such as the process shown in FIG. 1. As illustrated in FIG. 1, megakaryocytes generated in the bone marrow move toward and settle onto endothelial cells that line blood vessels. There they extend long, branching cellular structures called proplatelets into the blood vessel space through gaps in the endothelium. Experiencing shear rates due to blood flow, proplatelets extend and release platelets into the circulation. For example, proplatelets experience wall shear rates ranging from, 100 to 10,000 s-1 or, more particularly, from 500 to 2500 s-1.

It will be understood that any flow rate through a bioreactor can be used to achieve cell culture depending on the cell type and desired yield. In accordance with various embodiments, the bioreactor can support high yield cell culture at much smaller volumes, which enables substantial cost reductions in cell culture. Such cost reductions can provide commercially feasible, cost efficient production of biological products, thereby permitting translation of production processes to commercially feasible industrial production for clinical use. It will be understood that while the systems and methods of the present disclosure are described in connection with the production of platelets from megakaryocytes, the present methods and systems can be used in connection with other biological source materials to produce corresponding biological products.

Figure 2:
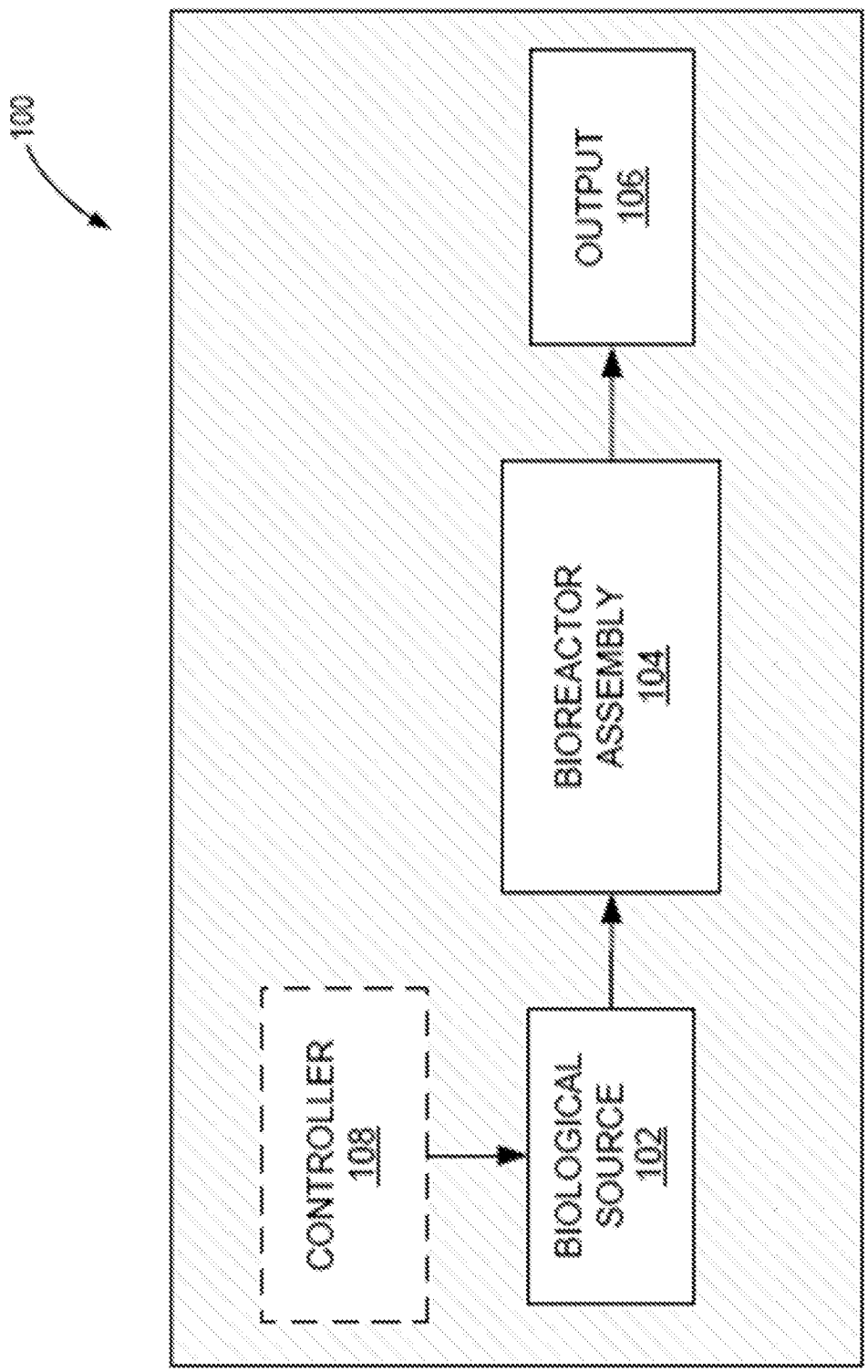
FIG. 2 is a block diagram illustrating a system for producing biological products, in accordance with various embodiments.

Turning now to FIG. 2, a schematic diagram of an exemplary embodiment of a system 100 for biological products, is shown. In general, the system 100 includes a pump 102 for providing biological source 102, a bioreactor assembly 104, and an output 106, where the biological source 102 and output 106 are connectable to various inputs and outputs of the bioreactor assembly 104, respectively. The bioreactor assembly 104 can be in the form of a single flow path bioreactor, a multiple flow path bioreactor, or a stacked configuration of a plurality of single flow path or multiple flow path bioreactors, as will be explained in more detail below.

Specifically, the biological source 102 can be configured with various capabilities for introducing into the bioreactor assembly 104 different biological source materials, substances, gas, or fluid media, to efficiently produce desirable biological products, such as, for example, platelets. For instance, the biological source 102 can include one or more pumps for delivering, sustaining, and/or recirculating fluid media in the bioreactor assembly 104. Examples include but are not limited to fluidic pumps, syringe pumps, peristaltic pumps, pneumatic pumps, and the like. The biological source materials can include but are not limited to cells, cell culture media, small molecule compounds, gases and gas mixtures, and nutrients. In some embodiments, the biological source includes a biological source material that is delivered to the bioreactor to produce a desired biological product.

As shown in FIG. 2, in some embodiments, the system 100 can also include a controller 108 for controlling the biological source 102. Specifically, the controller 108 can be a programmable device or system configured to control the operation of the bioreactor assembly 104, including the timings, amounts, and types of biological source material, substances, fluid media or gas introduced therein. In some aspects, the controller 108 can be configured to selectively functionalize and/or operate the bioreactor assembly 104 to recreate physiological conditions and processes associated with cell differentiation (e.g., platelet production) in the human body. For example, the controller 108 can be programmed to deliver a selected number of megakaryocytes to the bioreactor assembly 104. In addition, the controller 108 can control fluid flow rates or fluid pressures in the bioreactor assembly 104 to facilitate proplatelet extension and platelet production. For instance, the controller 108 can establish flow rates up to 150,000 microliters/hr in various channels configured in the bioreactor assembly 104, or any flow rate necessary to establish a local shear rate that triggers platelet production from the seeded megakaryocytes, or other biological products.

Although the controller 108 is shown in FIG. 2 as separate from the biological source 102, it can be appreciated that these can be combined into a single unit. In some embodiment, the biological source 102 and controller 106 can be embodied in a programmable fluidic pump or injection system. In addition, in some implementations, the controller 108 and/or biological source 102 can also include, communicate with, or received feedback from systems or hardware (not shown in FIG. 2) that can regulate the temperature, light exposure, vibration, pressure, shear rate, shear stress, stretch, and other conditions of the bioreactor assembly 104.

Referring back to FIG. 2, in general, the output 106 is configured to receive fluid media containing various biological products generated in the bioreactor assembly 104. In some embodiments, such effluent can be redirected or circulated back into the bioreactor assembly 104. In this manner, less fluid volume may be utilized, and the biological products generated can be more concentrated. In some aspects, the output 106 can also include capabilities for collecting, storing and/or further processing received fluid media. In some embodiments, such features can advantageously improve efficiency of the biological product generation process, thereby reducing manufacturing costs. In some embodiments, such capabilities can be used for quality control purposes, where, for example, platelets and nucleated cells in circulation can be monitored, as well as culture conditions such as partial pressure of different gases, temperature, and humidity. Other quality assessment tests can include measurement of cell distribution (for example, optical measurement), pressure of the testing system, volume of the testing system, and nucleated versus non-nucleated cell count. In some embodiments, the bioreactors can be coupled with microscopy systems to visualize cell distribution. In some embodiments, a bioreactor can be transparent to allow for visualization and assessment of operation. In some embodiments, ports can be included to sample cells. In some embodiments, features can be included to collect the product for further processing or storage, such as a bag.

Platelet recirculation can contribute to the generation of mature platelets, as immature platelets are initially produced as larger than average platelets. Recirculation can contribute to the maturation of newly generated platelets. Furthermore, agitation is required to impede platelets from activating. Recirculation of generated platelets can similarly prevent activation caused by static platelet prolonged contact with interfaces. Filtration elements such as hollow fibers, as well as centrifugation units can be introduced in line (for example, in the systems shown in FIGS. 3B-3C) to concentrate the platelet product and remove byproducts outside the target size range of 1-5 µm (or other, depending on the application). The byproducts can either be removed into waste or isolated for characterization or repurposing, for example, platelet microparticles, of size smaller than 1 µm. These elements can also be used to exchange medium in cases where the medium used for production needs to be different from that used for storage. For example, and appropriate medium for megakaryocyte production of platelets can be exchanged after production with a medium appropriate for platelet storage, for example, platelet additive solution and synthetic plasma mixtures.

It can be appreciated that the above-described system 100 has a broad range of functionality, and need not be limited to replicating physiological conditions or processes, nor producing platelets. That is, the system 100 can be used to generate a wide variety of biological products. For instance, the system 100 can be used to support cell culture and/or separate various biological source materials or substances, cells at various stages of their differentiation process, and collect their products or content. Specifically, by controlling media composition, fluid flow, and pressures, as well as other conditions, various biological source materials may be produced and released and subsequently harvested. Example biological products include, but are not limited to, isolation of cells from cell mixture or at various stages of differentiation, growth factors, antibodies, and other components found in cells. Controlling operating conditions such as temperature, pH, concentration of compounds or proteins, can be used to influence the properties of the biological products, such as platelet activation state, platelet compound or protein loading, protein conformation, and product yield. Produced biological products, in accordance with the present disclosure, in addition to clinical use, can find use in a variety of applications including isolation of cells from cell mixture, differentiation of cell progenitors, generation of tissues, and as components of cell culture medias and cosmeceuticals, such as cosmetics, shampoos, skin additives, creams, or cleaners, and so forth.

Various embodiments of the above system 100 will now be described. It can be appreciated that these are non-limiting examples, and indeed various modifications or combinations are possible and considered by one of ordinary skill in the art to be within the intended scope of the present application.

Figure 3A:
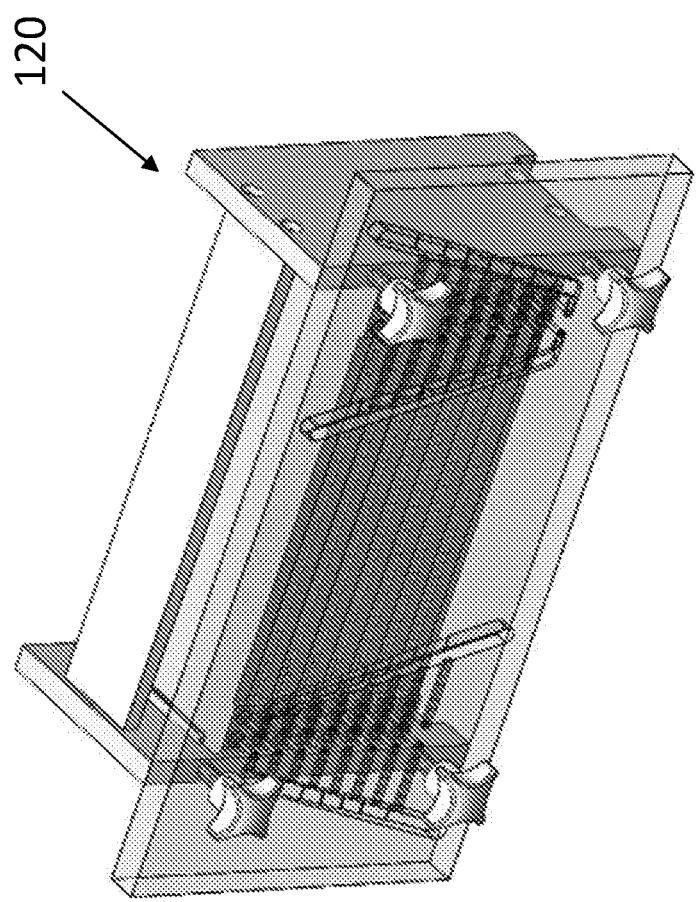
FIG. 3A illustrates an embodiment of stacked bioreactors.

As shown in FIG. 3A, a plurality of bioreactors, with separate inlets and outlets for the first channel (biological source material, such as megakaryocytes (MK)) and the second channel (biological products, such as platelets, (P)LT) sections of the bioreactor which are separated by a membrane, can be multiplexed into a single device with multiple channels. Various configurations of bioreactors can be used in parallel to form the stacked configuration 120 such that any number of single flow path or multiple flow path bioreactors can be stacked in various ways. In some embodiments, the bioreactors are stacked in a vertical configuration.

Figure 3B:
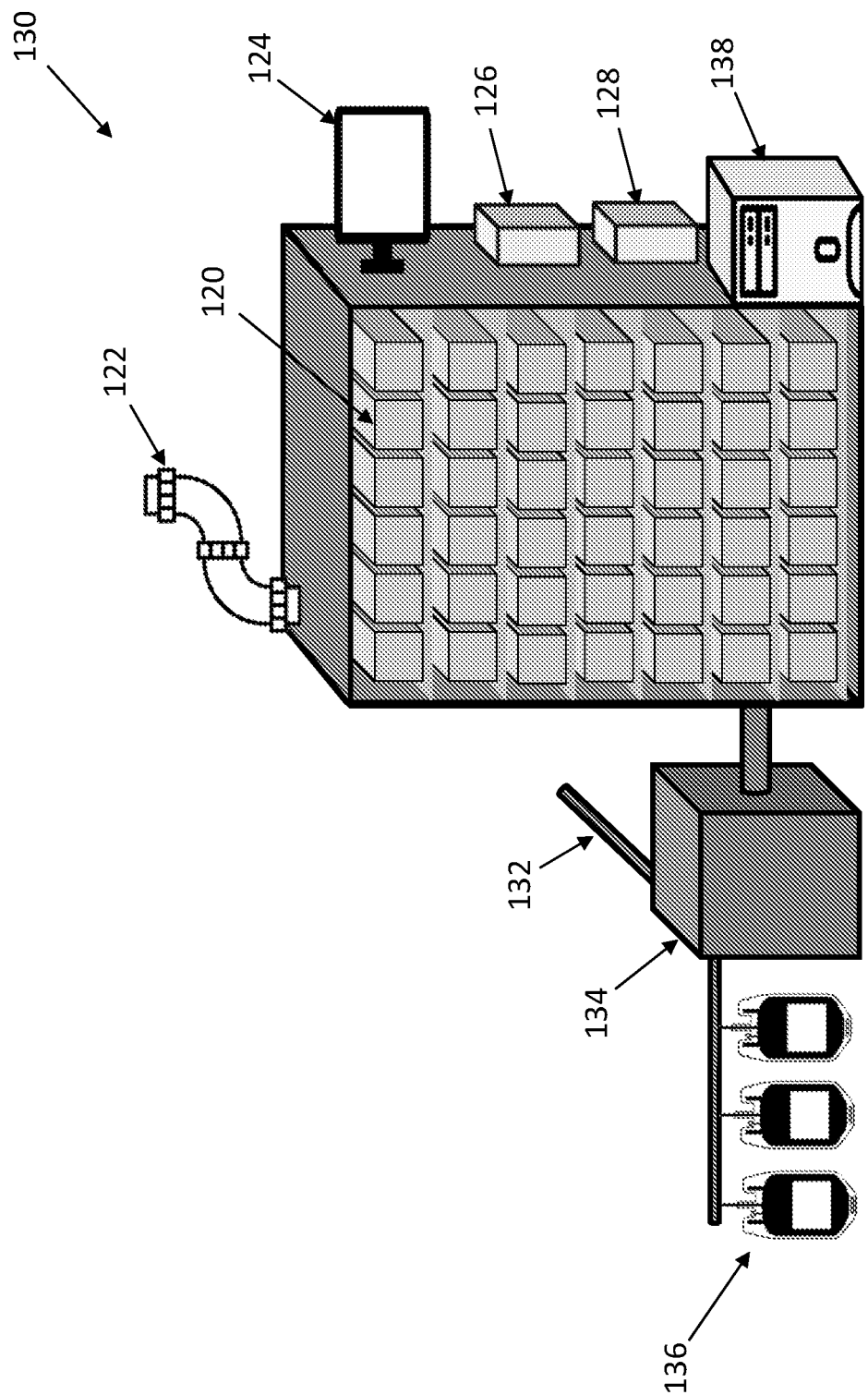
FIG. 3B illustrates an embodiment of a system for producing biological products including a bioreactor assembly in the form of a multi-stack reactor.
Figure 3C:
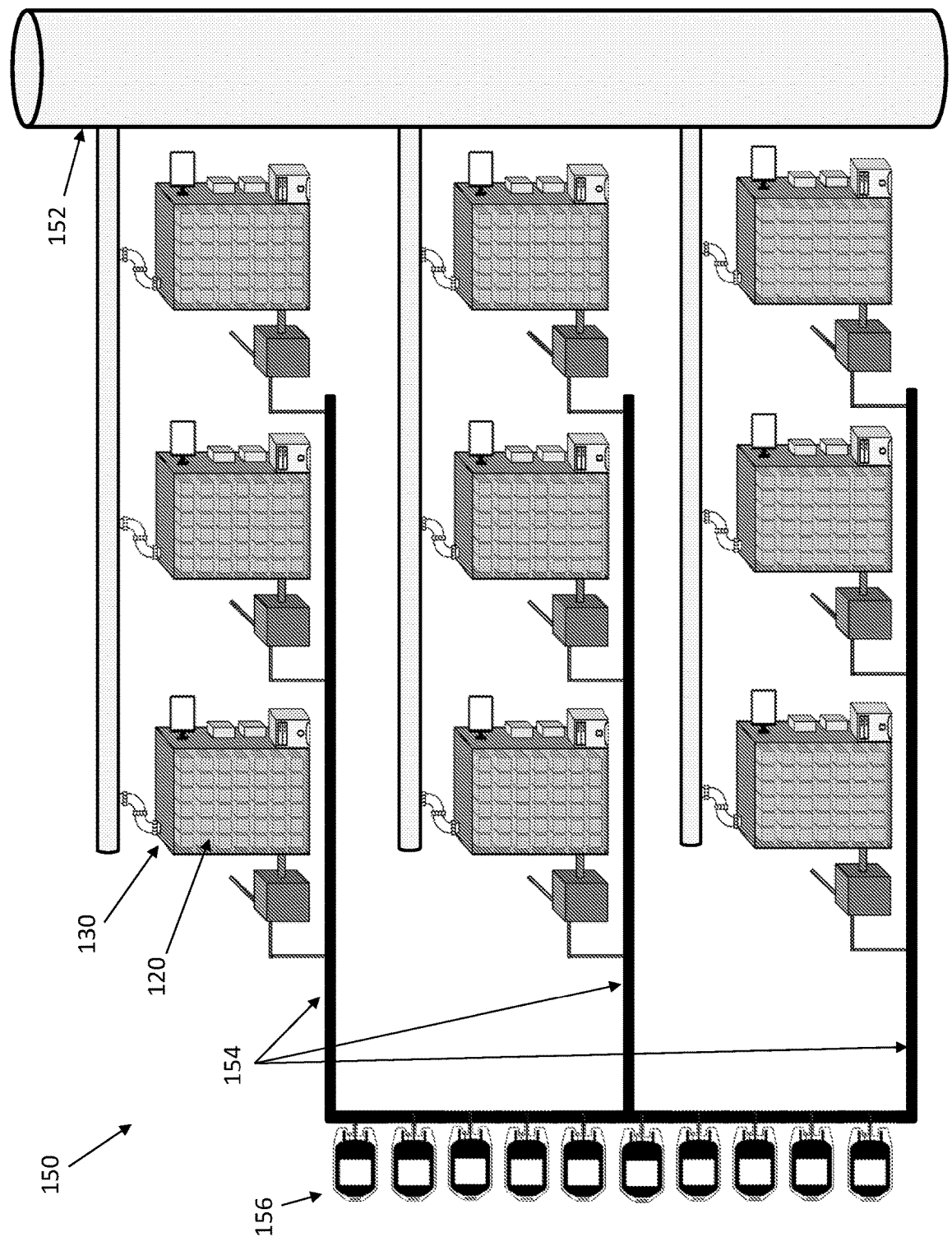
FIG. 3C illustrates an embodiment of a multi-stack reactor plant having a plurality of multi-stack reactors to form a modular, scalable bioreactor system.
Figure 4A:
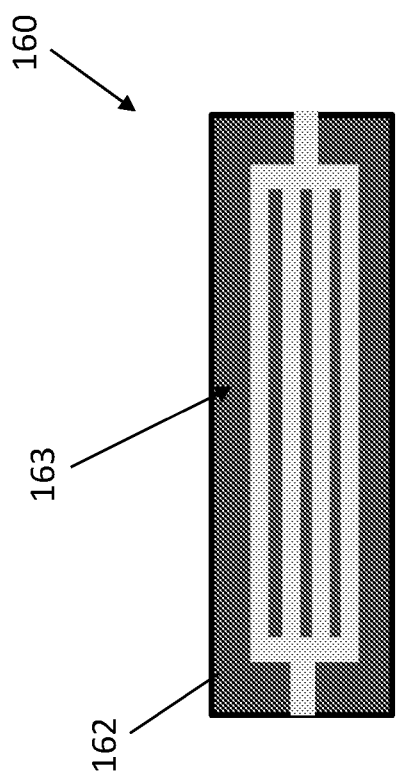
FIG. 4A and FIG. 4B illustrate an embodiment of a bioreactor.
Figure 4B:
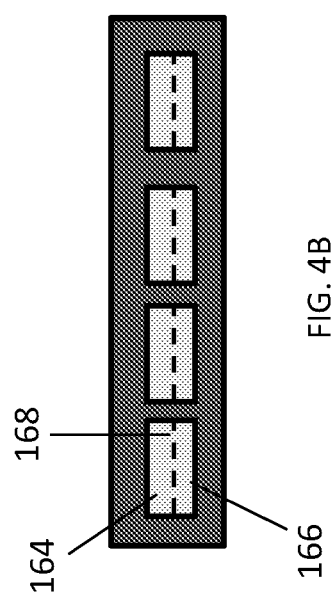

Referring now to FIGS. 3B-3C, various embodiments of a stacked platelet production bioreactor system are shown. Referring now to FIG. 3B, further scalability is contemplated by use of a stacked bioreactor including a plurality of modular tablet bioreactors arranged in a stack for increased production capacity. FIG. 3B illustrates an embodiment of a system for producing biological product that includes a plurality of stacked multiple flow path bioreactor units 120 to form a multi-stack reactor 130 having a single inlet 122. The system includes a user interface 124, such as a display/control screen, that allows operational variables to be controlled by a controller and/or cell monitoring unit 138. Control can be achieved in a variety of ways, including remotely (for example, using the cloud). Data relating to quality assessment of the product can be collected automatically and can be shared by any data transfer method for use in controlling the system and production of the biological product. Such data can include, but is not limited to, cell counts discriminating between nucleated and anucleated cells, system pressure, system media volume, temperature, pH, flow rate, volume, $CO_2$ concentration, $O_2$ concentration, and partial pressure of different gases. The multi-stack reactor 130 can also include a recirculation pump 126, a heating unit 128, a waste outlet 132, a concentration and media exchange unit 134, and one or more collection devices 136, such as bags, to collect the output of the multi-stack reactor 130. Referring now to FIG. 3C, still further scalability is contemplated by use of an industrial bioreactor including a plurality of the stacked bioreactors for still further increased production capacity. In some embodiments, a plurality of multiple flow path bioreactor stacks (such as the multi-stack reactor 130 that include a plurality of bioreactors 120, as shown in FIG. 3B) can be used to form a bioreactor plant 150 to scale up production of the biological product. The bioreactor plant 150 can include a main inlet 152, concentrated outlets 154, and one or more collection devices 156, such as platelet unit bags. Optionally, in some embodiments, all or part of the system can be positioned inside a temperature and/or gas controller that can include controls for environmental factors. The environmental factors in the system can influence the productivity and viability of the biological source material, for example, megakaryocytes, and can also influence the stability of the product, for example, platelets or produced protein.

FIGS. 4-8 illustrate embodiments of bioreactors that can be used to support cell culture and can be stacked to increase production of biological products.

In some embodiments, a plurality of single flow path or multiple flow path bioreactors can be used together to form a stacked bioreactor. For example, a bioreactor 160 shown in FIGS. 4A and 4B can include a bioreactor body 162 having multiple channels 163, each having a first channel 164 and a second channel 166 with a porous material or a membrane 168 at least partially therebetween. In some embodiments, the bioreactor body or substrate can include a first substrate and a second opposing substrate, each having a channel, such that when the first and second substrates are connected, the bioreactor body includes a first channel 164 and a second channel 166 aligned with the first channel and separated from the first channel by the porous material, as shown in the cross-sectional view of the bioreactor shown in FIG. 4B. The membrane 168 can be any material that includes pores such that it can selectively capture the biological substance in the first channel, and also provide microchannel to fluidly connect the first channel 164 and the second channel 168. In some embodiments, the bioreactor can further include a plurality of inlets (at least one inlet per channel) and a plurality of outlets (at least one outlet per channel). For example, in some embodiments the bioreactor can include a first inlet for providing a first fluid flow to the first channel, a second inlet for providing a second fluid flow to the second channel. The bioreactor can include a first outlet for permitting the first flow to exit the first channel and a second outlet for permitting the second now to exit the second channel. It will be understood, however, that any number of inlets and outlets can be provided for supplying or removing fluids or materials into and out of the channels and that additional conduits can also be formed in the substrates of a bioreactor.

In some embodiments, individual bioreactors, either having a single flow path or multiple flow paths, can be configured to operate in parallel or in series. For example, each bioreactor body (or multiple groups of bioreactor bodies) can be independently operated in parallel, wherein each bioreactor body or group of bioreactor bodies includes first and second pumps and first and second recirculation lines as described in more detail below. In some embodiments, for example, two or more of the bioreactor bodies can be connected in series such that, once seeded, a single pair of first and second pumps can be configured to provide flow through each of the series-connected bioreactor bodies. It will be appreciated that, in some embodiments, pump input flow rate can be independent of the number of bioreactor bodies in series, although larger reservoirs can be required to accommodate system volume.

Figure 5A:
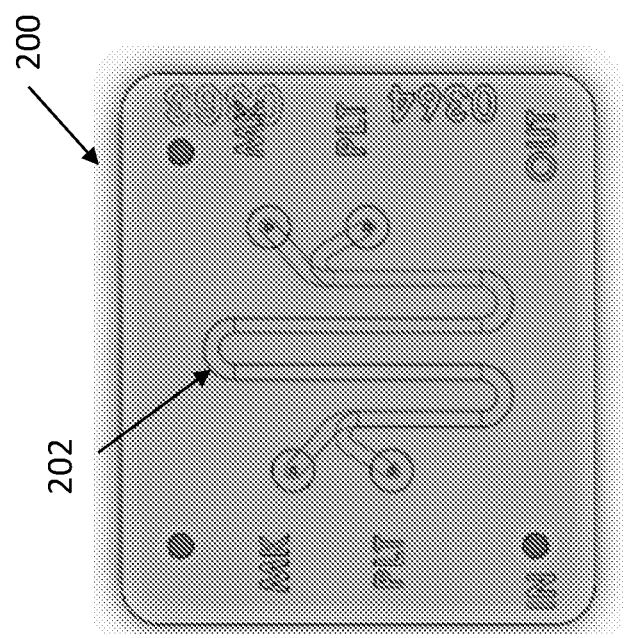
FIG. 5A illustrates an embodiment of single flow path bioreactor.
Figure 5C:
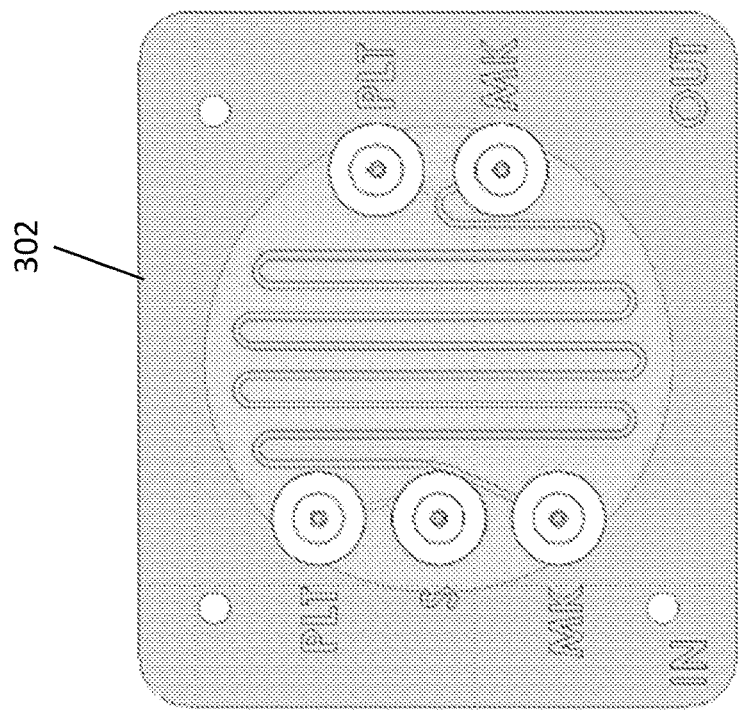
FIGS. 5B and 5C are perspective and top views showing an embodiment of a bioreactor, in accordance with various embodiments.
Figure 5B:
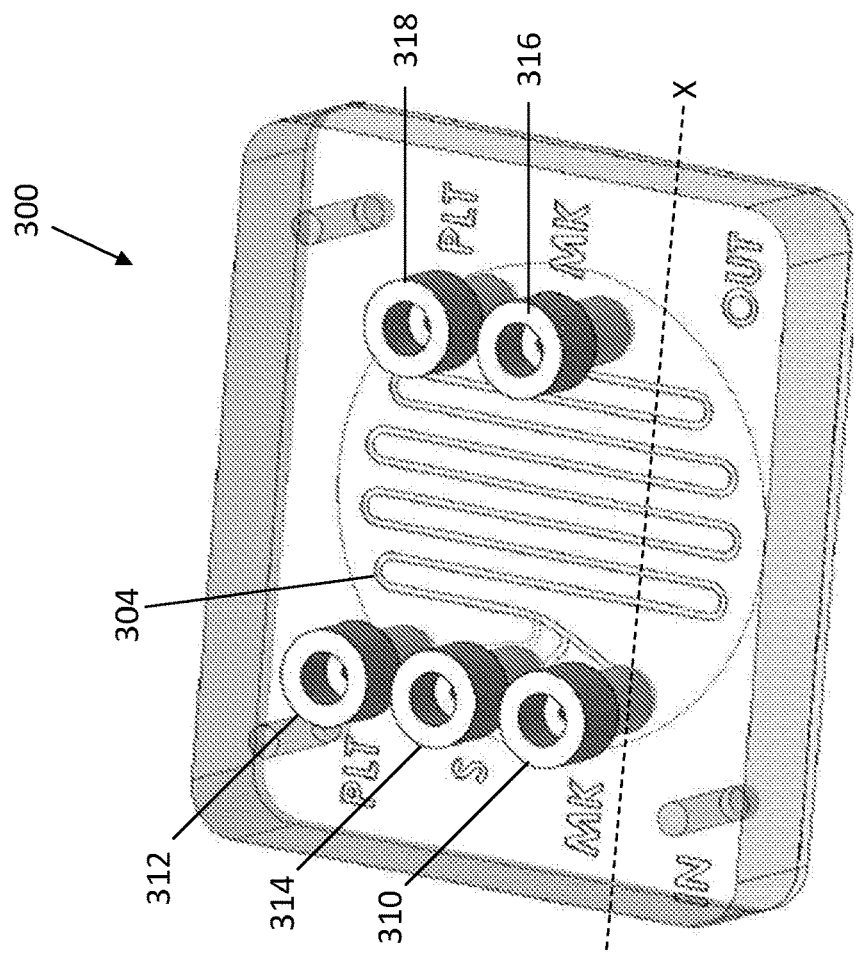

FIG. 5A illustrates an embodiment of a single flow 202 path bioreactor 200. Referring now to FIGS. 5B-5C, a single channel bioreactor similar to the one illustrated in FIG. 5A is shown. In some embodiments, the bioreactor 300 includes a bioreactor body 302 including a first channel 304, a second channel 306, and a membrane 308 arranged at least partially therebetween (as, for example, shown in FIG. 8B). In some embodiments, the first channel is positioned in a first substrate, and the second channel is positioned in an opposing second substrate. The bioreactor 300 can include a first inlet 310 for providing a first fluid flow to the first channel 304, a second inlet 312 for providing a second fluid flow to the second channel 306, and a third inlet 314 for introducing a biological source material into the first channel 304. As further shown in FIGS. 5B-5C, in some embodiments the bioreactor 300 can include a first outlet 316 for permitting the first flow to exit the first channel 304 and a second outlet 318 for permitting the second flow to exit the second channel 306. It will be apparent, however, that any number of inlets and outlets can be provided for supplying or removing fluids or materials into and out of the channels. In some embodiments, some of the inlets and outlets may be combined, such as, for example, shown 5A, the biological source material can be introduced through the first inlet. Optionally, in some embodiments, a perfusion channel can also be included in the bioreactor. In such embodiments, the perfusion channel can, for example, allow for the flow of a gas, which can subsequently perfuse through the substrate materials and into the first and second bioreactor channels. For example, in some embodiments, a gas mixture having about 5% $CO_2$ to about 10% $CO_2$ can be perfused into one or more of the channels to provide appropriate pH buffering. In some embodiments, a gas mixture having about 4% $O_2$ to about 20% $O_2$ can be perfused into one or more of the channels to provide appropriate oxygen content for cells with different metabolic needs. In some embodiments, a gas mixture including about 4% $O_2$ and about 10% $CO_2$ can be perfused into one or more of the channels and can be used for various cell differentiation applications. In some embodiments, a gas mixture including about 20% $O_2$ and about 5% $CO_2$ can be perfused into one or more of the channels and can be used for various cell growth applications. It will be understood that the inlets and outlets of the bioreactor can be positioned on the sides, top, or bottom of the bioreactor to facilitate a stacked configuration.

Figure 6A:
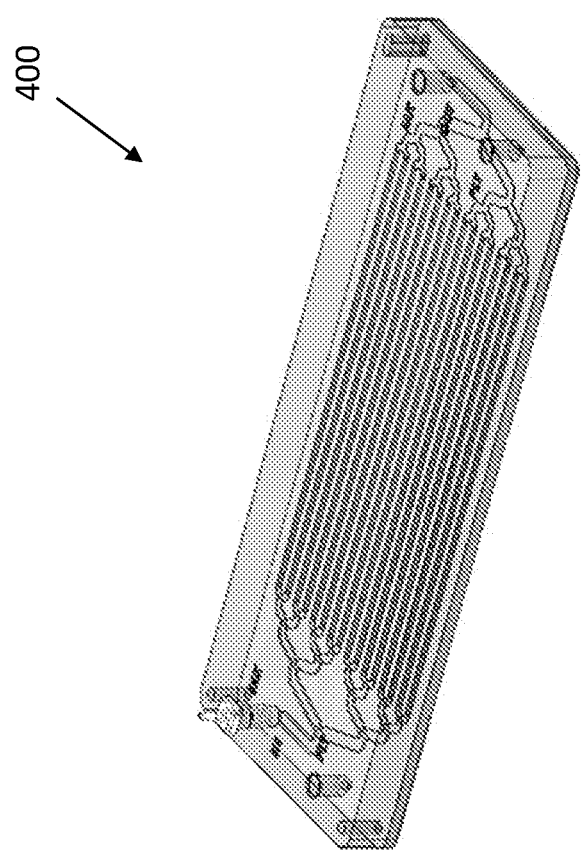
FIG. 6A illustrates an embodiment of a multiple flow path bioreactors.
Figure 6C:
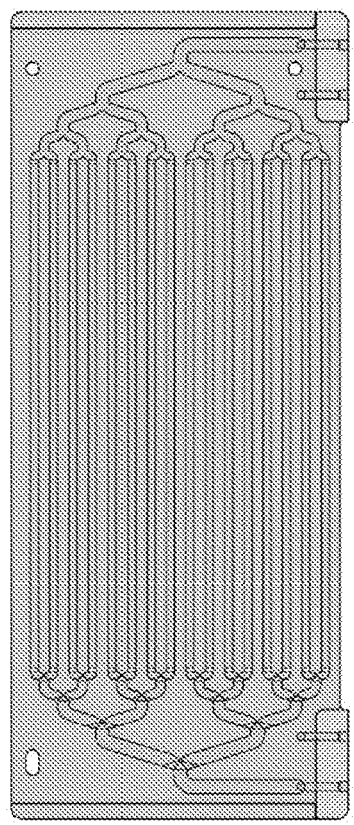
FIGS. 6B, 6C, 6D, 6E, 6F, 6G, and 6H illustrate various view of an embodiment of a 16-channel bioreactor.
Figure 6B:
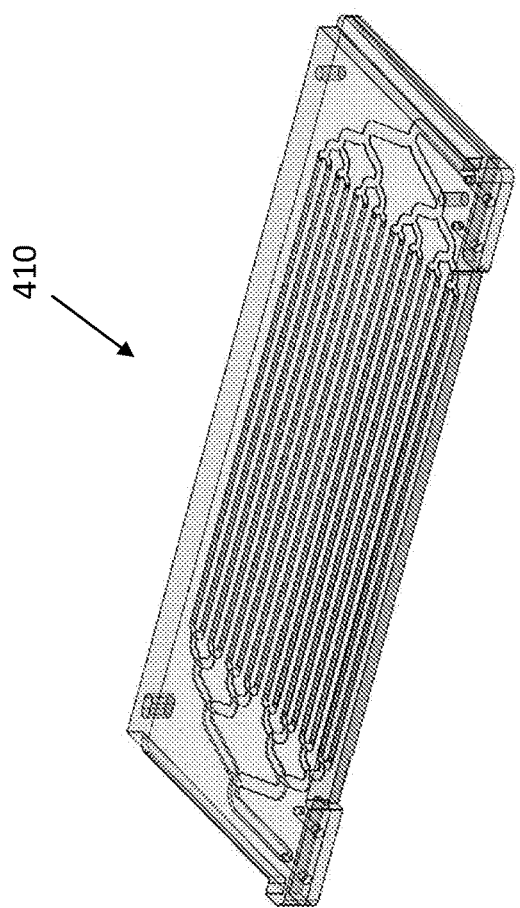

FIG. 6A illustrates an embodiment of a multiple flow path bioreactor 400 that can be used with a parallelization strategy to form a stacked platelet production bioreactor. The multiplexed bioreactor channels can be arranged in other configurations, such as radially aligned in a circular platform where multiple channels are fluidically connected or independently parallelized. It will be understood that a bioreactor can also be referred to as a blade.

In reference to FIGS. 6B-6H, in some embodiments, a plurality of multiple flow path bioreactors can be used together in a stacked configuration. For example, a bioreactor 410 having 16 channels can be employed. The multiple channels can have one inlet for each section of the channels that distributes flow to all channels, and one outlet for each section of the channel, which combines the output of all 16 channels. In some embodiments, each channel can have its own inlet and its own outlet. In some embodiments, the channels can have a common inlet and a different outlet or a common outlet and different inlets. The multiplexed devices can be stacked in any configuration, for example, in groups of eight devices. It will be understood that the number of stacked devices can vary. The inlets of the stacked devices can be connected fluidically to a main inlet for the top and bottom sections of the devices. Likewise, the outlets can be combined into a main outlet for each of the sections of the channel. For example, FIGS. 6B-6H illustrate a 16-plex device 410 with a single inlet for the first channels (tor example, the biological source composition), a single inlet for the second channels, a single outlet for all the first channels, and a single outlet for all the second channels.

Figure 6D:
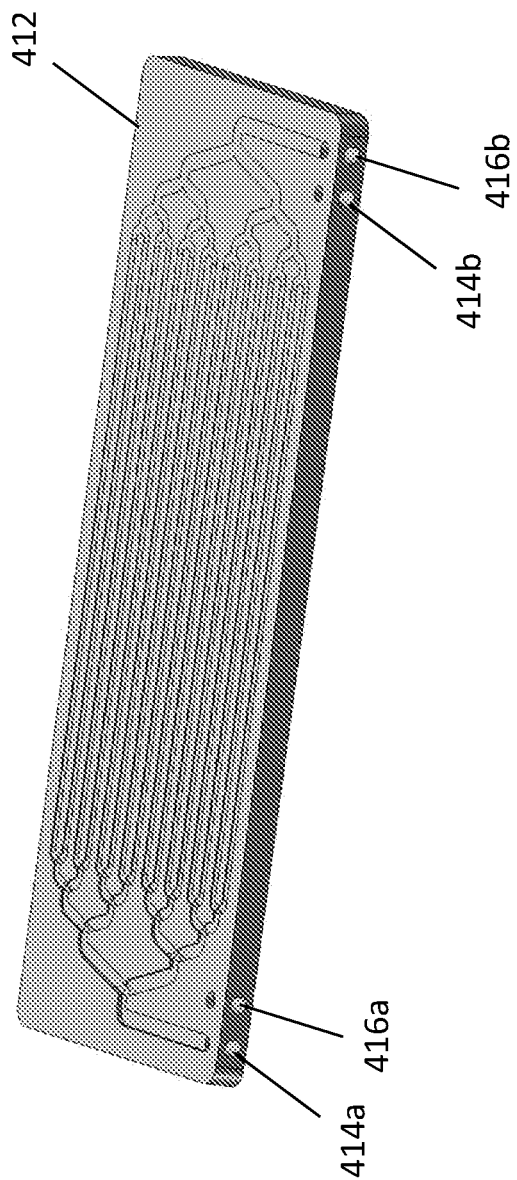
Figure 6E:
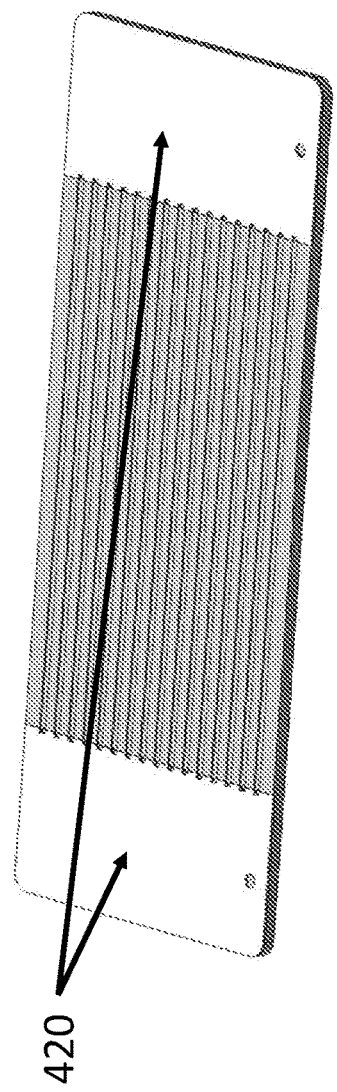
Figure 6F:
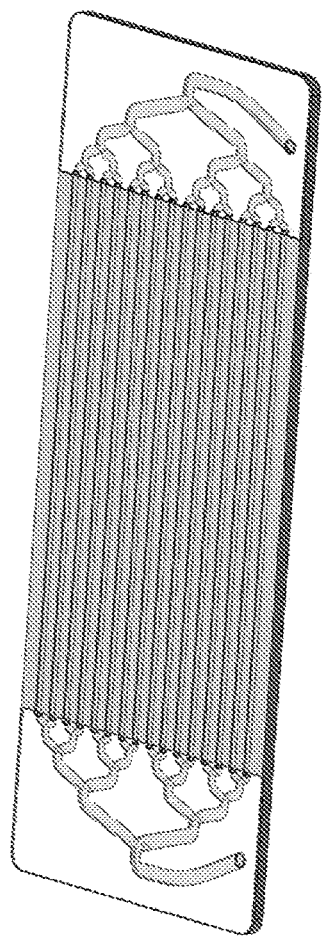
Figure 6G:
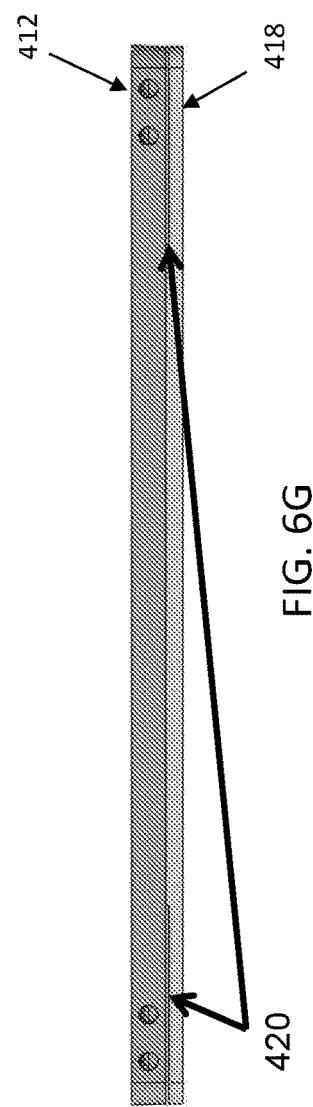
Figure 6H:
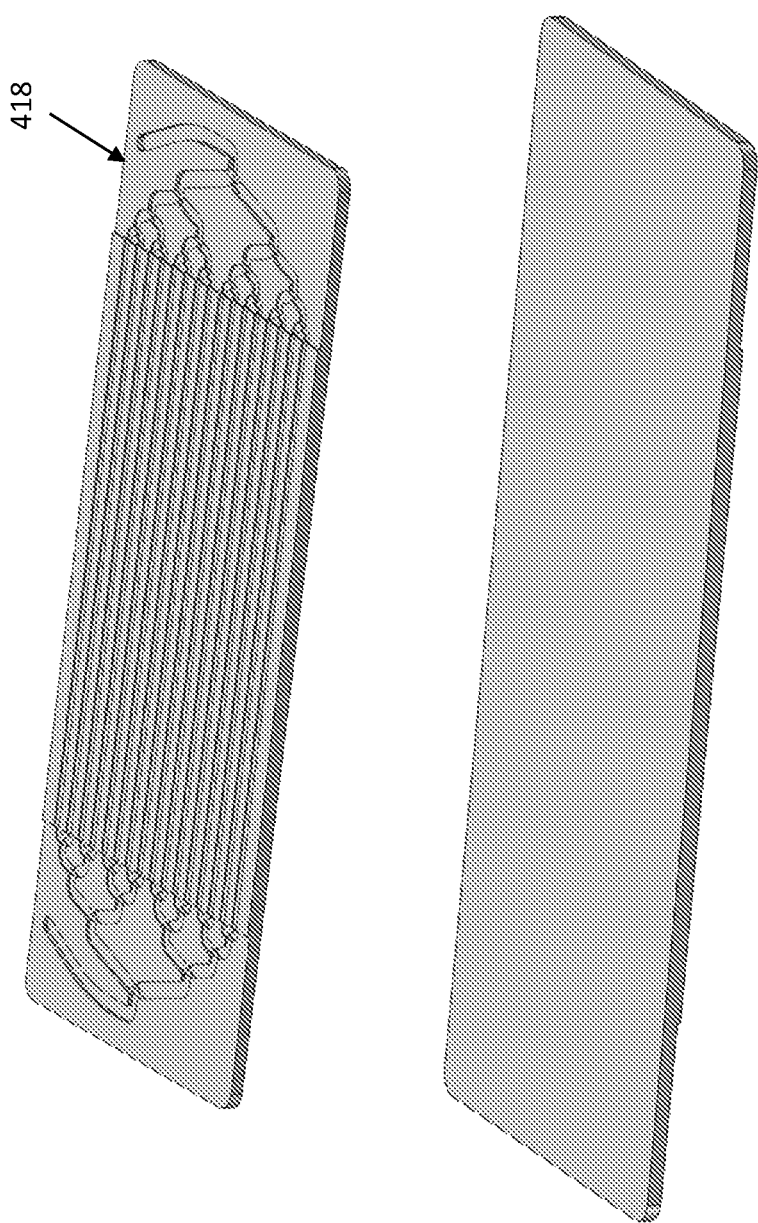

FIGS. 6B-6H illustrate various views of a stackable 16-channel bioreactor layer design. The layer inlets 414a, 416a and outlets 414b, 416b are located on the first channels side 412 to facilitate stacking of the bioreactors and connection of the inlets, as shown in FIG. 6D. The first channel inlet 414a and outlet 414b has a manifold that distributes the flow in and out to its 16 channels. The second channel inlet 416a and outlet 416b connect to the second channels side 418 through PET film 420, and into a manifold that distributes the flow to all 16 channels of the second channel side. The PET film 420 is positioned between the first channels side and the second channels sides, and the second channel manifold contacts the PET film that serves as a ceiling to the second channel manifold, and the first channel manifold contacts the same PET film, which serves as a floor to the first channel manifold.

In any of the various bioreactor embodiments described herein, the input materials that enter the inlets of the first channel can include cells and cell mixtures, cell culture media, buffer, protein solutions, and small molecule compounds. The components of such inputs which size is above the size of the membrane of the bioreactor will remain in the first channel, while those below that threshold will be allowed to pass to the second channel. The inputs of the second channel can include cell culture media, buffer, protein solutions, and small molecule compounds. The output of the first channel can include products of the input materials such as platelets or proteins, as well as the input materials such as cells and culture media. The output of the second channel can include products of the inputs from the first channel that are below the size of the membrane pores, as well as products from the inputs into the second channel, for example, platelets and proteins. For example, the first channel inlets can be the MK and S inlet, the first channel outlet can be the MK outlet, the second channel inlet can be the PLT inlet, and the second channel outlet can be the PLT outlet.

Figure 7:
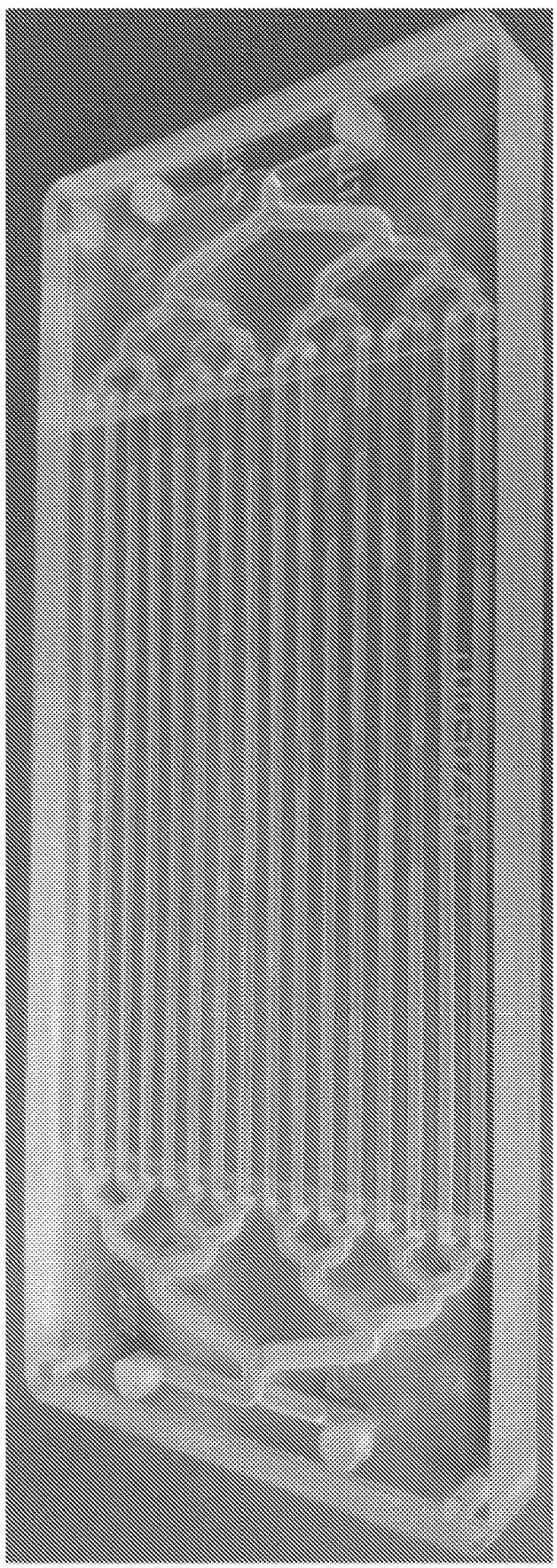
FIG. 7 is an exemplary image of perspective view of a 16-channel bioreactor.

FIG. 7 illustrates an embodiment of a multi-channel bioreactor. The bioreactor body or substrate, in some embodiments, can be of any suitable size, including, for example, having lateral dimensions in a range between 10 mm and 100 mm, and a thickness in a range between 1 and 10 mm, although other dimensions can be used in accordance with various embodiments. The substrates, in some embodiments can De manufactured using any combination of biocompatible materials, inert materials, as well as materials that can support pressurized gas and fluid flow, or gas diffusion, and provide structural support. In some aspects, materials utilized in the bioreactor can be compatible with specific manufacturing processes, such as insert casting. In addition, materials utilized can optically clear to allow visualization of fluid media, and other substances, present or flowing in various portions of the bioreactor. The substrates, in some embodiments, can be constructed of, for example, one or more of polymethyl methacrylate (PMMA), polydimethylsiloxane (PDMS), one or more polycarbonates (PC), cyclic olefin copolymer (COC), cyclic olefin polymer (COP), polyvinyl chloride (PVC), coated polystyrene, coated glass, polyurethane (PU), silicone elastomers, or combinations thereof. The substrates and channels, in accordance with various embodiments, can be constructed by one or more of machining flow channels into block base material, injection molding, casting, hot embossing, soft lithography, thermoforming, insert casting, or combinations thereof. The substrates can be assembled with the membrane therebetween, for example, by application of two pieces of laser cut pressure sensitive adhesive to adhere the substrates to each side of the membrane, mechanical clamping, solvent bonding, thermal bonding, diffusion bonding, laser welding, combinations thereof, or even manufactured in one piece through injection molding.

The channels formed in the bioreactor body can vary in length, size, and shape. In some embodiments, a length of each of the first and second channels can be in the range of about 10,000 to about 1,000,000 micrometers or, more particularly, in the range of about 25,000 to about 320,000 micrometers, while at least one transverse dimension of the each of the first and second channels can be in the range of about 100 to about 3,000 micrometers or, more particularly, in the range of about 500 to about 1,000 micrometers. However, it will be understood that first and second channels can be of any length or width in accordance with various embodiments. In some embodiments, the first and second channels can have identical length and transverse dimensions. In some embodiments, the first and second channels can have different widths and/or transverse dimensions. For example, in some embodiments, the first channel can be wider or narrower than the second channel. These geometrical modifications can be used to control the fluid dynamic properties of each channel independently. Furthermore, in some embodiments, as shown in FIGS. 8A-8B which illustrates a cross-sectional view of the bioreactor of FIG. 5B through line X, each channel 304, 306 can also be tapered either over the entire length of the serpentine pathway or over a portion of the length of the serpentine pathway to control shear rates or pressure differentials between the channels, over an active contact area, regulating perfusion through the membrane 308.

Various implementations of the bioreactor are possible depending upon specific uses or applications. For example, dimensions, shapes, and other features of various components of the bioreactor can be selected based on the desired output of the bioreactor. In particular, in some embodiments, the first and second channels, along with other fluidic elements of bioreactor, can be shaped and dimensioned to reproduce physiological conditions, such as, for example, those found in bone marrow and blood vessels. In some embodiments, channel shapes and dimensions can be selected to achieve physiological flow rates, shear rates, fluid pressures and/or pressure differentials similar to those associated with, for example, in vivo platelet production, as described with reference to FIG. 1.

Figure 8C:
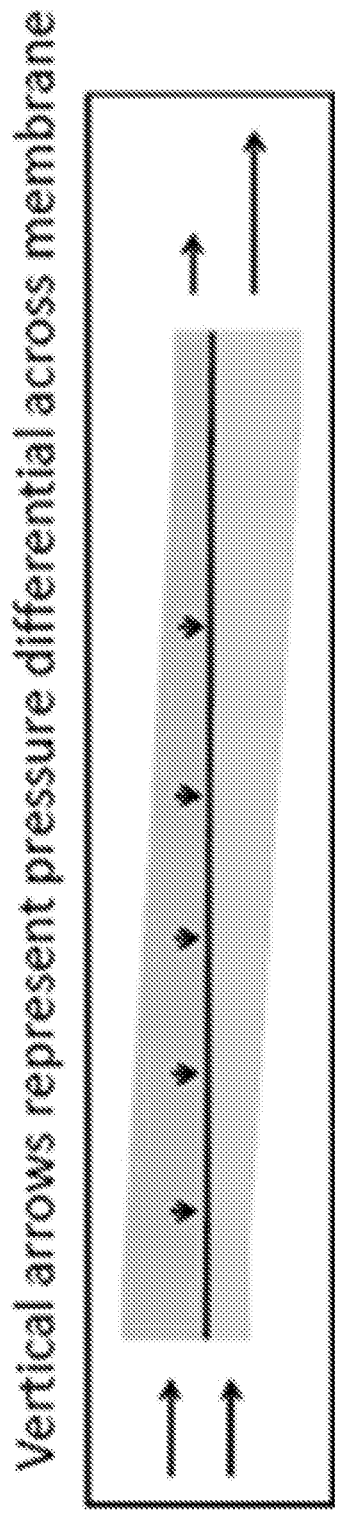
FIG. 8C is an embodiment of a cross-sectional side view of the bioreactor showing pressure drop across a membrane.

In reference to FIG. 8C, in some embodiments, the bioreactor can operate by having a pressure drop between the inlets and outlets that drives fluid from the inlets to the outlets. The geometry of the one or both of the channels can be adjusted to set the pressure differential across the membrane to be uniform throughout the entire channel. The geometry of the one or both channels can also be adjusted to achieve constant or near constant shear rates at the surface of the membrane in the second channel through the entire length of the device channels. For example, in a regime where the width (w) of the channel is much larger than its height (h), the shear rate at the membrane (1) can be held approximately constant across the length of the channel, where the volumetric flow rate (Q) is decreasing or increasing, by decreasing or increasing the height of the channel following the relationship:

$$\tau = \frac{6Q}{wh^2}$$

In some embodiments, the instant bioreactor can be configured such that the pressure and shear stress are decoupled and can vary independently of one another. In some embodiments, the instant bioreactor is designed such that the shear stress can be altered by changing the operating flow rate, while the transmembrane pressure associated with such flow rate change can be offset by decreasing the flow through the membrane, by, for example, modifying the number of cells occluding the membrane pores.

Alternatively, the shear rate can be increased by increasing flow rate, while pressure across the membrane can be kept constant by decreasing the cell seeding density. This can enable identification of appropriate regimes of biophysical parameters that allow for specific biological processes, such as platelet production.

In some embodiments, the first channel, the second channel, or both can be sized and shaped to ensure uniform seeding of the biological source material over the membrane. In some embodiments, such uniform seeding can be achieved by maintaining the near constant shear distribution along the membrane by the decreasing height of the channel, as well as maintaining a constant pressure differential across the membrane. This can be achieved on either side of the membrane by inverting the direction of the flow on both channels.

In some embodiments, the first and second channels terminate to create a single fluid conduit from the first inlet to the first outlet and from the second inlet to the second outlet, respectively, as shown, for example, in FIGS. 5B-5C. In some embodiments, fluid media introduced into the first inlet is extracted from the first outlet and fluid media introduced into the second inlet is extracted from the second outlet. In some embodiments, fluid media introduced into the first and second inlets can be extracted from the second outlet, and the first outlet can remain closed during operation of the device. However, it will be appreciated in view of this disclosure that additional inlets and outlets can also be possible with the bioreactor and connected to the first and second channels or any additional channels through the substrate (e.g., the third inlet as shown in FIGS. 5B-5C). Additional inlets can be used to introduce different biological materials. Additional outlets can be used to, for example, fractionate the outcome of biological products, either uniformly or making use of differences in intrinsic properties of the products affecting their positioning in the channels.

The membrane between the first channel and the second channel can be formed in a variety of ways. In some embodiments, the membrane can be made of any porous material, include any rigid or flexible layer, film, mesh or material structure configured to connect corresponding first channel and second channel via fluidic pathways formed therein. In some embodiments, the membrane can be formed from any suitable material including, for example, Polycarbonate Track Etch-Polyvinylpyrrolidone Free (PCTEF), Polycarbonate Track Etch-PVP Coated (PCTE), hydrophilic polycarbonates, hydrophobic polycarbonates, polyvinyl chloride (PVC), polyester, cellulose acetate, polypropylene, PTFE, polyurethane (PU), silicone elastomers, or combinations thereof. In some embodiments, fluidic pathways in the membrane can be formed using pores, gaps or microchannels, distributed with any density, either periodically or aperiodically, about the membrane. In some embodiments, the membrane can include a three-dimensional structure formed using interwoven micro- or nano-fibers arranged to allow fluid therethrough. In some embodiments, the membrane may be a 2-dimensional material such as a film or a sheet of porous material. In some embodiments, the membrane may be formed integrally with the bioreactor body by forming a plurality of fluidic pathways in the bioreactor between the first and second channels. Although shown in FIGS. 5B-5C and 8A-8B as rectangular in shape, it can be appreciated that the membrane can have any shape, including circular shapes, oval shapes, and so forth. In accordance with aspects of the disclosure, the membrane can be configured to selectively capture specific biological source materials or substances to produce desired biological products. For instance, when producing platelets from megakaryocytes, the membrane may be configured to selectively capture megakaryocytes and allow the captured megakaryocytes to extend proplatelet extensions through the membrane and to release platelets into the second channel.

In some embodiments, the membrane can be flexible to more closely mimic pulsatile blood flow within a patient. In such embodiments, as shown in FIGS. 9A-9B, the membrane can transition between a substantially planar resting position during a resting pulse, as shown in FIG. 9A, and a stretched configuration during a pressure pulse, as shown in FIG. 9B. The membrane can be made of a flexible material, or a material that can allow the membrane to stretch or curve under pressure. In some embodiments, this may further assist in adjusting the pressure through the membrane, while avoiding damaging the biological source material that can be distributed on the surface of the membrane or inside the membrane.

In some embodiments, the channels can be designed so the optimum fluidic conditions are created with respect to pressure drop across the membrane and shear on the surface of the membrane in the second channel when equal flows are introduced to the first channel inlet and the second channel inlet. This can be achieved by operating the bioreactor with the first (upper) channel outlet closed, and by varying the channels cross-sectional area along their length to constrain the shear rate on the second (lower) channel.

Figure 8D:
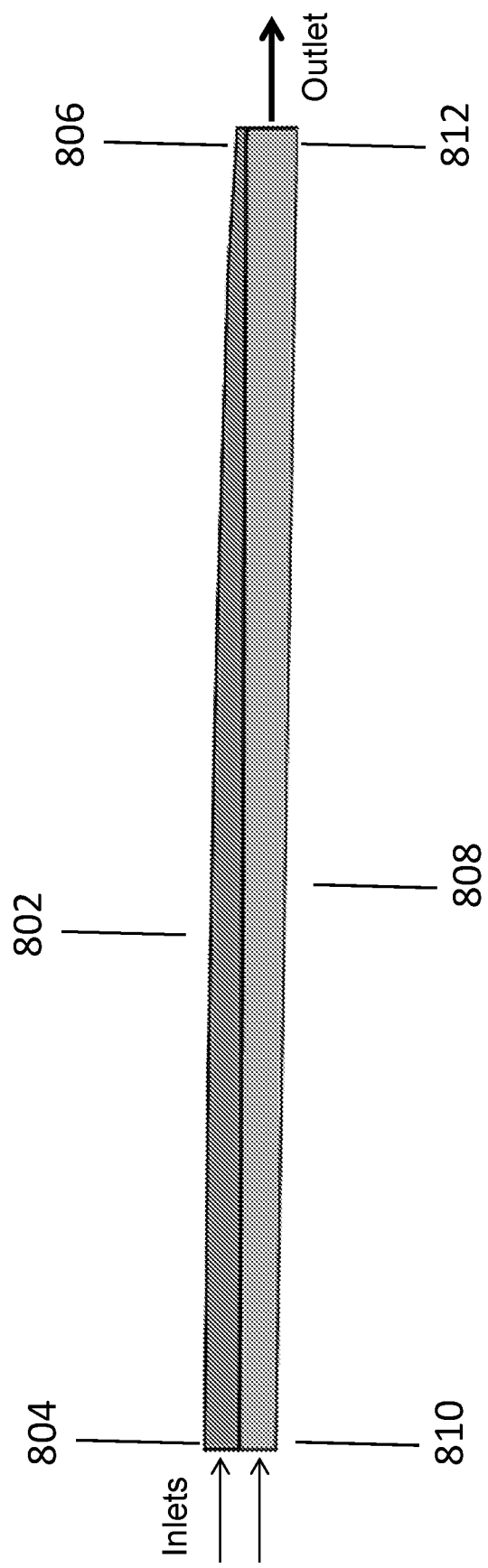
FIG. 8D illustrates a cross sectional view of a first and second channel.

In some embodiments, such fluid conditions include, for example, a constant pressure drop across the membrane per unit area of the membrane. In this manner, the flow rate through the membrane may also be constant along the membrane. As shown in FIG. 8D, in some embodiments, the cross-sectional area of the first channel 802 may decrease from the inlet 804 toward the opposing end 806 of the first channel. In some embodiment, the cross-sectional area of the second channel 808 may increase from the second inlet 810 toward the second outlet 812. The change in the cross-section can occur over a portion of the channel or for the entire length of the channel. In some embodiments, the profile of the change of the cross-sectional area may depend on the channel size, the channel shape, the desired flow rate through the membrane, the desired pressure drop across the membrane, the desired pressure drop across the bioreactor, the size of the biological material, or a similar operating parameter. In some embodiments, the change in the cross-sectional area may be non-linear. In some embodiments, the change in the cross-sectional area may be linear. In some embodiments, the size and shape of the channels may be selected such that the pressure differential across the membrane can be uniform over the surface of the membrane in the first channel or the second channel and the shear rate of the fluid on the membrane surface in the first channel or the second channel can be uniform across the surface.

In some embodiments, the length of the channels can be between about 30 mm and about 300 mm in length. In some embodiments, the length of the channels can be between about 100 mm and about 150 mm in length. In some embodiments, the channels may have a substantially similar height at the inlet and a different height at the outlet, with the first channel having a smaller height at the outlet. In some embodiments, the inlet height can be between about 100 microns to about 3 mm. In some embodiments, the inlet height can be between about 0.1 mm to about 0.5 mm. In some embodiments, the outlet height in the second channel can be between about 200 microns to about 6 mm. In some embodiments, the outlet height in the second channel can be between about 0.3 mm to about 0.8 mm. The height of the first channel decreases towards the outlet, but is limited by the size of the biological source material, and is also preferably sized to allow air bubbles to vent out of the first channel. In some embodiments, the width of the channels can be between about 0.5 mm to about 5 mm. In some embodiments, the width of the channels can be between about 0.5 mm to about 5 mm. In some embodiments, the width of the channels can be between about 1.5 mm to about 4 mm.

In some embodiments, the pressure differential across the membrane can be uniform over the surface of the membrane and the shear rate of the fluid on the membrane surface in the first channel or the second channel can be uniform across the surface. In some embodiments, the volumetric flow rate of the first channel can be substantially equal to the volumetric flow rate of the second channel. In this embodiment the biological source material experience drag force at the surface of the membrane facing the second channel caused by a uniform shear field.

In some embodiments, a single peristaltic pump head can be used to pump fluid to both inlets. In this way, the variability in the peristaltic pump volumetric flow rate will be synchronized between the top and bottom channels. This condition will create a variable but always positive pressure on the membrane when moving from the first to the second channel. The positive pressure allows the source biological material to come to rest on pores in the membrane and never become dislodged by negative pressure across the membrane even if the volumetric flow rate varies with the phase of the pump head or the rotation speed of the pump head is adjusted.

The dimensions of the membrane are also variable. In some embodiments, the membrane can include longitudinal and transverse dimensions in a range between about 1 and about 100 millimeters, and have a thickness in a range between about 0.1 to about 20 micrometers, although other dimensions are possible. Also, the membrane can include pores, gaps or microchannels sized in a range between about 1 micrometers and about 20 micrometers, for example, about 5 to about 8 micrometers. In some embodiments, pore, gap or microchannel size, number, and density can depend on a number of factors, including but not limited to desired biological products and product yields, as well as flow impedances, shear rates, pressure differentials, fluid now rates, and other operational parameters. In some embodiments, the membrane can include pores, gaps, or microchannels in a density of about 500 to about 10,000 pores per $mm^2$.

As will be appreciated, the opposing first and second channels are in overlapping alignment to define an active contact area in the membrane. For example, an active contact area may be in a range between about 1 $mm^2$ to about 250 $mm^2$, although other active areas are possible, depending upon the dimensions and number of channels utilized. In some implementations, the active contact area along with membrane characteristics can be optimized to obtain a desired biological product yield. For example, a membrane with 47 mm diameter, 5% active contact area, and pore density of about 1-105 pores/$cm^2$ could provide about 200,000 potential sites for generating a desired biological product yield, such as a desired platelet yield. In some applications, the active contact area can be configured to trap at least about 1-104 megakaryocytes.

The substrates and membrane can be manufactured by a number of different processes. By way of example, the first substrate, or second substrate, or both, or portions thereof, can be manufactured using cell-inert silicon-based organic polymer materials, such as polydimethylsiloxane ("PDMS"), thermoplastic materials, such as polycarbonate (PC), cyclo olefin polymer ("COP"), glass, acrylics, and so forth. On the other hand, the membrane 116 can be manufactured using PDMS, thermoplastics, silk, hydrogels, extracellular matrix proteins, polycarbonate materials, polyesthersulfone materials, polyvinyl chloride materials, polyethyleneterephthalat materials, polyurethane (PU), silicone elastomers, and other synthetic or organic materials. Additionally, the bioreactor can be manufactured as one piece and as a series of bioreactors, through processes such as injection molding.

In some embodiments, the bioreactor can be functionalized to replicate in vivo physiological conditions in order to produce biological products such as, for example, platelets. For example, various substances can be introduced onto a surface of the membrane or into one or more of the channels to affect the reactions within the bioreactor. In some embodiments, a top surface of the membrane can be selectively coated with extracellular matrix proteins or functional peptides or other molecules, for example, while a bottom surface can be left without, or can be coated with different proteins or substances. In some embodiments, one or both channels can be filled with a hydrogel trapping cells and other materials in a 3D matrix. Selective perfusion or media in one channel wherein the second channel contains a hydrogel can, for example, create a concentration gradient in the gel that can be used to direct cell migration or differentiation or study small molecule, cytokine, growth factor diffusion.

Such coatings can be achieved, for instance, by infusing a first fluid medium containing extracellular matrix proteins, using inputs and outputs in the first substrate. At substantially the same time, a second fluid medium flow can be maintained in the second substrate using respective inputs and outputs, where the second fluid medium can either contain no proteins, or different proteins or substances. In some embodiments, flow rates of the first and second fluid media can be configured such that little to no fluid mixing would occur. Such selective functionalization can ensure that introduced platelet-producing cells, for example, coming to rest on the top surface can contact extracellular matrix proteins, while proplatelets extend through the membrane, and platelets released therefrom, would not contact extracellular matrix proteins, or would contact different proteins or biological substances. In some embodiments, the membrane can instead be pre-coated before assembly within the bioreactor.

Non-limiting examples of biological substances and materials for functionalizing the bioreactor can include human and non-human cells, such as megakaryocytes, endothelial cells, bone marrow cells, osteoblasts, fibroblasts, stem cells, blood cells, mesenchymal cells, lung cells and cells comprising basement membranes. Other examples can include small molecules, such as CCL5, CXCL12, CXCL10, SDF-1, FGF-4, VEGF, Flt-3, IL6, 9, 3, 1b, TPO, S1PR1, RGDS, Methylcellulose. Yet other examples can include, extracellular matrix proteins, such as bovine serum albumin, collagen type I, collagen type IV, fibronectin, fibrinogen, laminin, vitronectin (PLL), or any peptide sequences derived from these molecules. In particular, to replicate three-dimensional extracellular matrix organization and physiological bone marrow stiffness, cells can be infused in a hydrogel solution, which may subsequently be polymerized. The hydrogel solution may include, but is not limited to alginate, matrigel, agarose, collagen gel, fibrin/fibrinogen gel, and synthetic gels such as polyethylene glycol gels.

Various mechanisms can be used to stack a plurality of bioreactors. In some embodiments, a manifold can be used to fluidically connect a plurality of bioreactors. It will be understood that the manifold can be configured to hold any number of bioreactors having any number of channels. The manifold can be designed to provide equal flow rate to each device by having equal pressure drop through each inlet manifold, device and outlet manifold. This means that regardless of the path the fluid takes through the assembly it will have equal pressure drop given an equal volumetric flow rate. The pressure drop though each of the paths can be modelled by combining Bernoulli's equation $$P_1 + \frac{1}{2}\rho v_1^2 + \rho g h_1 = P_2 + \frac{1}{2}\rho v_2^2 + \rho g h_2$$

and Poiseuille's Law $$P_1 - P_2 = QR$$

where P is pressure, ρ is density, v is fluid velocity, g is gravity, h is fluid height, Q is volumetric flow rate, and R is resistance to flow. In some embodiments, such as for example, due to low velocities, or changes in pressures differentials due to gravimetric head canceling in the inlet and outlet manifold, the Poiseuille's Law equation may be used by itself.

FIGS. 10A-10D illustrates an embodiment of a manifold 500 for stacking of multiplexed devices. The height and cross-sectional area through the manifold are designed to ensure equal pressure at each inlet. Specifically, while fixing the inlets flow rates, the cross-sectional area gradually decreases to yield an average fluid velocity that forces a constant pressure for the decreasing flow rate for each stack of bioreactors at each of their respective heights within the stack. The geometry at the outlets section of the manifold is the reversed version of the inlets section to create equal pressure across each of the reactors. In some embodiments, Poiseulle's law can be used to account for the hydraulic resistance effect on pressure drop, being more critical for seeding large numbers of reactors, with longer manifold channels.

Figure 10C:
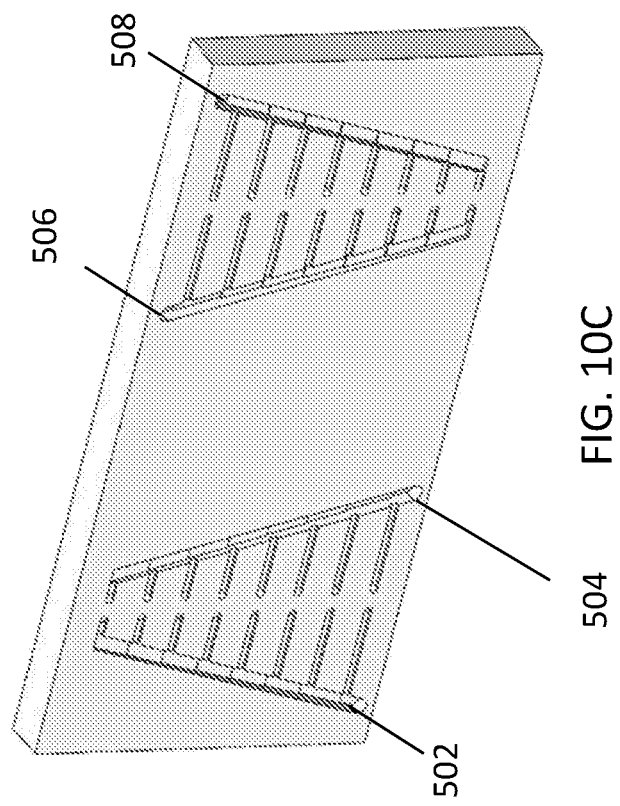
FIGS. 10A, 10B, and 10C illustrate side and perspective views of an embodiment of a manifold for stacking and fluidically connecting a plurality of bioreactors.
Figure 10A:
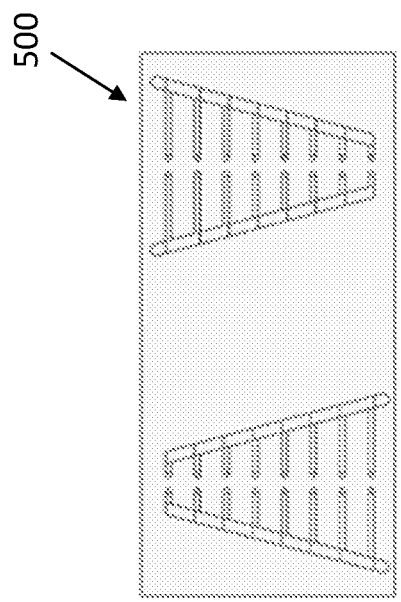
Figure 10B:
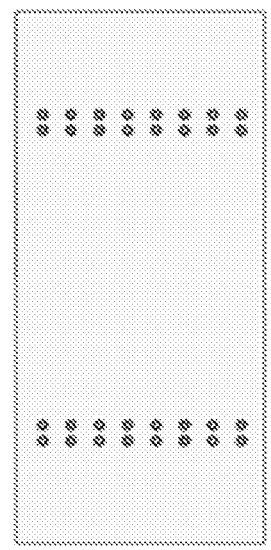

FIG. 10C illustrates the cross-sectional area of a manifold 500 designed to connect 8 bioreactors. Two main inlets 502, 504 distribute flow to 8 individual reactors, multiplexed or not, in which each of the reactors has an inlet for the first channel (a top side of the membrane) and the second channel (a bottom side of the membrane). Two main outlets 506, 508 collect outflow from each independent reactor's outlets. The reactors can operate with both outlets open, or with only one outlet open, forcing some or all the flow from one of the channels through the membrane and into the other section of the channel.

Figure 10D:
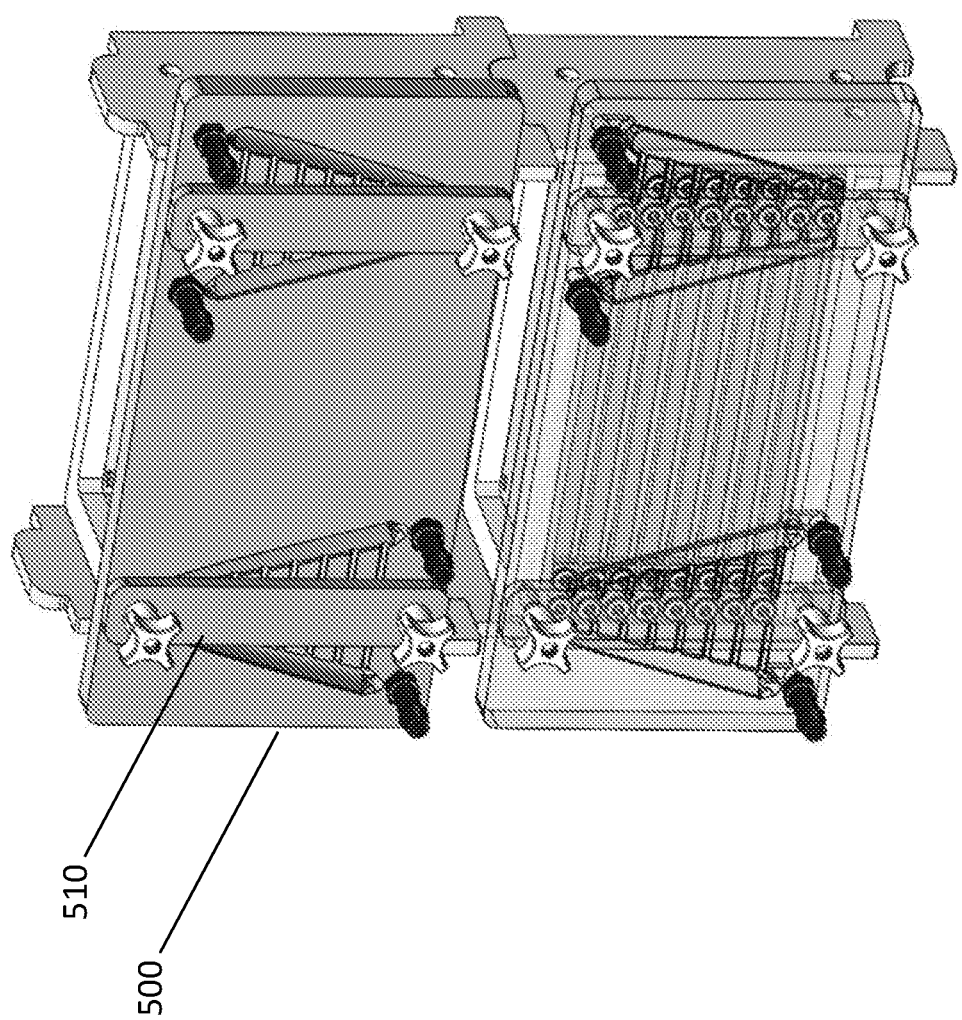
FIG. 10D illustrates an embodiment of a manifold including a plurality of bioreactors stacked within a frame that holds the bioreactors and the manifold together.

FIG. 10D illustrates 8 multiplexed devices with a support clamp 510, fluidically connected through the side manifold 500. Seals between the main manifold and the bioreactors can be formed using a variety of devices, including through o-rings. The o-rings are sandwiched between the manifold and the reactors and pressure between them can be applied through different methods, including solid bars that can be screwed in tight against the reactors and manifold, as shown in FIG. 10D. The manifold inlets and outlets align with the reactors inlets and outlets, with o-rings pressing between them.

Figures 11A, 11B:
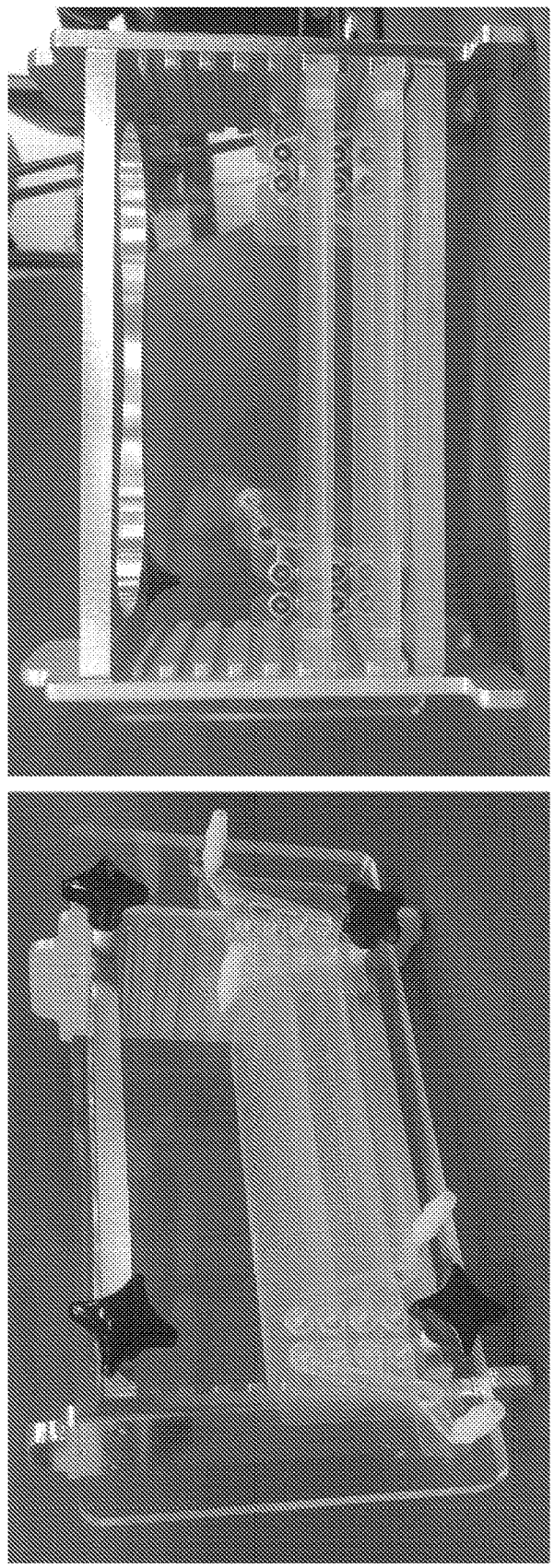
FIGS. 11A and 11B are images of an embodiment of a manifold for stacking and fluidically connecting a plurality of bioreactors.

FIGS. 11A and 11B illustrate a functional prototype with a manifold built to fluidically connect 4 multiplexed bioreactors, with two the bioreactor slots occupied by 16-channel bioreactors. In some embodiments, all of the bioreactors connected by a manifold can be similar. The flow rate is controlled at the inlets, but if each reactor is different (and therefore presents different resistance to flow), the flow rate can distribute unevenly. For example, 8 16-channel reactors can be stacked, or 5-channel reactors can be stacked. That said, if there was a specific configuration one would like to have, like 4 5-channel reactors on the bottom and 4 5-channel reactors on the top, the manifold could be designed to accommodate various configurations of bioreactors. In some embodiments, all slots can be occupied, or at least occupied by a mock device that presents the same resistance, to allow for equal distribution. Thus, in some embodiments, the manifolds can be used with all slots occupied by bioreactors that have equivalent hydraulic resistance.

In some embodiments, a bioreactor can also include features to facilitate the stacking of a plurality of bioreactors. In some embodiments as shown in FIGS. 12A-12C, a bioreactor 600 can include adaptations to allow sliding of devices into a main frame or a manifold. As seen in the perspective view of an embodiment of a bioreactor 600 shown in FIG. 12A and the top view of the bioreactor 600 shown in FIG. 12B, one or more sliding features 602 on the sides of a bioreactor can allow for facile insertion and removal from frame. As shown in FIGS. 12A and 12B, the bioreactor includes first and second sliding features 602, 604 on opposed sides of the bioreactor. As shown in FIG. 12B, a cutback 606 on the front of the device can counteract the sealing force required without compressing the body of the reactor therefor mitigating the possibility that the reactor will buckle or warp when sealed to the manifold. The cutback 606 can ensure that the manifold plate only makes contact with sealing faces of the bioreactor. This design allows increased pressure between the devices and the main manifold which reduces the risk for leaking and improve sealing. In addition, the location of the inlet and outlet on the side of the bioreactor 600, as shown in FIG. 12C, allows for ease in fluidically connecting a plurality of bioreactors when stacked using a manifold or other device.

Bioreactors can also be designed to include a means for fluid distribution between the layers that is created by the layers themselves. For example, FIG. 13A-13G illustrate a configuration of a block bioreactor where a multiplicity of bioreactors are combined together to form a liquid tight bioreactor block that includes multiple flow channels (such as, for example, straight circular flow bore) that fluidly connect to the channels of each bioreactor in the stack. As shown in the FIGS. 13A and 13B, such bores 706 can be formed at opposing ends of each bioreactor 702, such that when the bioreactors are stacked into a stacked bioreactor 700, the bores 706 are aligned to form a flow channel extending through the entire stacked bioreactor in fluid communication with the channels of the individual bioreactors in the stacked bioreactor 700.

Figures 13A, 13B:
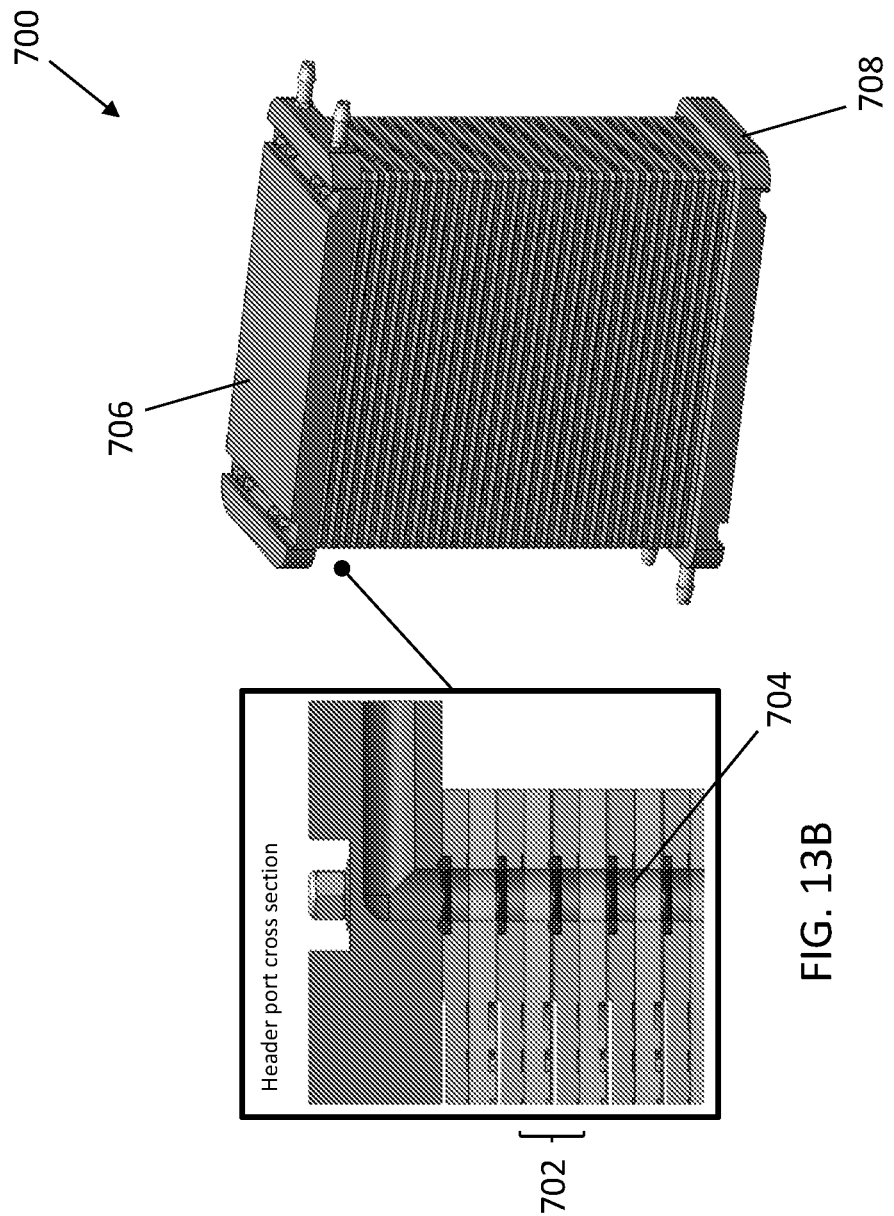
Figures 13C, 13D:
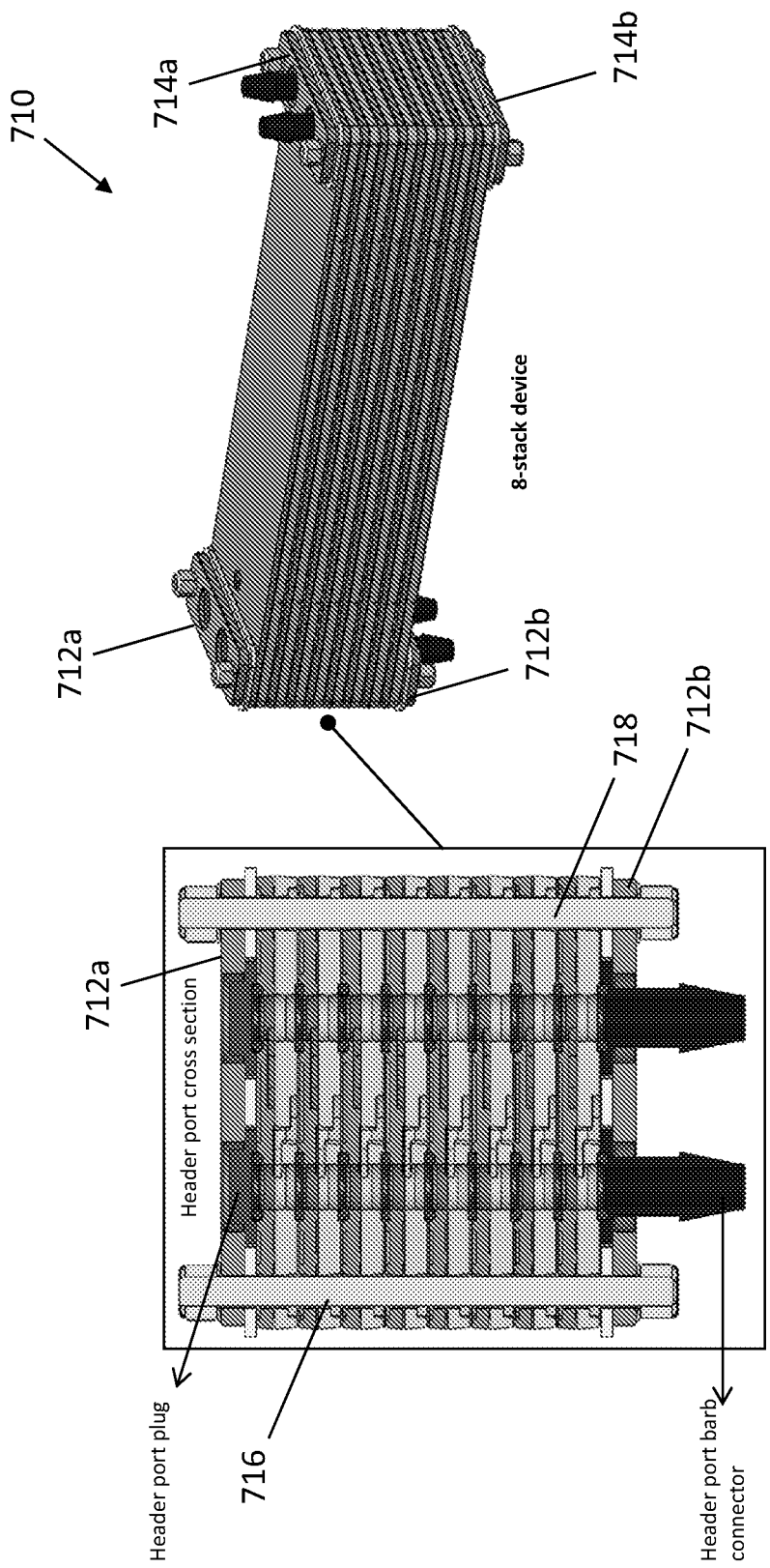
Figure 13E:
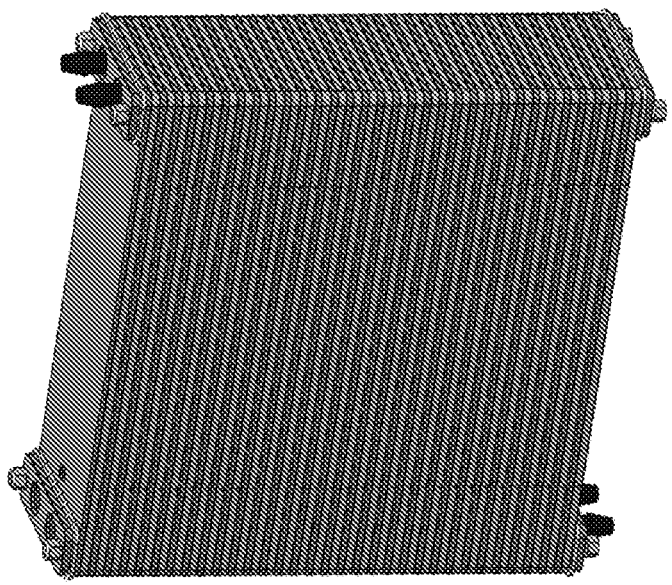

The stacked bioreactors can include an endplate to help provide structure to the stacked bioreactor. As shown in FIG. 13A, the endplate 706, can extend along the entire top and bottom surface of the stacked bioreactor 700. As shown in FIGS. 13C and 13D, two opposed headers can be positioned to extend along an outside edge of the top and bottom surfaces of the stacked bioreactor 710 and can include one or more compression rods, such as compression rod 716, coupled to the upper and lower endplates 712a, 712b, coupled to the upper and lower header on each opposed side of the bioreactor to provide compression to the stacked bioreactor 710. The compression rods can provide sealing force between the bioreactors on the O-rings 718 to create a fluidic seal between the bioreactors in the stack. This arrangement can be used with a variety of stacked bioreactors, such as a 8-stack device shown in FIG. 13C and a 32-stack device shown in FIG. 13E.

In reference to FIGS. 13F-13H, as discussed above, in some embodiments, the flow channels are designed so that the pressure drop at each of the bioreactor is substantially the same, which also provides a substantially equal flow through each reactor. In some embodiments, one or more of the flow channels can be modified to ensure such equal pressure drop through the bioreactors. For example, in some embodiments, as shown in FIG. 13H, the flow channel can include an insert 720 that decreases the open area of the flow channel from the inlet toward the end of the channel for the flow channels that feed the bioreactors and toward the inlet for the flow channels that drain the bioreactors. In some embodiments, the flow channels can be shaped to decrease in diameter from the inlet toward the end of the channel for the flow channels that feed the bioreactors and toward the inlet for the flow channels that drain the bioreactors. In this way, the equal pressure drop across and flow through each of the bioreactor in the stacked bioreactor can be maintained.

Figure 14A:
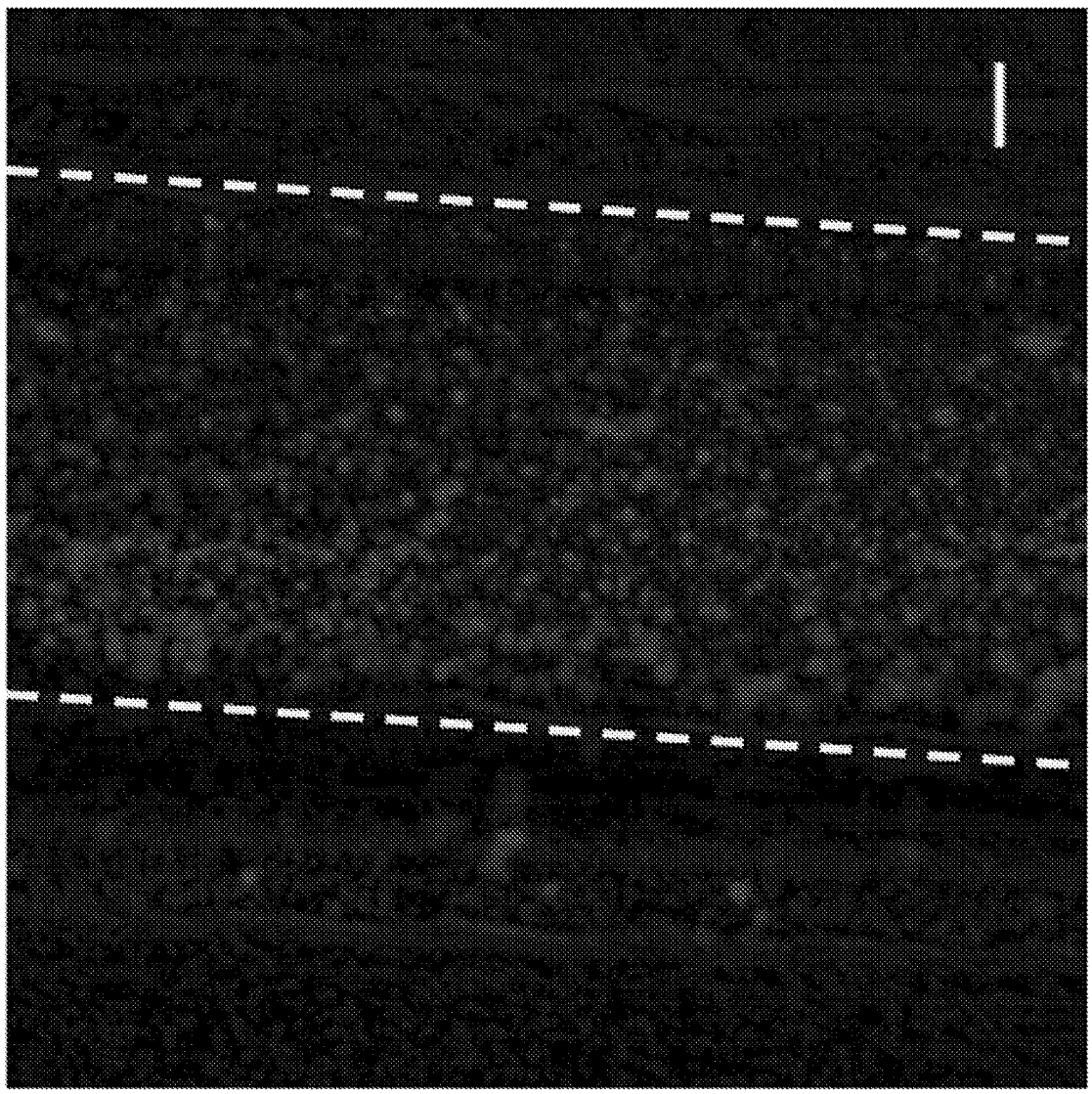
FIG. 14A is an image showing megakaryocyte distribution along a section of a bioreactor channel in accordance with various embodiments.
Figure 14B:
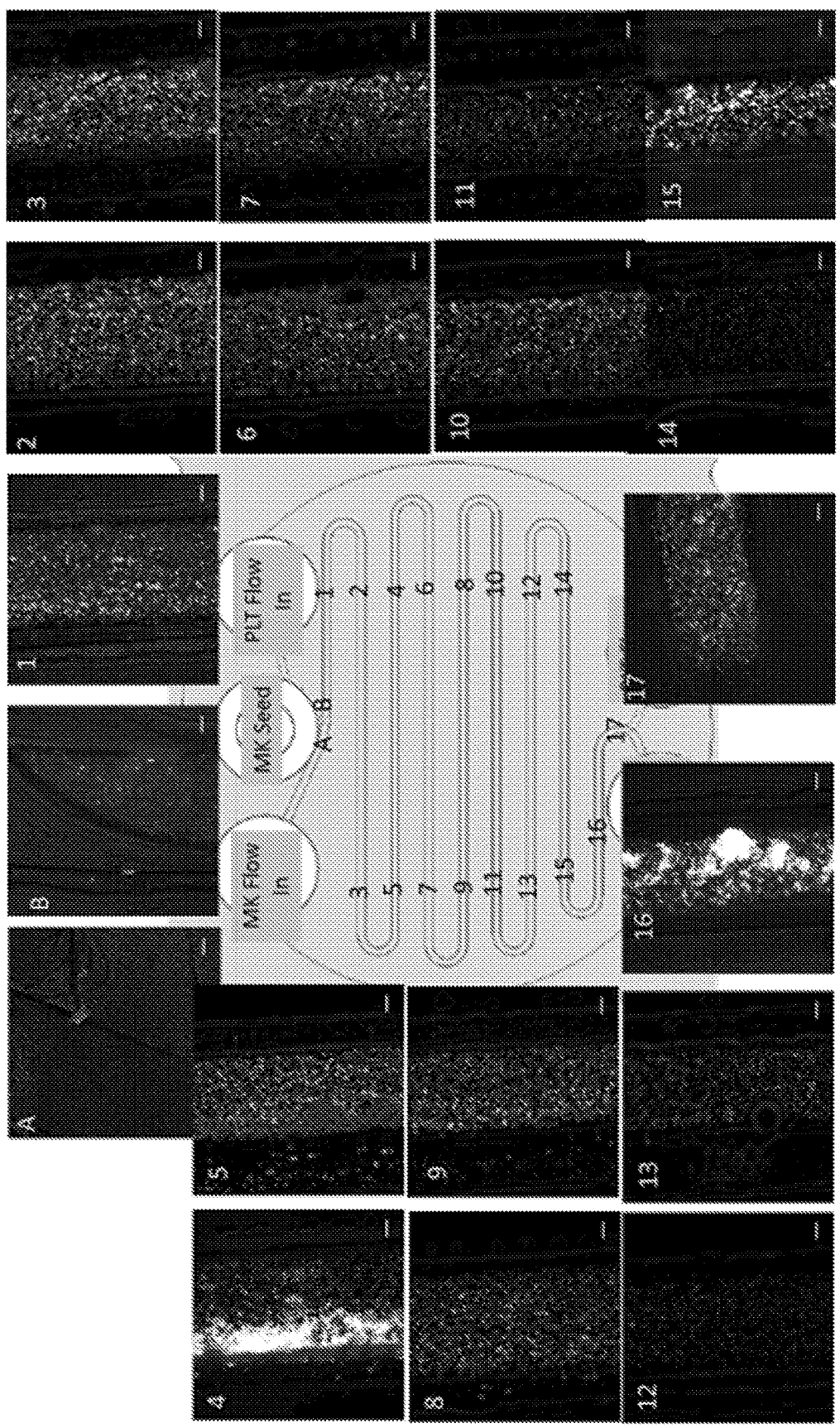
FIG. 14B is an image showing megakaryocyte distribution at various stations along a bioreactor channel in accordance with various embodiments.

During the seeding phase of reactor use, biological source material is introduced to the first channel and is deposited on or captured by the membrane. The distribution of the biological material is a function of how the biological material is introduced to the reactor, how it moves through the reactor and the distribution of flow through the membrane. More specifically the introduction of the biological source material onto specific streamlines on the laminar flow in the membrane, the settling or floating properties of the source material causing the material to move between laminar streamlines and the volumetric flow rate per unit area of the membrane In some embodiments, the biological source material is introduced in a well dispersed fluidic slug that places an equal quantity of source material on each streamline when entering the reactor, the flow rate is sufficient to move this material along the laminar streamlines without significant floating or settling so it stays on the streamline that it was introduced on, as it flows to the membrane and the membrane has a uniform volumetric flow rate per unit area creating a uniform density of biological source material across the surface of the membrane The bioreactors as described herein can provide a uniform seeding of the membrane with biological source material along the length of the first channel. For example, FIG. 14A is an exemplary image showing megakaryocyte distribution along a section of a bioreactor channel in accordance with various embodiments. As shown, rather than clustering in one specific localized area, the megakaryocytes are substantially uniformly distributed across and along the membrane. FIG. 14B illustrates exemplary megakaryocyte distribution at various stations along a bioreactor channel in accordance with various embodiments. As shown in FIG. 14I, rather tan clustering in one specific localized area, the megakaryocytes are substantially uniformly distributed across and along the membrane at each station but also substantially uniformly distributed between each of the stations along the length of the bioreactor channel. Such uniform distributions of seeded biological source material can be achieved in a plurality of ways, including, for example, one or more of the methodologies described below with reference to FIGS. 20, 21A-21B, and 22.

Figure 15A:
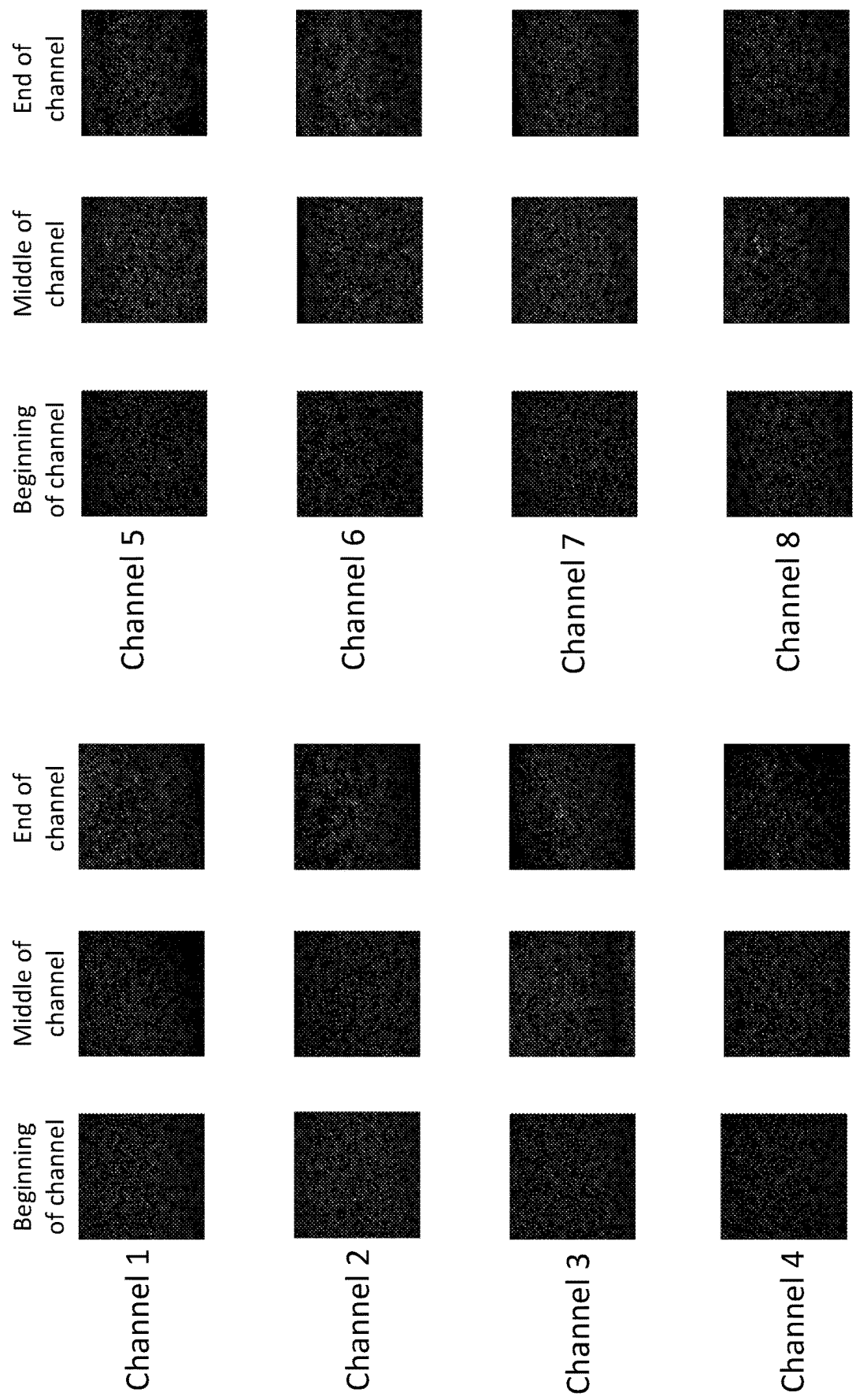
FIGS. 15A and 15B are images of exemplary cell seeding distribution of an embodiment of a 16-channel bioreactor.
Figure 15B:
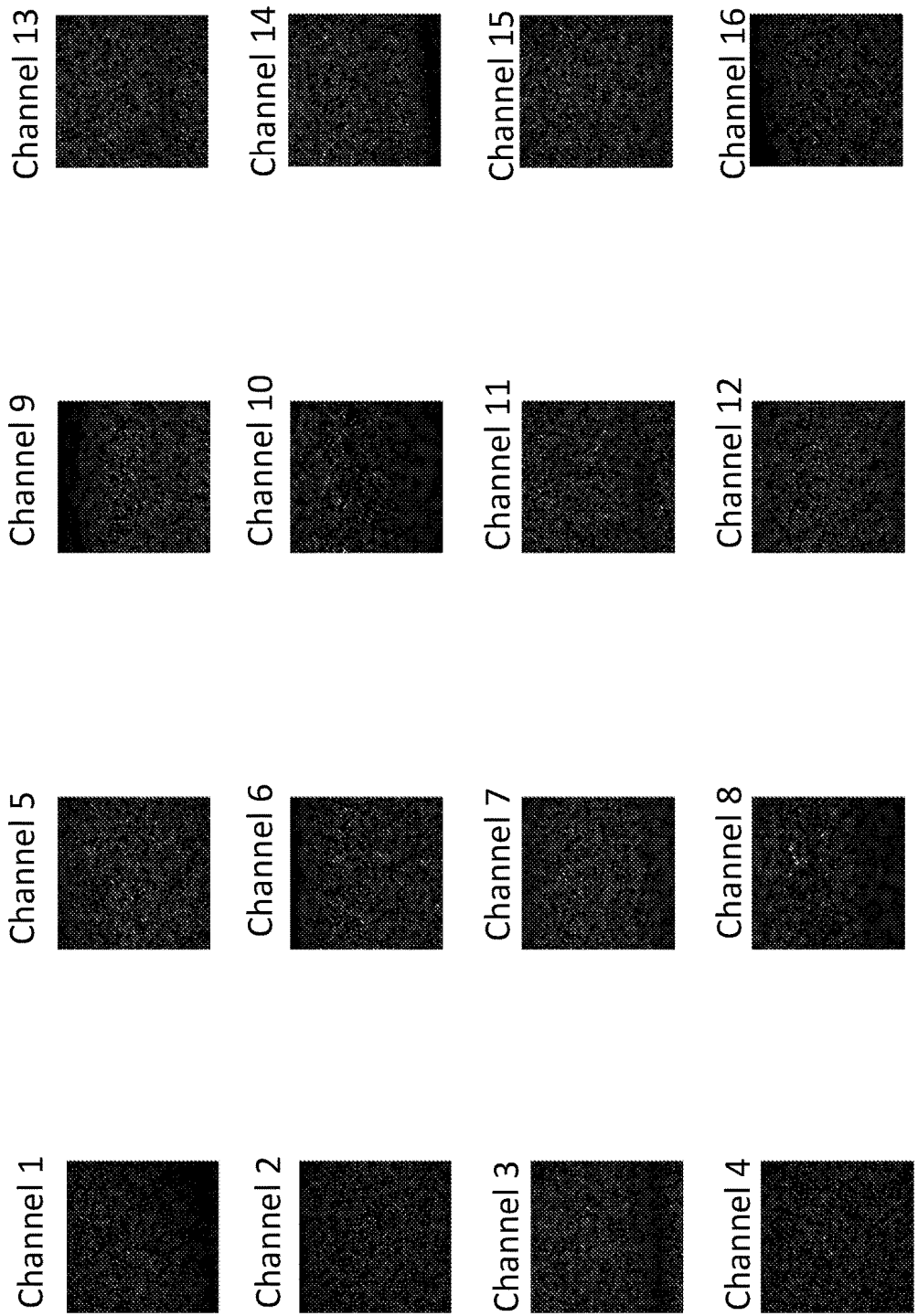

FIGS. 15A and 15B illustrate a cell seeding distribution of a 16-plex device, with a single inlet for the first channels and a single inlet for the second channels. The seeded cells are induced pluripotent stems cells differentiated into megakaryocytes and stained for nuclei with the fluorescent dye Hoechst, and visualized through the "fire" representation in ImageJ, with hot spots representing higher fluorescent signal and black or cold spots representing low fluorescent signal. FIG. 15A shows three sections of the first 8 channels of the device: beginning, middle, and end. FIG. 15B shows middle section for each of the 16 channels.

Figure 16:
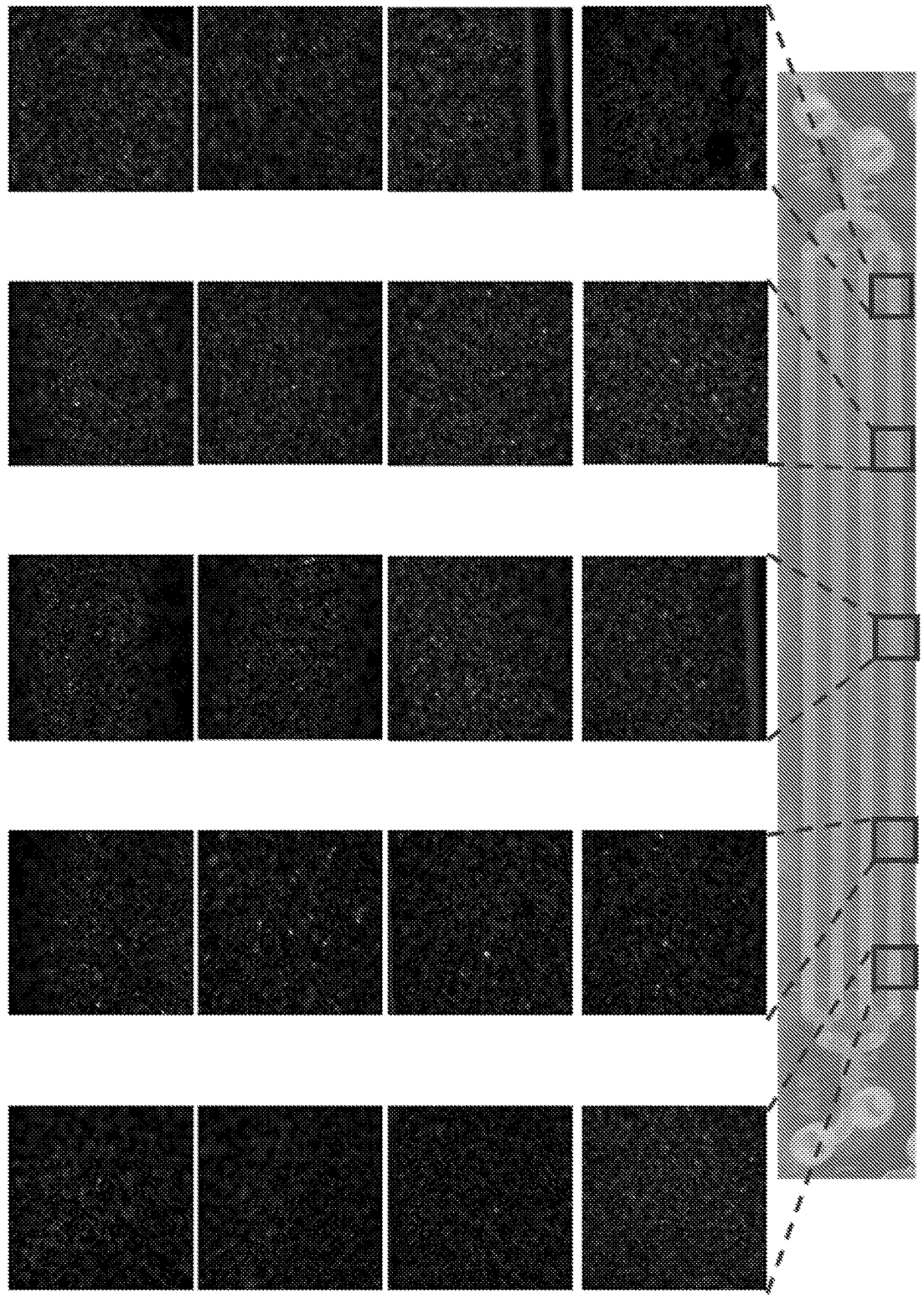
FIG. 16 is an image showing exemplary cell seeding distribution of an embodiment of a four-channel bioreactor.

As explained above, multiple flow path bioreactors can have any number of channels. For example, a bioreactor can include four channels, and FIG. 16 illustrates a cell seeding distribution of a 4-plex device, with a single inlet for the first channels and a single inlet for the second channels. The seeded cells are induced pluripotent stems cells differentiated into megakaryocytes and stained for nuclei with the fluorescent dye Hoechst, and visualized through the "fire" representation in ImageJ, with hot spots representing higher fluorescent signal and black or cold spots representing low fluorescent signal.

Figure 17B:
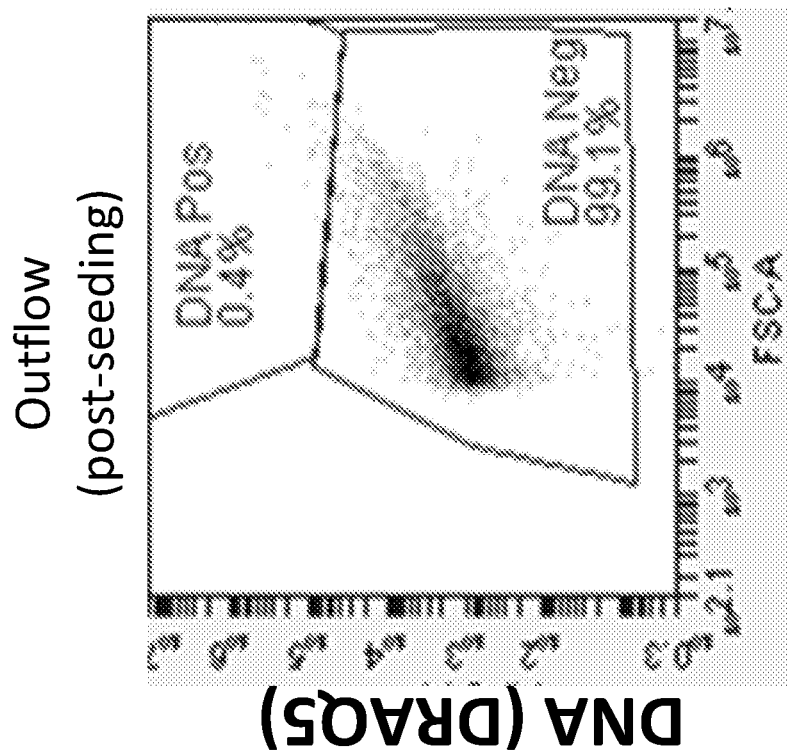
FIG. 17A and FIG. 17B are flow cytometry plots showing a mixed population of large nucleated cells and platelet sized particles prior to seeding the cells (FIG. 17A) and post seeding the cells (FIG. 17B) in the bioreactor.
Figure 17A:
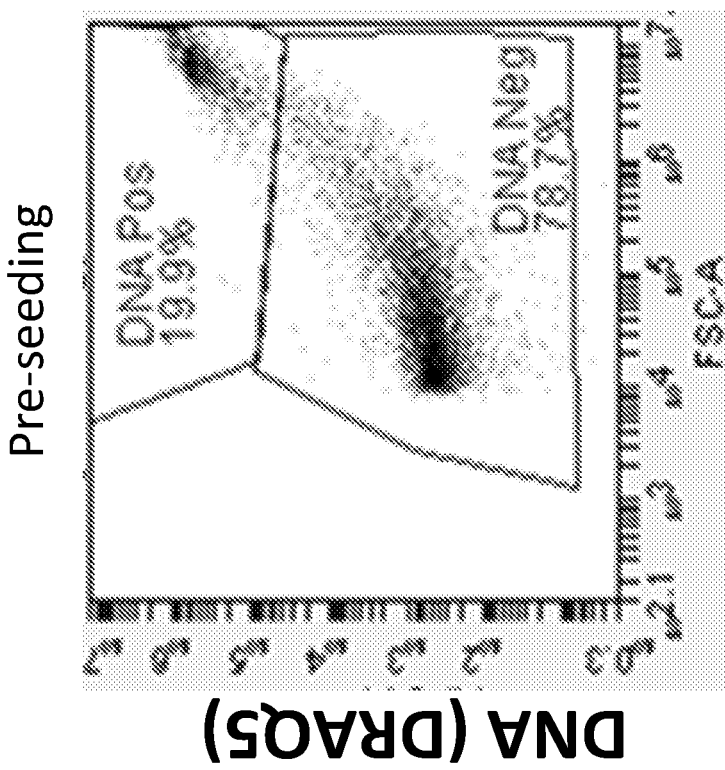

As noted above, in some embodiments, the membrane used in the present bioreactors can include pores sized to selectively capture, a biological source material capable of generating biological products and to permit the generated biological products to pass into the second channel. For example, the flow cytometry plots in FIG. 17A and FIG. 17B show a mixed population of large nucleated cells and platelet sized particles prior to seeding the cells in the bioreactor, and virtually only platelet sized particles in the outflow after seeding, indicating that all the nucleated cells, larger than the pore size, remain in the bioreactor, while smaller particles flow through the membrane pores.

Figure 18:
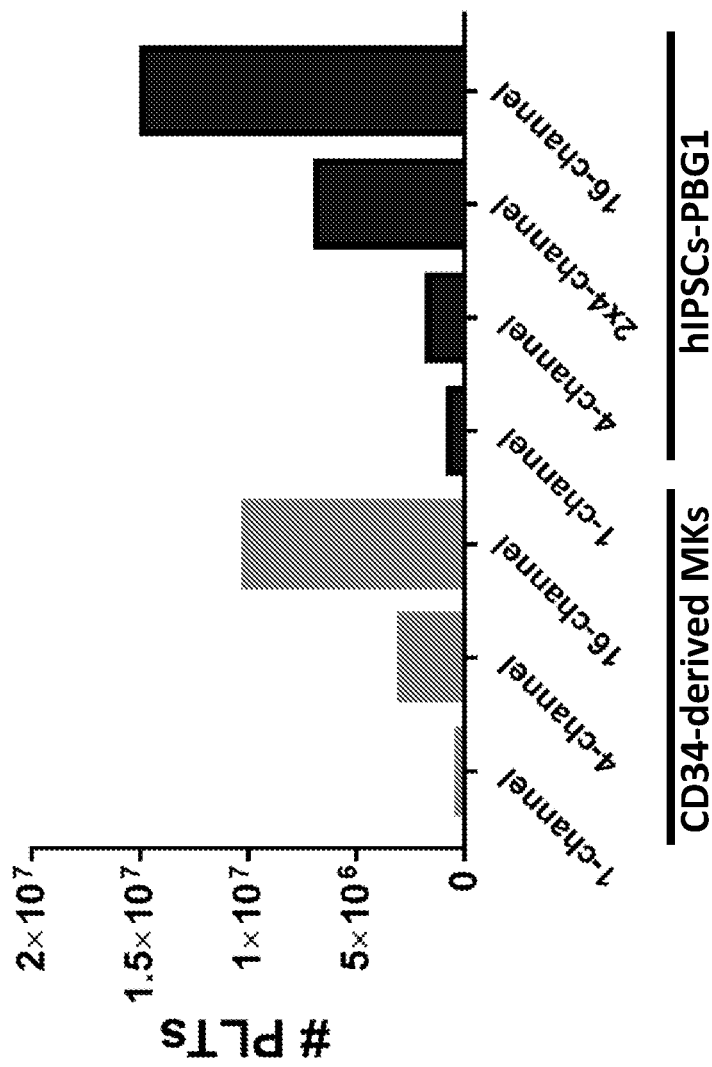
FIG. 18 is an exemplary graph illustrating platelet production using various embodiments of bioreactors with different yields per number of flow paths.

The various configurations relating to the number of channels per device and the number of stacked devices can affect platelet production. For example, FIG. 18 illustrates an exemplary graph of platelet production at 3 hours using single channel, 4-plex, 2 combined 4-plex (2×4-channel), or 16-channel devices, as indicated in the figure. Platelet production experiments were done with two different cell types: human donor CD34-derived megakaryocytes and human induced pluripotent stem cells. For all devices, each individual channel was seeded with the same number of cells. Platelets were defined as DNA negative, CD61 and CD41 double positive cells by flow cytometry.

In some embodiments, various portions of the bioreactor can be configured to allow for assembly and disassembly. In some embodiments, the first substrate, membrane, and second substrate can be configured to be removably coupled to one another. When engaged using fasteners, clips, or other releasable locking mechanisms, for example, a hermetic seal can then be formed between various surfaces of the substrates and membrane to reinstate fluid pathway integrity between the first and second inlets and the first and second outlets. It will be understood that any type of connector can be used to connect the various components of the bioreactor as long as a hermetic seal can be achieved. This capability can facilitate preparation, as described above, as well as cleaning for repeated use. In addition, disassembly allows for quick exchange of various components, for repurposing or rapid prototyping. For instance, a membrane having different pore sizes, or different preparations, can be readily swapped.

Alternatively, the bioreactor can be manufactured as a unitary device. In some embodiments, the bioreactor can be formed as a unitary device using an insert casting technique or an injection molding technique, where the membrane can be molded into the substrates. Such implementations can be advantageously integrated into large scale manufacturing techniques. In some embodiments, the first and second substrates can be manufactured separately and then bonded together by using an adhesive and/or thermal bond to permanently couple the first substrate, the membrane, and the second substrate together. It will be understood that any technique can be used to produce a unitary bioreactor, which may be desirable to ensure that there is no leakage from the channels of the bioreactor.

In addition, configurations of the bioreactor can be chosen to allow cooperation with other instrumentation, such as microscopes or cameras. For instance, the bioreactor can be configured to adhere to standard microplate dimensions. However, it will be apparent in view of this disclosure that any number of dimensions or configurations can be used in accordance with various embodiments to permit connection to any number and type of instruments, operational infrastructure devices, and/or additional bioreactors.

Figure 19:
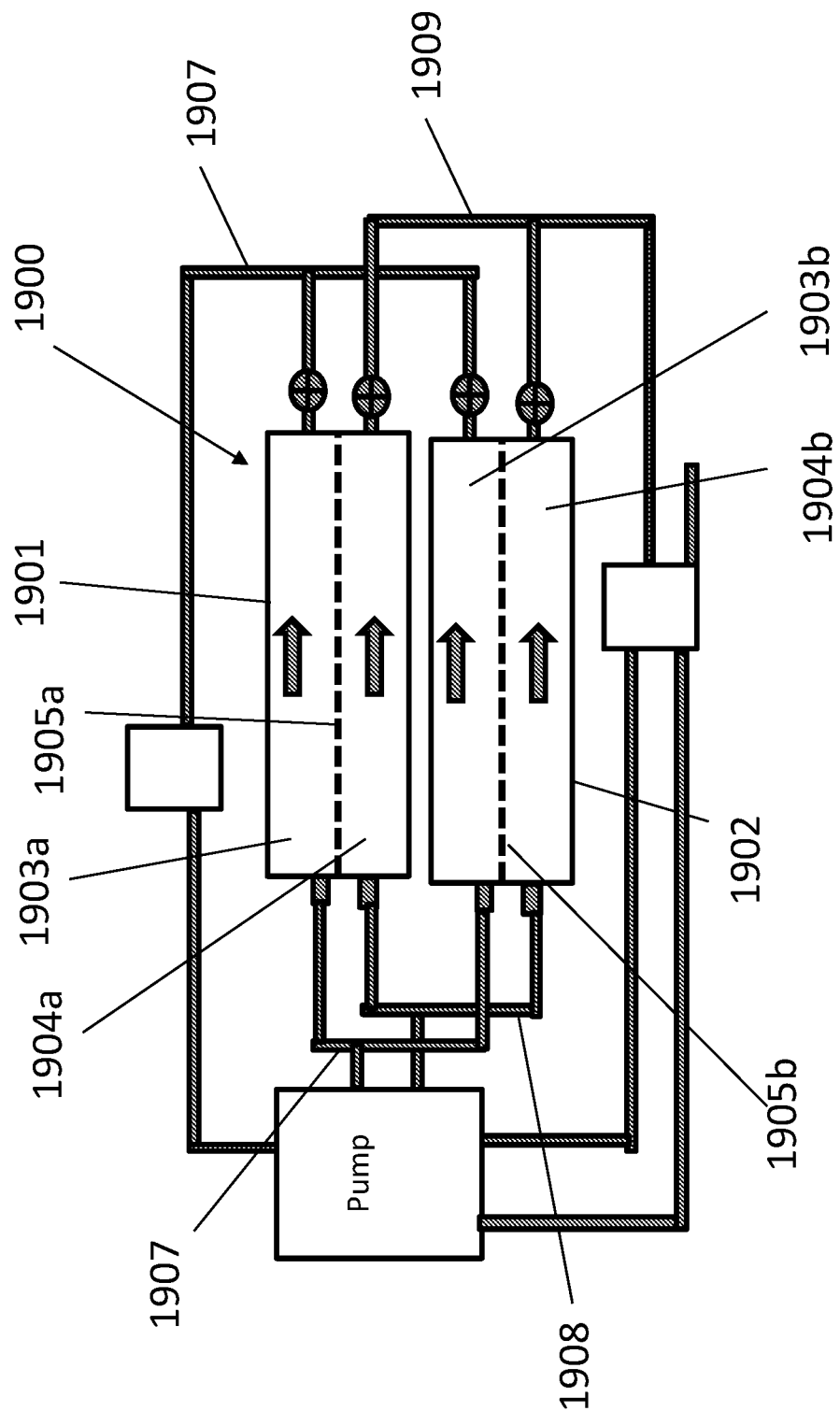
FIG. 19 is an exemplary embodiment of a priming configuration of a stacked bioreactor system.
Figure 20:
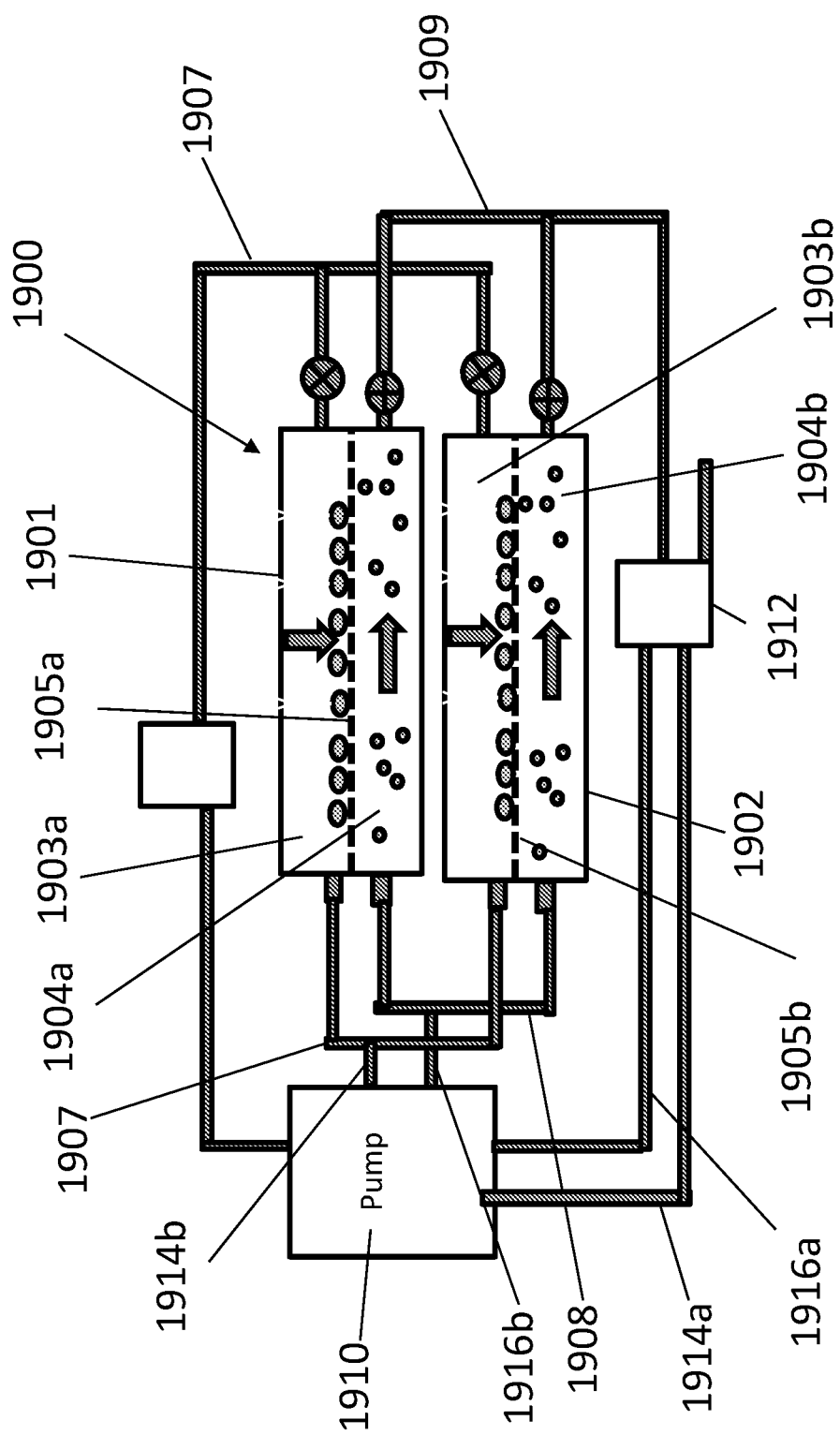
FIG. 20 is an exemplary embodiment of an operating configuration of a stacked bioreactor system.

FIG. 19 and FIG. 20 illustrate a system for the production of a biological product including a stacked bioreactor 1900 comprising of 2 individual bioreactors 1901 and 1902. Each individual bioreactor includes a first channel 1903a,b and a second channel 1904a,b separated by a membrane 1905a,b. The system further includes a first inlet manifold 1906 and a first outlet manifold 1907 that are fluidly connected to the first channels, as well as a second inlet manifold 1908 and a second outlet manifold 1909 that are fluidly connected to the second channels. In some embodiments, the first inlet manifold and the second inlet manifold are supplied with fluid via a single pump head (such as, from a peristaltic pump) to ensure a consistent flow through the first channels and the second channels.

In reference to FIG. 19, prior to the operation of the stacked bioreactor 1900, the individual bioreactors 1901, 1902 in the stacked bioreactor configuration can be primed with a low surface tension fluid, such as for example, alcohol. During the priming step, the first and second channel outlets are open to allow air to flow out of the channels. Once primed, the low surface tension solution is flushed out using a fluid, such as, culture medium to be used for the operation of the bioreactors for platelet production.

In reference to FIG. 20, next, the biological source material can be seeded onto the membrane. In some embodiments, the first channel outlet can be closed and equal amounts of fluid are pumped into the first channel inlet and second channel inlet of the individual bioreactors. During the seeding phase, the biological source material is introduced into the first channel inlet and comes to rest on the membrane. In some embodiments, the fluid from the first channel flows through membrane and deposits the biological source material on the membrane. As is described in more detail below, in some embodiments, a substantially same amount of the biological material can be delivered to each of the individual bioreactors. In addition, the biological source material is distributed evenly across the surface of each membrane. In some embodiments, a desired concentration of the biological source material is added to the operating fluid and is delivered to individual bioreactors. Because the flow rate through each bioreactor is substantially equal and because, within each bioreactor, the flow rate per unit area of the membrane is substantially constant across the membrane, the biological source material can be distributed evenly across the membrane.

In some embodiments, to accomplish the uniform seeding of the biological source material, both the first outlet and second outlet can be closed, and the fluid flow is directed from the first inlet to the second inlet, that is, the second channel inlet is used as an outlet from the bioreactor. The biological source material can then be introduced into the first channel inlet, which can cause the biological source material to be deposited on the membrane on the portion of the membrane that is closest to the inlet. The operating fluid flows through the pores of the membrane and out through the second channel inlet. As the pores that are close to the inlet fill the flow is forced to move down the device to pass through the open pores of the membrane, because the operating fluid flows in and out at the same end of the device. This can create a wave of seeding that starts at the inlet end and gradually progresses down the device to the outlet end.

The seeding step ends with a uniform distribution of the biologic material on the surface of the membrane in the first channel.

In reference to FIG. 20, an operating set up of the stacked bioreactor with 2 individual bioreactors is shown. The first outlet is closed so that the fluid introduced to the first channel flows through the membrane into the second channel. The fluid flow from the first channel combines with the fluid introduced into the second channel and the mixture flows out of the bioreactor through the second outlet.

As discussed above, the fluid rates can be configured to maintain shear rates in a predetermined range to enable efficient production of desired biological products from the biological source material. In some embodiments, such predetermined range may be between $10\ s^{-1}$ and $10{,}000\ s^{-1}$, although other values can be possible. In some embodiments, physiological shear rates consistent with proplatelet extension and platelet production in vivo may be desirable. For example, physiological shear rates can be between 500 $s^{-1}$ and 2500 $s^{-1}$. In some embodiments, the shear rates are limited as not to damage the biological products. For example, in some embodiments, the shear rates may be kept under 700 $s^{-1}$ to prevent the platelets from being activated. On the other hand, the shear rate can be sufficient to carry the platelets out of the second channel for harvesting. For example, a desired share rate can be between 400 $s^{-1}$ and 600 $s^{-1}$ to prevent the settling of the platelets in the channel, but also to prevent the platelets from being activated. In various embodiments, the shear rates can be changed by changing one or more of the size of the channels, the flow rate in the first channel, or the flow rate in the second channel. In some embodiments, the shear stress along the length of the membrane is substantially uniform throughout the length of the second channel.

The ratio of the flow rates operating in the first channel and the second channel can be varied as long as the channel shapes are varied to maintain the desired shear rates on the surface of the membrane in the second channel. In some embodiments, for the ease of operating, the ratio of the flow rates can be 1:1 (equal flow rates), which can allow the operating fluid to be delivered to the first channel and the second channel from a single peristaltic pump head, which enables a uniform pulsatile flow through the bioreactor, while preventing the dislodging of the biological source material from the membrane due to the pulsatile flow in the second channel being inconsistent or out of phase with the flow through the first channel. As shown in FIG. 20, in some embodiments, even though a single pump head is used, the flow paths through the first channels and the second channels are separately delivered by the single pump head to the inlet manifolds. For example, in operation, the fluid for the first channels is delivered to the pump 1910 from the reservoir 1912 through tubing 1914a and then is delivered from the pump 1901 to the first inlet manifold 1907 through tubing 1914b. On the other hand, the fluid for the second channels is delivered to the pump 1910 from the reservoir 1912 through tubing 1916a and then is delivered from the pump 1901 to the second inlet manifold 1908 through tubing 1916b. The tubing sets 1914a,b and 1916a,b are separate.

As shown in FIG. 20 and discussed above, the operating fluid is delivered to the first channel (or channels in the case of a multi-channel bioreactor) of each bioreactor bioreactors through a first manifold and to the second channel (or channels in the case of a multi-channel bioreactor) through a second manifold. As discussed above, these manifolds are designed such that a pressure drop through individual bioreactors (that is, pressure drop between the first and second inlets and the second outlet) in the stacked bioreactor configuration is substantially the same or equal, regardless of which bioreactor in the stack it passes though while the flow rate to each bioreactor is similar. In this manner, the flow rate of the operating fluid through the first channel and the second channel of the individual bioreactor can also be substantially the same or equal. In some embodiments, the substantially equal pressure drop across the individual device can be helped by one or more factors, such as, a uniform distribution of the biological source material through the individual bioreactors so that the membranes have the same percentage of the open pores for the operating fluid to flow between the first and second channels, which can enable a uniform pressure drop across the membrane in all the bioreactors and a uniform distribution of the biological source material along the membrane to ensure a substantially the same pressure drop per unit of membrane area.

The produced biological products can be harvested at the outlet from the second channel. In some embodiments, the operating fluid can be recycled back to the stacked bioreactor.

During a single use of the bioreactor, additional biological source material can be added to the stacked bioreactor to reseed the bioreactor as the original material becomes depleted or inactive. In some embodiments, the biological source material can be serially added to the bioreactors by introducing biological source material through the first channel inlet, with the same flow path configuration as in the device operation. In some embodiments, the outlet of the first channel can be open to remove the source material so the membrane surface is available for repeated seeding of new source material with substantially similar inlet flow rate. In some embodiments, the outlet of the bottom channel can be closed, and the outlet of the first channel open, with substantially equal inlets flow rate to force fluid through the membrane into the first channel to aid in removing the biological source material After the operation, the operating fluid from the bioreactor can be recovered by pumping fresh fluid (not recirculated) through the device until all the biological product material is pushed out of the device and collected. The harvesting step can also be achieved by venting the outlets to atmosphere and allowing the contents of the block to drain or be pumped back to the inlets. This can empty the block but collect the biologic seed material with the resultant material.

Figure 22:
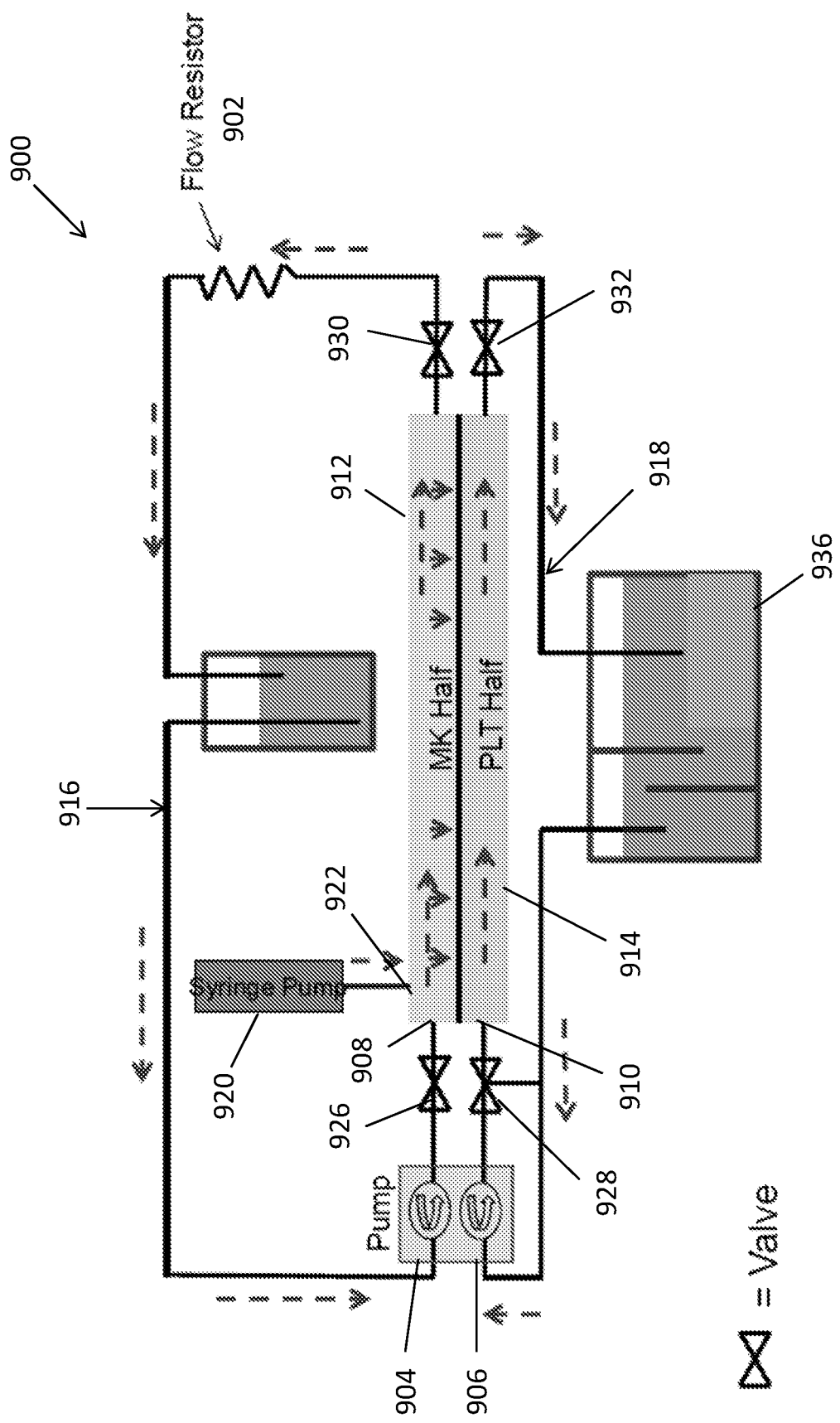
FIG. 22 is a schematic showing a recirculating bioreactor in accordance with various embodiments.

The bioreactor can also include a number of fluidic filtration and resistive elements, connected to the channels and arranged at various points along the various fluid pathways extending between the inlets and outlets. FIG. 22 illustrates an exemplary embodiment of a bioreactor 900 that includes filtration and resistive features. For instance, one or more filtration elements (not shown) can be placed proximate to one or more of the inlets to capture contaminants or undesirable substances or materials from an inputted fluid medium. In addition, one or more resistive elements 902 can also be included to control flow forces or damp fluctuations in flow rates. In addition to resistive and filtration elements, additional elements can also be included. For example, one or more of the inlets can include bubble traps configured to prevent any air bubbles from entering the bioreactor. In some embodiments, one or more of the inlets can include an in-line mixer for, for example, homogenizing the first fluid flow with the biological source material or, for example, homogenizing the second fluid flow with the biological products.

Figure 21:
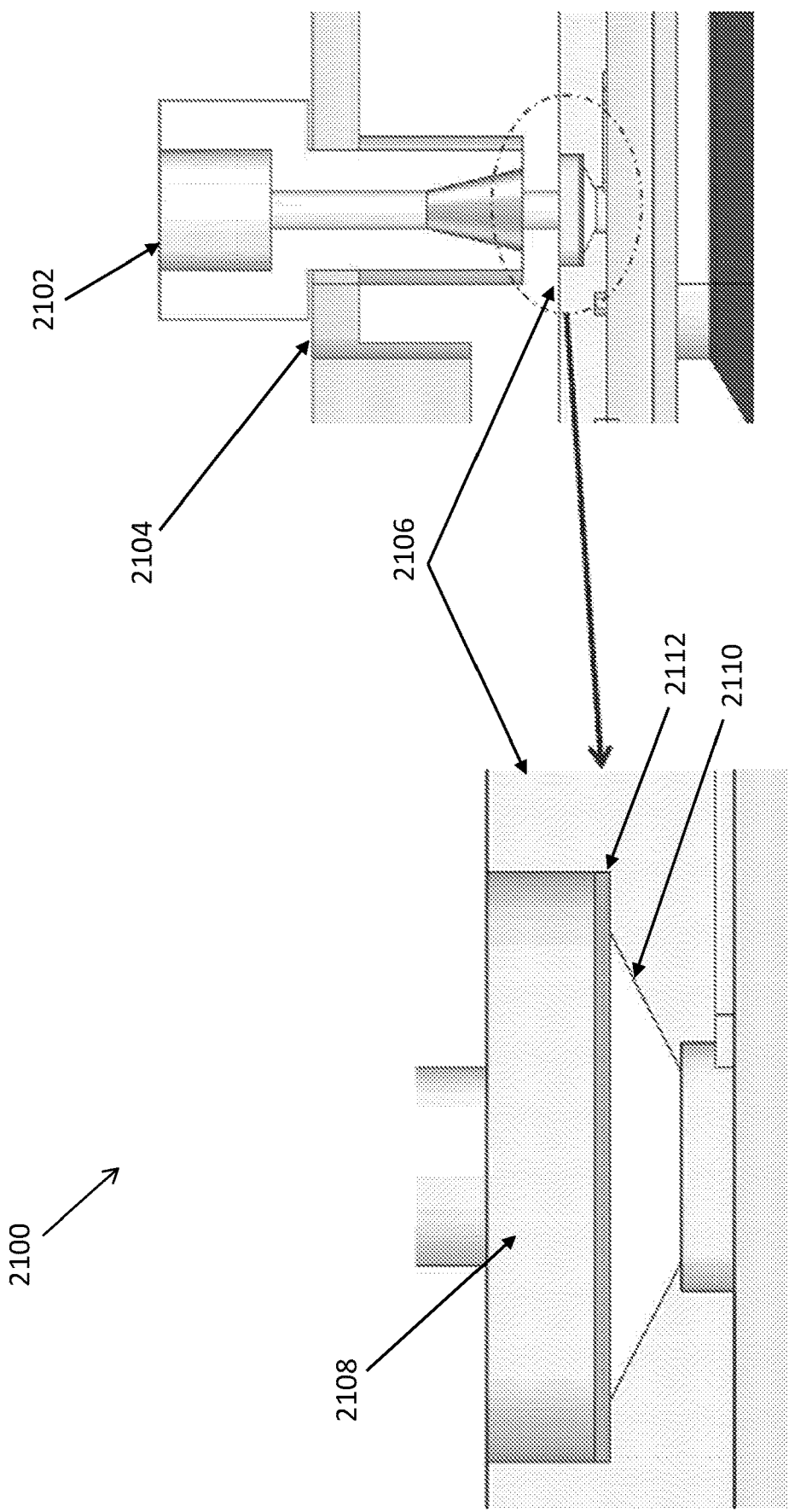
FIG. 21 is a cross-sectional view of a port having a bubble trap in accordance with various embodiments.

By way of a non-limiting example, FIG. 21 illustrates a port 920 that includes fluidic connector or port 922 coupled to an inlet 9244 of an exemplary bioreactor, in accordance with various embodiments. As shown, the inlet 804 has a bubble trap 806 that includes an expansion region 808 and a conical region 810 separated by a mesh 812. The size of the mesh 812 can vary, but in some embodiment the mesh 812 can have a size of approximately 140 micrometers, although other values can be possible. As configured, the bubble trap is capable of preventing air bubbles from entering the bioreactor.

As shown in FIG. 22, in some embodiments, a bioreactor can be included in a recirculating bioreactor 900. In some embodiments, the recirculating bioreactor 900 can include a bioreactor 104 as described above with reference to FIGS. 5A-5C and 6A-6H. In some embodiments, the recirculating bioreactor 900 can include first and second pumps 904, 906 for recirculating flow from the first and second outlets 912, 914 back to the first and second inlets 908, 910 via first and second recirculation lines 916, 918. In some embodiments, the recirculating bioreactor can include a third pump 920 (e.g., a syringe pump as shown) for delivering a biological source material to the first channel 924 via the third inlet 922. In some embodiments, one or more valves can be positioned in fluid communication with each of the inlets and outlets to permit, prevent, or control flow thereto. In the illustrated embodiment, each inlet 908, 910 and each outlet 912, 914 are associated with a valve 926, 928, 930, 932. In some embodiments, one or more reservoirs 932, 936 can be included to store excess fluid media of the first and/or second flows during operation. In some embodiments, at least one reservoir can be configured to separate a biological product from the second flow. In some embodiments, one or more flow resistors 902 can be added to one or more of the recirculation lines to provide additional control over flow rates and pressures within the bioreactor.

The first and second pumps 904, 906, in accordance with various embodiments, can be any suitable pump capable of imparting motive energy to the first and second fluid flows to promote flow through the first and second channels and first and second recirculation lines 916, 918. For example, in some embodiments the first and second pumps 904, 906 can include one or more of an impeller, a peristaltic pump, positive displacement pump, gear pump, screw pump, any other suitable pump, or combinations thereof. In some embodiments, each of the first and second pumps 904, 906 can be separately operable and reversible in order to provide independent flow control in each of the first and second channels. In some embodiments, the pumps 904, 906 can be configured to vary one or more of pressure, flow, and/or shear within each of the first and second channels to provide pulsatile flow through the bioreactor. In some embodiments, the pulse rate, pressure, shear, and/or flow can be provided to substantially mimic human blood flow. For example, in some embodiments, during operation, the perfusion rate of the flow circulating within the first and second channels can be between about 1 mL/hr and about 50 mL/hr, for example, about 12.5 mL/hr and produce a wall shear rate between about 250 s$^{-1}$ and about 1800 s$^{-1}$, for example 800 s$^{-1}$ and about 1200 s$^{-1}$. Pulse rate, in accordance with various embodiments, can be about 0.5 hz to about 5 hz, for example, about 1 hz to about 2 hz.

The third pump 920, in accordance with various embodiments, can be any pump suitable or infusing a biological source material into the first channel. For example, in some embodiments the third pump 920 can be a syringe pump, a piston pump, a reciprocating pump, a diaphragm pump, any other suitable pump, or combinations thereof. In some embodiments, the third pump 920 can be configured to deliver the biological source material at a rate sufficient for seeding the membrane with the biological source material. For example, in some embodiments the biological source material can be infused at a rate of about 0.1 mL/hr to about 2 mL/hr, for example, about 1 mL/hr. However, it will be apparent in view of this disclosure that any suitable flow rate can be used in accordance with various embodiments.

The flow resistor 902, in accordance with various embodiments can include, for example, a nozzle, a tube extension, any other device suitable for metering or restricting fluid flow, or combinations thereof. The valves, in some embodiments, can be any valve known in the art for selectively permitting or preventing flow through the first or second channels and/or the first or second recirculation lines. The first and second reservoirs can be any suitable beaker, test tube, flask, bottle, jar, tank, bag, or any other suitable reservoir for retaining a fluid medium. In some embodiments, the second reservoir can further include at least one of a divider, a separator, a sorter, or any other device for removing one or more biological products from the second fluid flow, such as a hollow fiber or cross filtration device.

By way of a non-limiting example, as shown in FIG. 22, a bioreactor of the present disclosure can be seeded using a double flow seeding technique. In the double flow seeding technique biological source materials dispersed in a fluid media are added to the first channel via the third inlet and with both pumps in operation such that the first fluid flow is provided through the first channel and the first recirculation line and the second flow is provided through the second channel and the second recirculation line. In order to prevent or reduce continuous recirculation (without capture by the membrane) of the biological source material, the flow resistor can be activated to increase pressure across the membrane. The double flow seeding technique can advantageously provide a more even distribution of the biological source material compared to the direct infusion methodology.

Furthermore, the operational configuration depicted in FIG. 22 can also be used after seeding, regardless of the seeding technique used, for actual operation of the recirculating bioreactor to produce biological products. In some embodiments, a flow resistor 902 can be used, for example, to increase pressure in the first channel by increasing the pressure drop between the first channel and the outlet. In some embodiments, the flow resistor 902 can be provided as a length of tubing having an inner diameter large enough for a seeding cell to pass through but small enough (and long enough) to create a desired rise in pressure. The increased pressure in the first channel can create a pressure differential for holding the seeded biological source material against the membrane pores, thereby permitting the seeded biological source material to maintain their position in a membrane pore and not be swept away or dislodged by other forces such as higher operational fluid media flow rates. Having a significant about of flow exiting the first channel outlet is a useful method of clearing bubbles from the device and is therefore an ideal way to prime the reactor before seeding the reactor with biological source material.

Figure 23A:
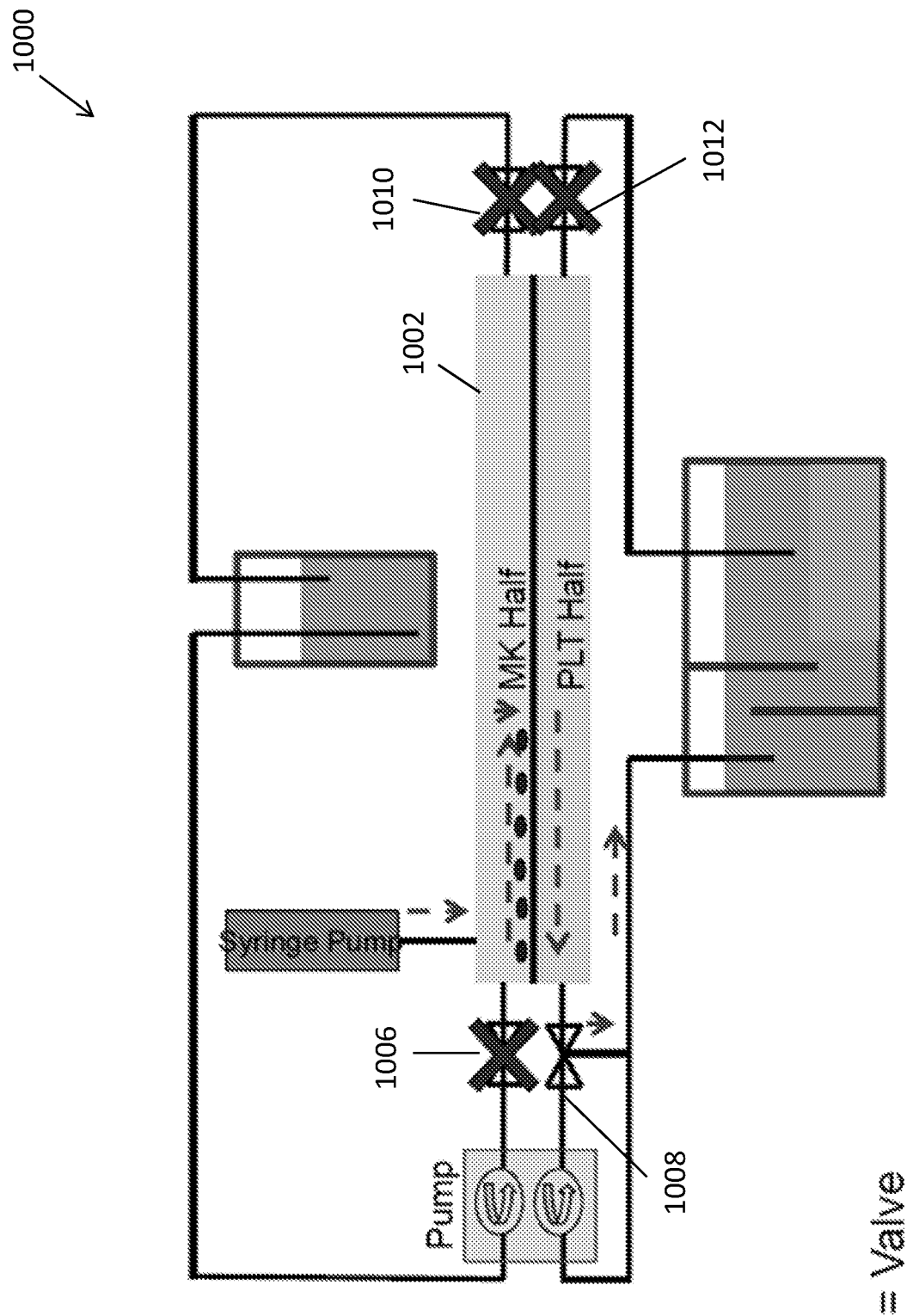
FIGS. 23A and 23B are functional flow diagrams illustrating a pressure wave method for seeding a bioreactor in accordance with various embodiments.
Figure 23B:
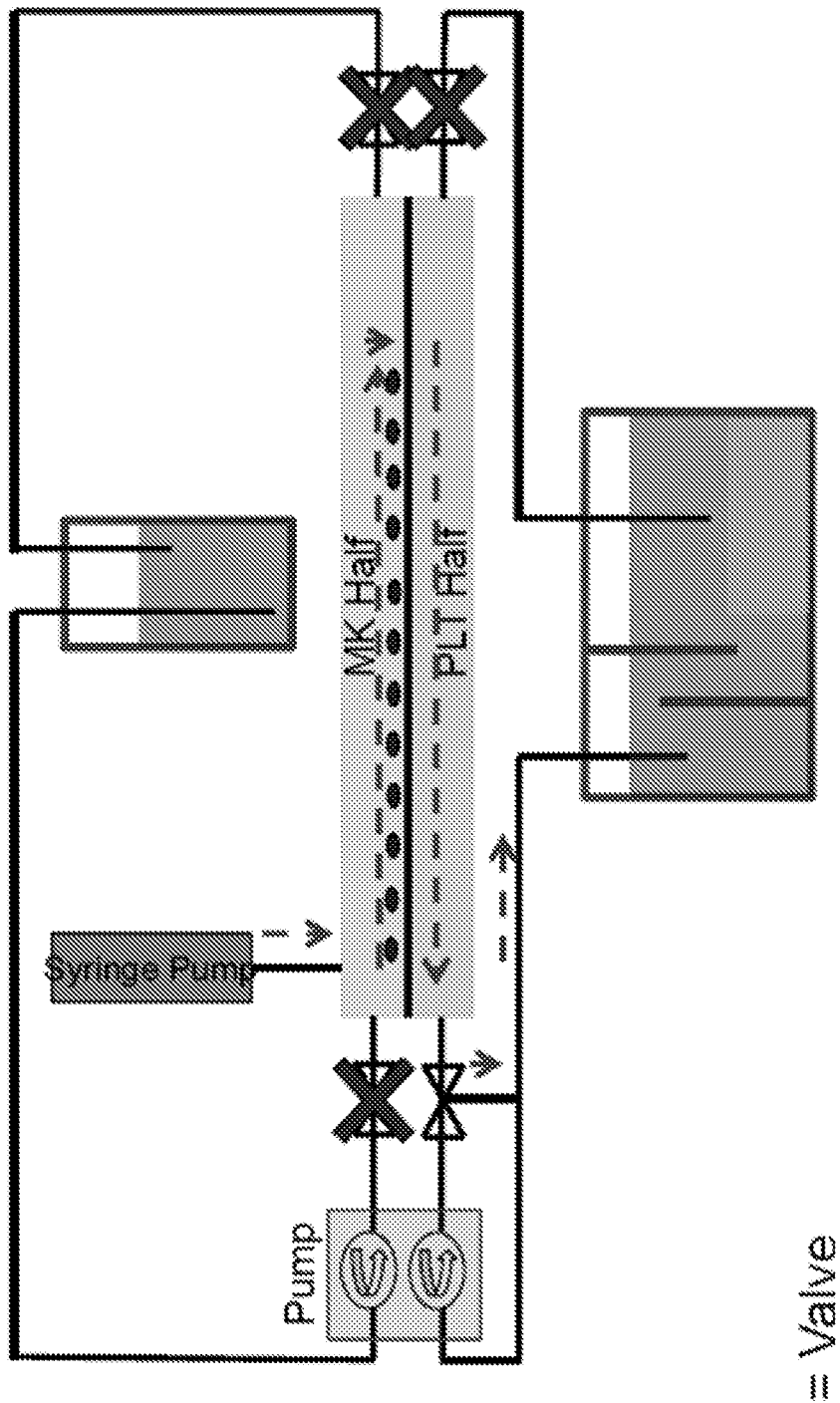

FIGS. 23A-23B illustrate an embodiment of a recirculating bioreactor 1000 seeded using a pressure wave seeding technique. In the pressure wave seeding technique, biological source materials dispersed in a fluid media are added to a first channel 1002 via the third inlet with valves 1006, 1010, 1012 controlling the first inlet, the first outlet, and the second outlet closed and the valve 1008 controlling the second inlet open. Although described herein as closed, the valve 1006 associated with the first inlet, in some embodiments, can be minimally open. For example, in some embodiments, one or both of the first or second inlets can be about 10% open to permit a small flow therethrough, thus preventing inadvertent collection of biological source material in the first or second inlets. The fluid media is then flowed from the third inlet to the second inlet. Because of the valve closures, the first inlet and first and second outlets are blocked. Thus, fluid media passes through the membrane to exit the bioreactor 1000. Because the pores in the membrane are sized and configured to capture the biological source material, the biological source material becomes lodged in the pores of the membrane. Initially, as shown in FIG. 23A, the biological source material is captured by the closest pores to the third inlet and then, as the closest pores are blocked, subsequent biological source material travels through the channel to reach the next available open pores as shown in FIG. 23B. Accordingly, the pressure wave seeding method lays down a layer of cells with one cell on each pore as flow is gradually blocked through the membrane. The pressure wave seeding method advantageously provides even placement of the biological source material throughout the membrane. Additionally, because the flow is gradually blocked through the membrane, by measuring the pressure drop across the membrane curing this process, the number of open and filled pores can be estimated. In some embodiments, the flow can be a time varying function to provide shear temporal variation, mimicking a pulsatile physiological blood flow rate.

Figure 24:
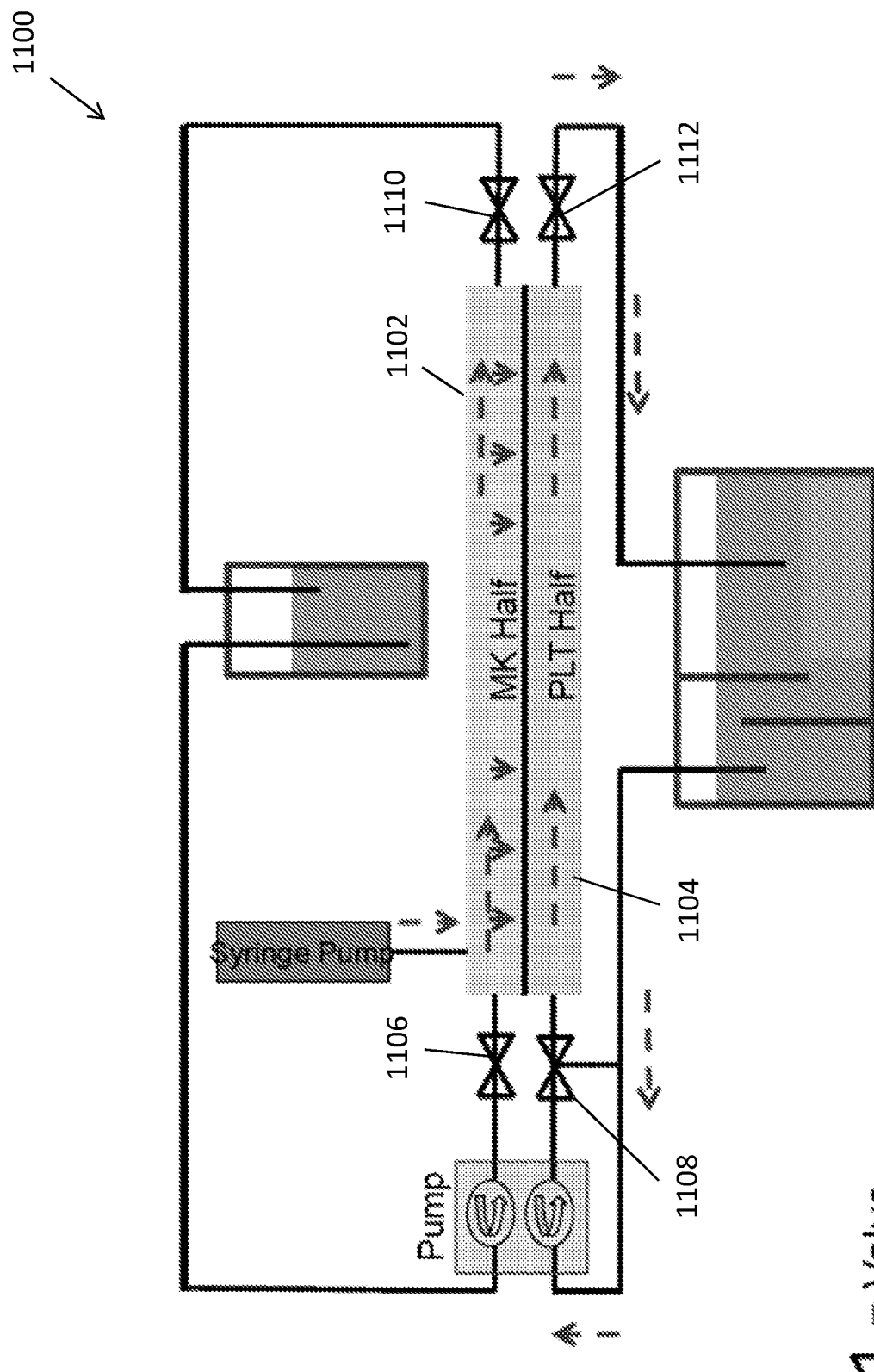
FIG. 24 is a functional flow diagram illustrating a direct infusion method for seeding a bioreactor in accordance with various embodiments.

FIG. 24 illustrates an embodiment of a recirculating bioreactor 1100 seeded using a direct infusion seeding technique. In the direct infusion seeding technique biological source materials dispersed in a fluid media are added to the first channel 1102 via the third inlet with all valves 1106, 1108, 1110, 1112 open. The first pump 914 is inactive and the second pump 1116 is operated to provide flow through the second channel 1104 and the second recirculation line. This method prevents the biological source material from being recirculated during seeding because the first pump 1114 is inactive. In some embodiments, direct infusion seeding results in concentrations of biological source material proximate the first inlet and the first outlet, with relatively little biological source material in the middle portions of the bioreactor. It will be apparent in view of this disclosure, however, that in some embodiments, the first pump, to prevent inadvertent collection of biological source material at the first inlet, can be operated at a speed slow enough to avoid recirculation of the biological source material, for example, about 10% operational flow rate.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A system comprising:
a plurality of stacked bioreactors stacked in a vertical configuration to define a height, each bioreactor comprising:
a first channel configured to receive at least one first fluid at a first channel flow rate;
a second channel configured to receive at least one second fluid at a second channel flow rate;
a separation barrier between the first channel and the second channel, the separation barrier having a plurality of microchannels forming a fluid communication path between the first channel and the second channel;
a first main inlet channel having a plurality of first secondary inlet channels in fluid communication with the first channel of each of the plurality of stacked bioreactors and configured to distribute flow through the first channel of each of the plurality of stacked bioreactors;
a second main inlet channel having a plurality of second secondary inlet channels in fluid communication with the second channel of each of the plurality of stacked bioreactors and configured to distribute flow through the second channel of each of the plurality of stacked bioreactors;
a first main outlet channel having a plurality of first secondary outlet channels in fluid communication with the first channel of each of the plurality of stacked bioreactors to collect the at least one first fluid from the bioreactors; and
a second main outlet channel having a plurality of second secondary outlet channels in fluid communication with the second channel of each of the plurality of stacked bioreactors to collect the at least one second fluid from the bioreactors;
wherein the system is configured to provide a substantially equal flow rate of the at least one first fluid and the at least one second fluid through each of the plurality of stacked bioreactors;
wherein a length of each of the plurality of first secondary inlet channels and the plurality of second secondary inlet channels decreases as the height increases; and
wherein a length of the plurality of first secondary outlet channels and the plurality of second secondary outlet channels increases as the height increases.

2. The system of claim 1, wherein a flow path through the plurality of stacked bioreactors is configured to ensure a substantially equal pressure drop across each of the plurality of stacked bioreactors.

3. The system of claim 2, wherein the substantially equal pressure drop across each of the plurality of stacked bioreactors ensures a substantially equal flow through each of the plurality of stacked bioreactors.

4. The system of claim 1, wherein the first main inlet channel and second main inlet channel are shaped to ensure a substantially equal pressure drop across each of the plurality of stacked bioreactors.

5. The system of claim 1, wherein the first main inlet channel and second main inlet channel include an insert to create a substantially equal pressure drop across each of the plurality of stacked bioreactors.

6. The system of claim 1, wherein the first channel, the second channel or both have a variable cross-section along the length to impart a consistent pressure drop across the separation barrier along the length of the separation barrier.

7. The system of claim 6, wherein the consistent pressure drop across the separation barrier along the length of the separation barrier ensures a substantially equal flow through the separation barrier along its length to distribute the at least one first fluid substantially equally along the length of the separation barrier.

8. The system of claim 1, further comprising one or more pumps in fluid communication with the first main inlet channel and second main inlet channel.

9. The system of claim 8, wherein a single pump head is configured to provide flow to the first main inlet channel and second main inlet channel to ensure a substantially equal pulsatile flow in each of the first main inlet channel and second main inlet channel.

10. The system of claim 1, wherein each bioreactor further comprises a bioreactor body and wherein the first channel, the second channel, a portion of the first main inlet channel and a portion of the second main inlet channel are formed in the bioreactor body of each bioreactor.

11. A system comprising:
a plurality of stacked bioreactors stacked in a vertical configuration to define a height, each bioreactor comprising:
a first channel configured to receive at least one first fluid at a first channel flow rate;
a second channel configured to receive at least one second fluid at a second channel flow rate;
a separation barrier between the first channel and the second channel, the separation barrier having a plurality of microchannels forming a fluid communication path between the first channel and the second channel; and
one or more manifold in fluid communication with each of the plurality of stacked bioreactors, the one or more manifold comprising:
one or more main inlet channels having a plurality of secondary inlet channels fluidly connecting the one or more main inlet channels to the first channel or the second channel of each of the plurality of stacked bioreactors;
one or more main outlet channels having a plurality of secondary outlet channels fluidly connecting the one or more main outlet channels to the first channel or the second channel of each of the plurality of stacked bioreactors;
wherein the system is configured to provide a substantially equal flow rate of the at least one first fluid and the at least one second fluid through each of the plurality of stacked bioreactors;
wherein a length of each of the plurality of secondary inlet channels decreases as the height increases; and
wherein a length of each of the plurality of secondary outlet channels increases as the height increases.

12. A system comprising:
a plurality of stacked bioreactors stacked in a vertical configuration to define a height, each bioreactor comprising:
a first channel configured to receive at least one first fluid at a first channel flow rate;
a second channel configured to receive at least one second fluid at a second channel flow rate;
a separation barrier between the first channel and the second channel, the separation barrier having a plurality of microchannels forming a fluid communication path between the first channel and the second channel; and one or more manifold in fluid communication with each of the plurality of stacked bioreactors, the one or more manifold comprising:
  first main inlet channel having a plurality of first secondary inlet channels in fluid communication with the first channel of each of the plurality of stacked bioreactors and configured to distribute flow through the first channel of each of the plurality of stacked bioreactors;
  a second main inlet channel having a plurality of second secondary inlet channels in fluid communication with the second channel of each of the plurality of stacked bioreactors and configured to distribute flow through the second channel of each of the plurality of stacked bioreactors;
  a first main outlet channel having a plurality of first secondary outlet channels in fluid communication with the first channel of each of the plurality of stacked bioreactors to collect the at least one first fluid from the bioreactors;
  a second main outlet channel having a plurality of second secondary outlet channels in fluid communication with the second channel of each of the plurality of stacked bioreactors to collect the at least one second fluid from the bioreactors;
wherein the system is configured to provide a substantially equal flow rate of the at least one first fluid and the at least one second fluid through each of the plurality of stacked bioreactors;
wherein the first main inlet channel and the second main inlet channel converge as the height increases so as to decrease a length of each of the plurality of first secondary inlet channels and the plurality of second secondary inlet channels as the height increases; and
wherein the first main outlet channel and the second main outlet channel converge as the height decreases so as to decrease a length of each of the plurality of first secondary outlet channels and the plurality of second secondary outlet channels as the height decreases.

* * * * *